US010610205B2

(12) United States Patent
Rhad et al.

(10) Patent No.: US 10,610,205 B2
(45) Date of Patent: Apr. 7, 2020

(54) BIOPSY DEVICE

(71) Applicant: Devicor Medical Products, Inc., Cincinnati, OH (US)

(72) Inventors: Edward A. Rhad, Fairfield, OH (US); Morgan R. Hunter, Cincinnati, OH (US); Andrew P. Nock, Dayton, OH (US); Bryan R. Keller, Loveland, OH (US); Emmanuel V. Tanghal, Mason, OH (US); Rachel Yoon Choung, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 23 days.

(21) Appl. No.: 14/712,260

(22) Filed: May 14, 2015

(65) Prior Publication Data

US 2015/0327842 A1    Nov. 19, 2015

Related U.S. Application Data

(60) Provisional application No. 61/993,830, filed on May 15, 2014.

(51) Int. Cl.
*A61B 10/00* (2006.01)
*A61B 10/02* (2006.01)

(52) U.S. Cl.
CPC ...... *A61B 10/0096* (2013.01); *A61B 10/0275* (2013.01); *A61B 2010/0208* (2013.01); *A61B 2010/0225* (2013.01)

(58) Field of Classification Search
None
See application file for complete search history.

(56) References Cited

U.S. PATENT DOCUMENTS

| 5,526,822 A | 6/1996 | Burbank et al. |
| 5,928,164 A | 7/1999 | Burbank et al. |

(Continued)

FOREIGN PATENT DOCUMENTS

| CN | 101820816 A | 9/2010 |
| CN | 103764044 A | 4/2014 |
| EP | 1 932 482 A1 | 6/2008 |

OTHER PUBLICATIONS

International Search Report and Written Opinion dated Oct. 16, 2015 for Application No. PCT/US2015/030794, 8 pgs.

(Continued)

*Primary Examiner* — Sean P Dougherty
*Assistant Examiner* — Benjamin S Melhus
(74) *Attorney, Agent, or Firm* — Frost Brown Todd LLC

(57) ABSTRACT

A biopsy device includes a body, a needle, a hollow cutter, and a tissue sample holder. The needle extends distally from the body and includes a lateral aperture. The cutter is movable relative to the needle to sever a tissue sample and defines a cutter lumen. The tissue sample holder includes a manifold and an outer cover. The manifold includes a plurality of passages and an indexing portion. Each passage of the plurality of passages is configured to selectively index relative to a proximal end of the hollow cutter. The outer cover includes a resilient member. The resilient member is configured to engage with the indexing portion of the manifold to selectively index a passage of the plurality of passages with the distal end of the hollow cutter.

20 Claims, 50 Drawing Sheets

(56) References Cited

U.S. PATENT DOCUMENTS

| | | | |
|---|---|---|---|
| 6,017,316 A | 1/2000 | Ritchart et al. | |
| 6,086,544 A | 7/2000 | Hibner et al. | |
| 6,142,956 A * | 11/2000 | Kortenbach | A61B 10/0266 |
| | | | 600/564 |
| 6,162,187 A | 12/2000 | Buzzard et al. | |
| 6,228,055 B1 | 5/2001 | Foerster et al. | |
| 6,371,904 B1 | 4/2002 | Sirimanne et al. | |
| 6,432,065 B1 | 8/2002 | Burdorff et al. | |
| 6,626,849 B2 | 9/2003 | Huitema et al. | |
| 6,752,768 B2 | 6/2004 | Burdorff et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,229,417 B2 | 6/2007 | Foerster et al. | |
| 7,276,063 B2 | 10/2007 | Hibner | |
| 7,442,171 B2 | 10/2008 | Stephens et al. | |
| 7,465,279 B2 | 12/2008 | Beckman et al. | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,918,803 B2 | 4/2011 | Ritchart et al. | |
| 7,918,804 B2 | 4/2011 | Monson et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,231,545 B2 | 7/2012 | Spero et al. | |
| 8,241,226 B2 | 8/2012 | Hibner et al. | |
| 8,371,443 B2 | 2/2013 | Nock et al. | |
| 8,454,531 B2 | 6/2013 | Speeg et al. | |
| 8,532,747 B2 | 9/2013 | Nock et al. | |
| 8,532,748 B2 | 9/2013 | Leimbach et al. | |
| 8,622,924 B2 | 1/2014 | Speeg et al. | |
| 8,622,927 B2 | 1/2014 | Parihar et al. | |
| 8,702,623 B2 | 4/2014 | Parihar et al. | |
| 8,708,928 B2 | 4/2014 | Videbaek | |
| 8,764,680 B2 | 7/2014 | Rhad et al. | |
| 8,801,742 B2 | 8/2014 | Rhad et al. | |
| 8,845,546 B2 | 9/2014 | Speeg et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 2006/0074345 A1 | 4/2006 | Hibner | |
| 2006/0282012 A1 | 12/2006 | McAlister et al. | |
| 2008/0004545 A1 | 1/2008 | Garrison | |
| 2008/0214955 A1 | 9/2008 | Speeg et al. | |
| 2009/0131821 A1 | 5/2009 | Speeg et al. | |
| 2009/0209854 A1 | 8/2009 | Parihar et al. | |
| 2010/0152610 A1 | 6/2010 | Parihar et al. | |
| 2010/0160816 A1* | 6/2010 | Parihar | A61B 10/0275 |
| | | | 600/564 |
| 2010/0160819 A1 | 6/2010 | Parihar et al. | |
| 2010/0168616 A1* | 7/2010 | Schraga | A61B 5/15146 |
| | | | 600/583 |
| 2011/0071391 A1 | 3/2011 | Speeg | |
| 2011/0071423 A1 | 3/2011 | Speeg et al. | |
| 2011/0092855 A1* | 4/2011 | List | A61B 5/15146 |
| | | | 600/583 |
| 2012/0283563 A1 | 11/2012 | Moore et al. | |
| 2013/0053724 A1 | 2/2013 | Fiebig et al. | |
| 2013/0144188 A1 | 6/2013 | Fiebig et al. | |
| 2013/0218047 A1 | 8/2013 | Fiebig et al. | |
| 2013/0324882 A1 | 12/2013 | Mescher | |
| 2014/0039343 A1 | 2/2014 | Mescher et al. | |
| 2014/0275999 A1 | 9/2014 | Speeg et al. | |
| 2015/0065913 A1 | 3/2015 | Keller et al. | |
| 2016/0121057 A1* | 5/2016 | Dyche | A61M 15/009 |
| | | | 128/200.23 |

OTHER PUBLICATIONS

U.S. Appl. No. 61/566,793, filed Dec. 5, 2011.
Chinese Office Action, Notification of First Office Action, and Search Report dated Nov. 23, 2018 for Application No. CN 2015800227925, 23 pgs.
European Search Report, Supplementary, and Written Opinion dated Dec. 1, 2017 for Application No. EP 15791892.1, 7 pgs.
Korean Office Action, Notification of Reason for Refusal, dated Aug. 29, 2018 for Application No. KR 10-2016-7029951, 20 pgs.
European Office Action dated Jul. 5, 2019 for Application No. EP 15791892.1, 6 pages.

* cited by examiner

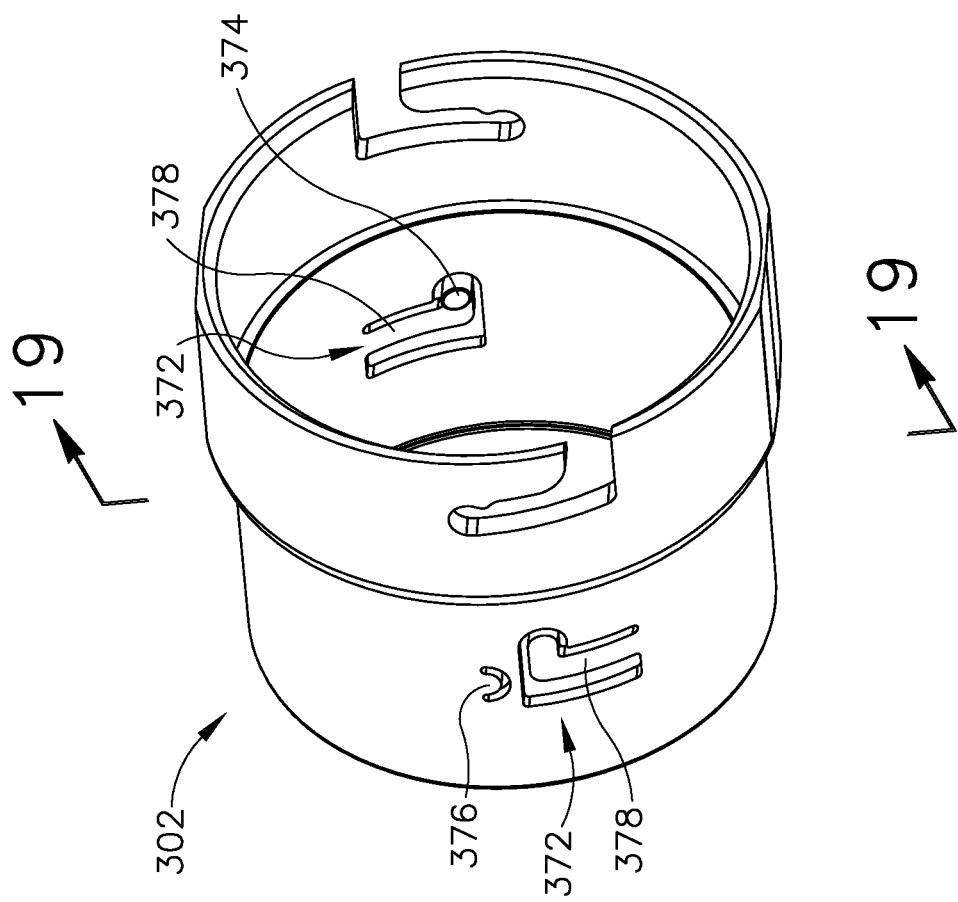
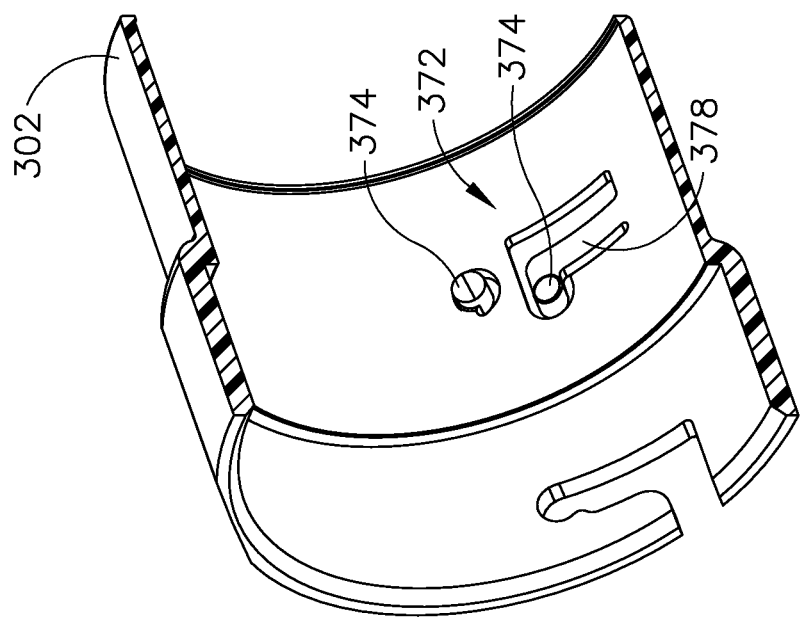
Fig.18
Fig.19

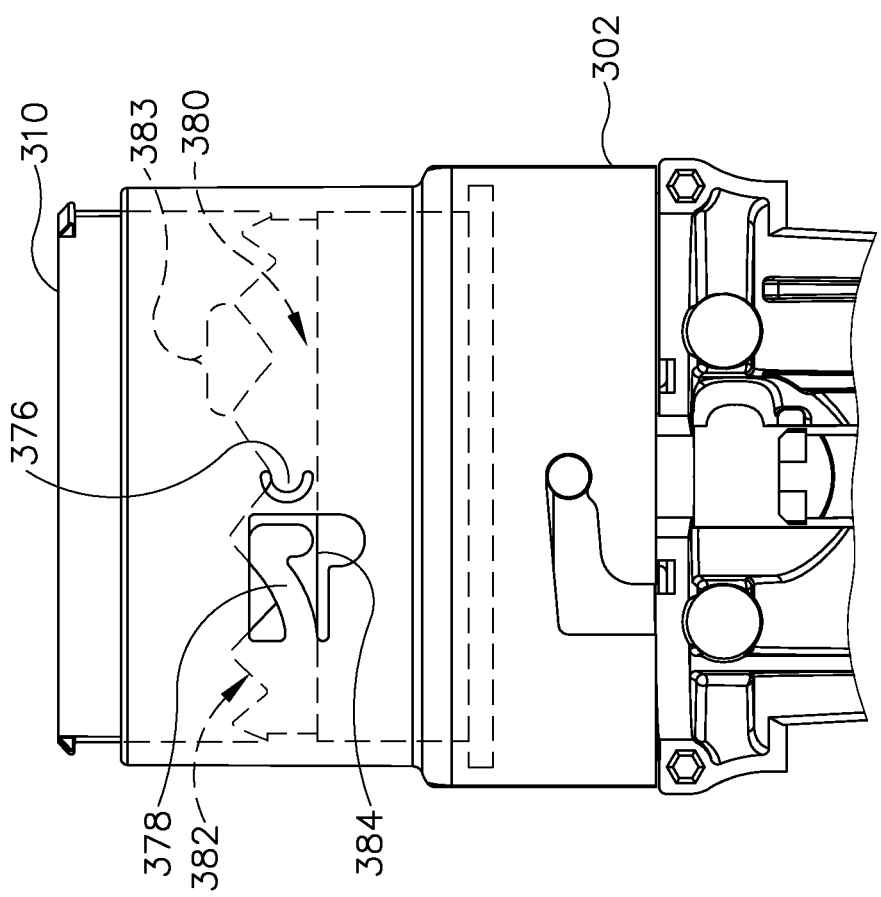
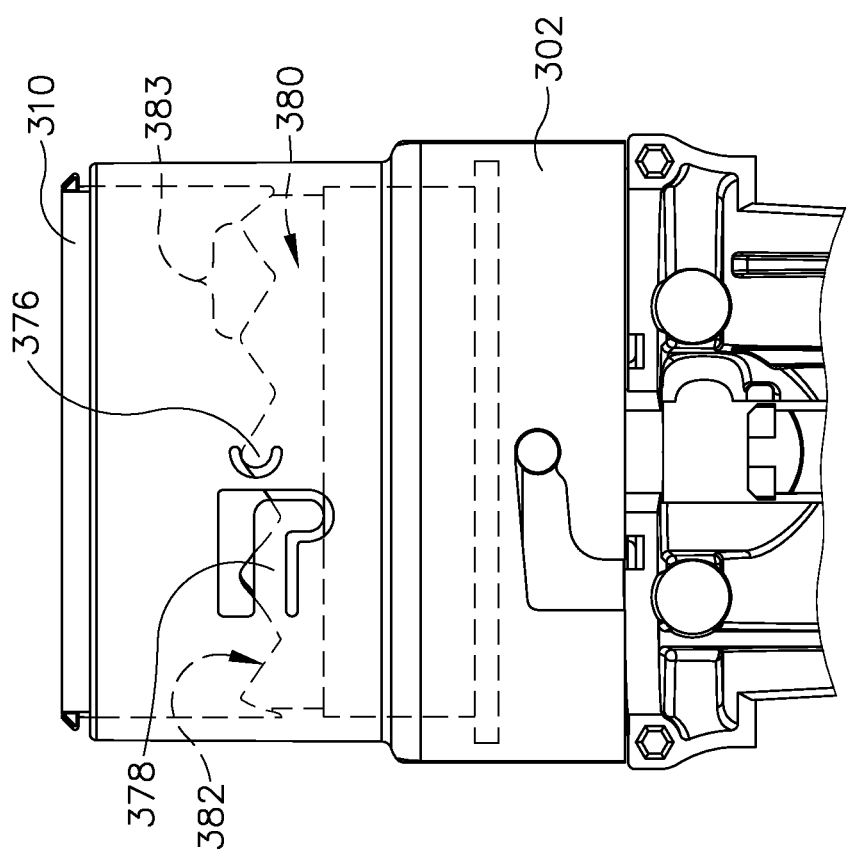

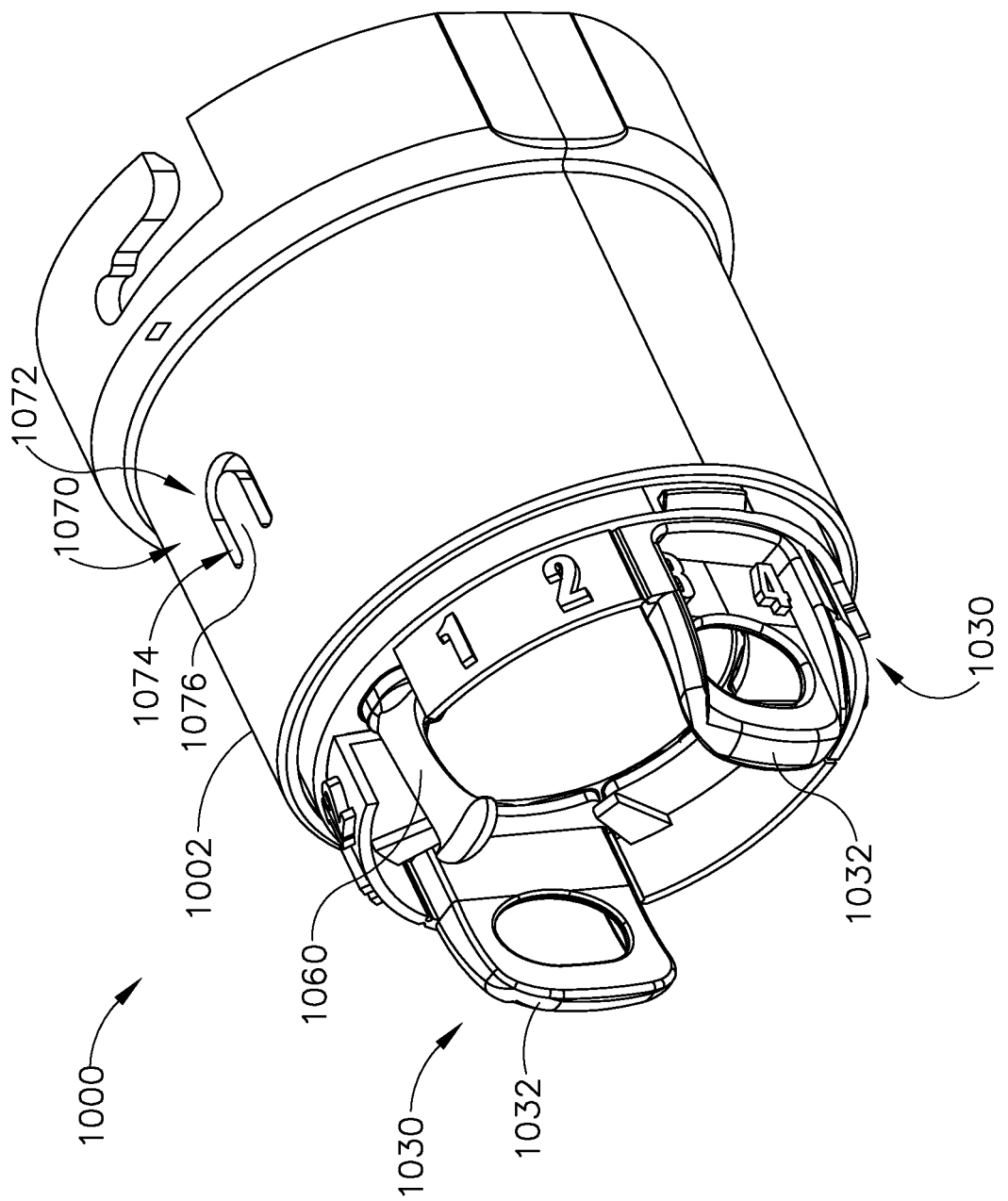

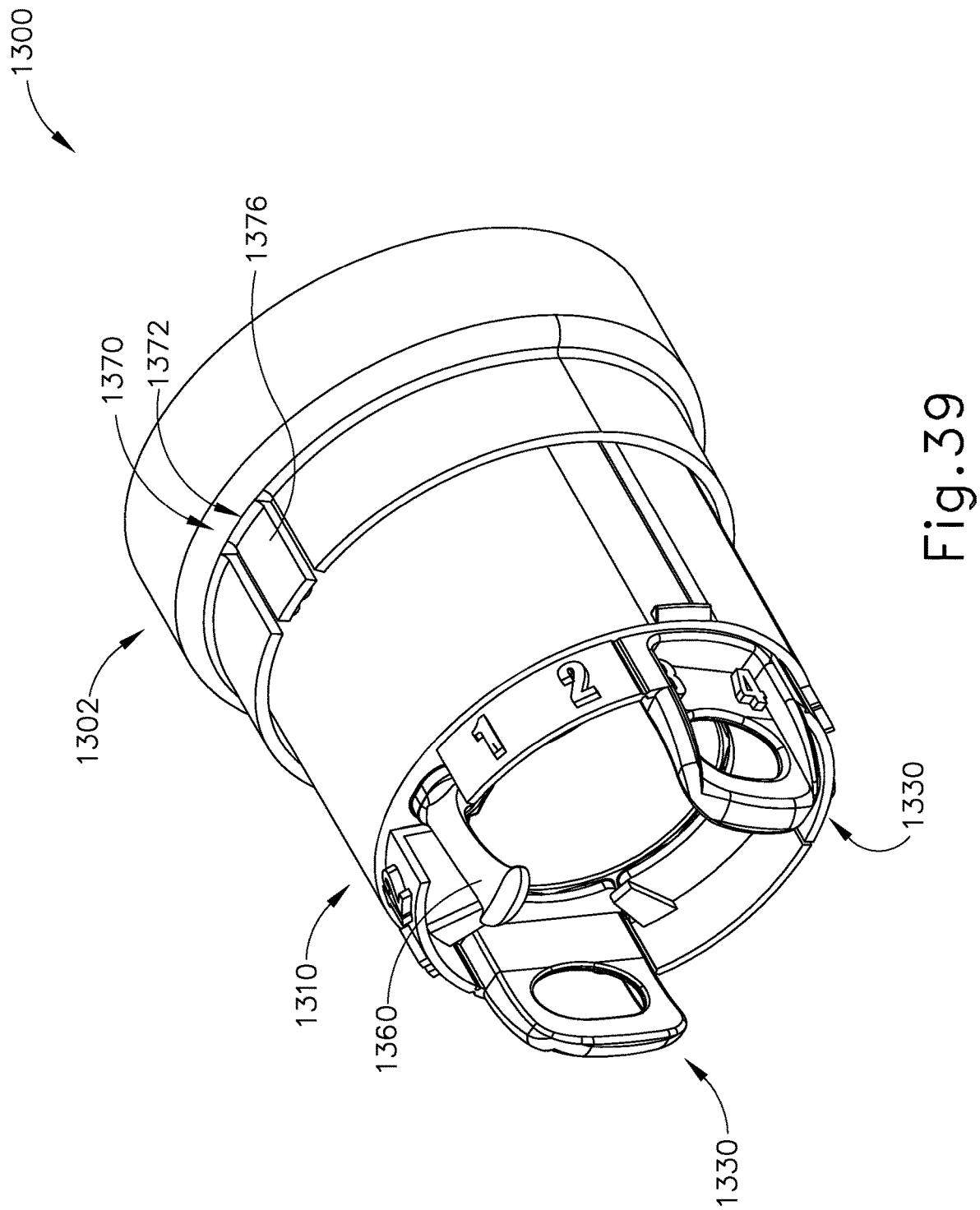

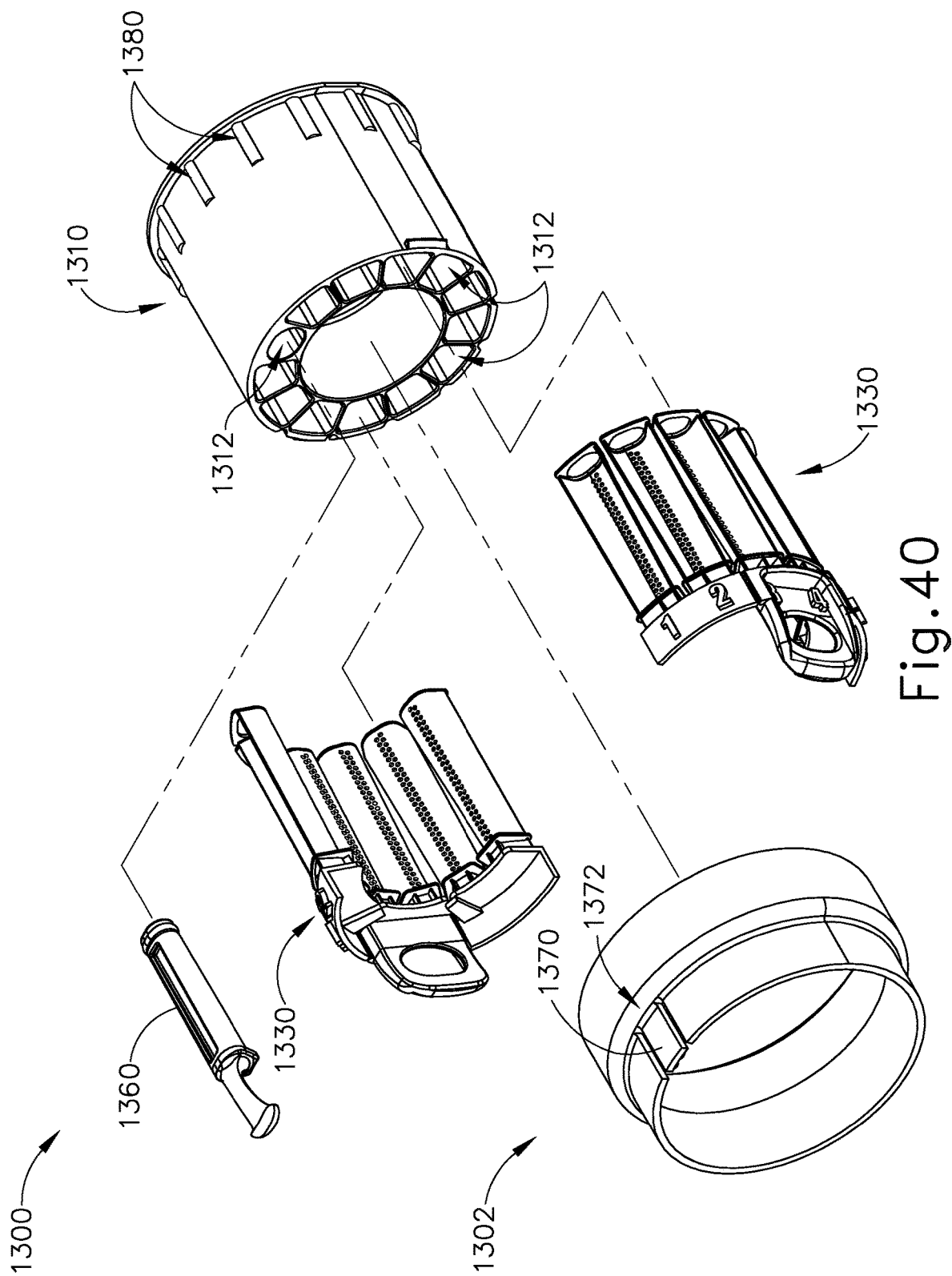

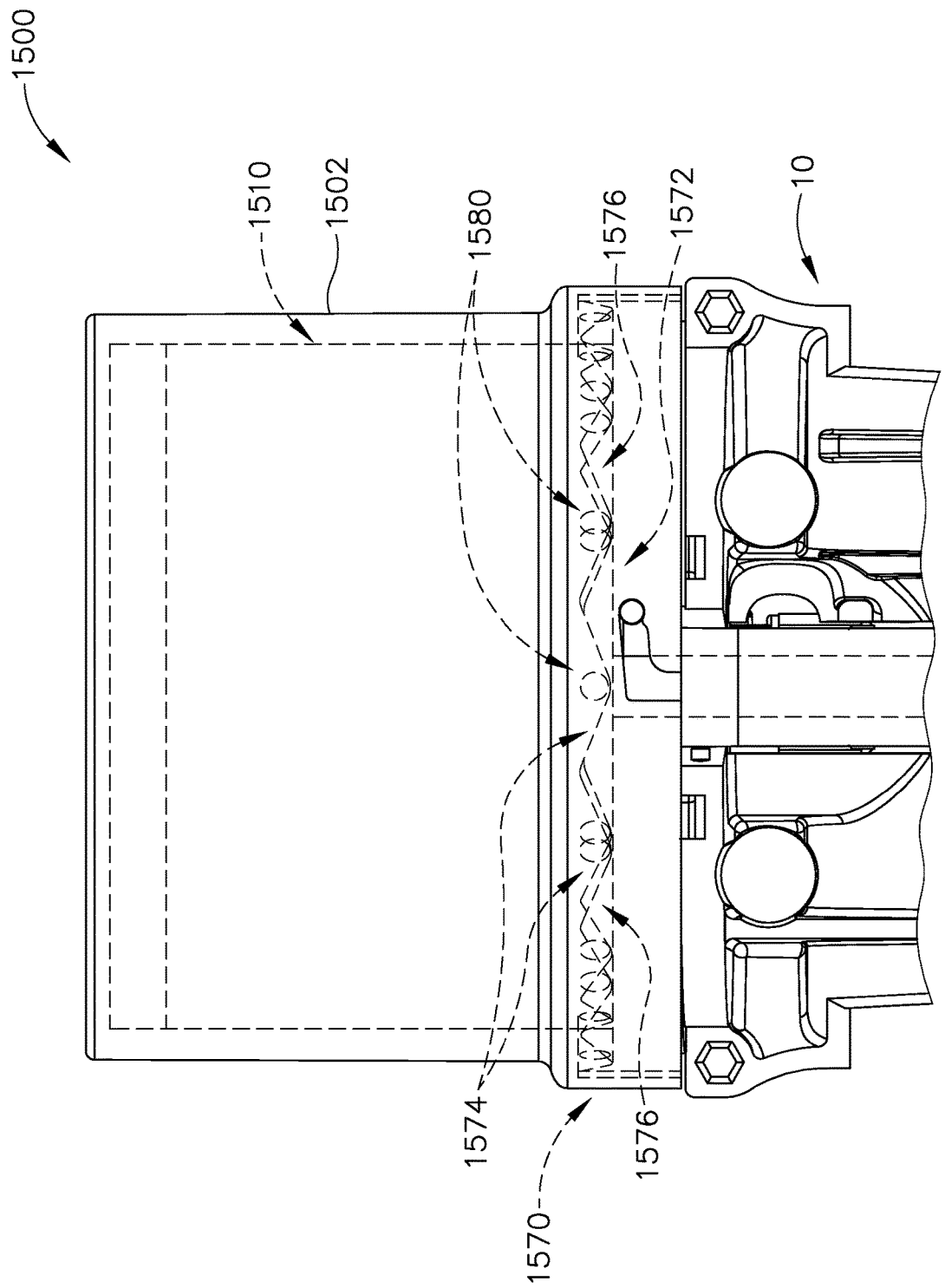

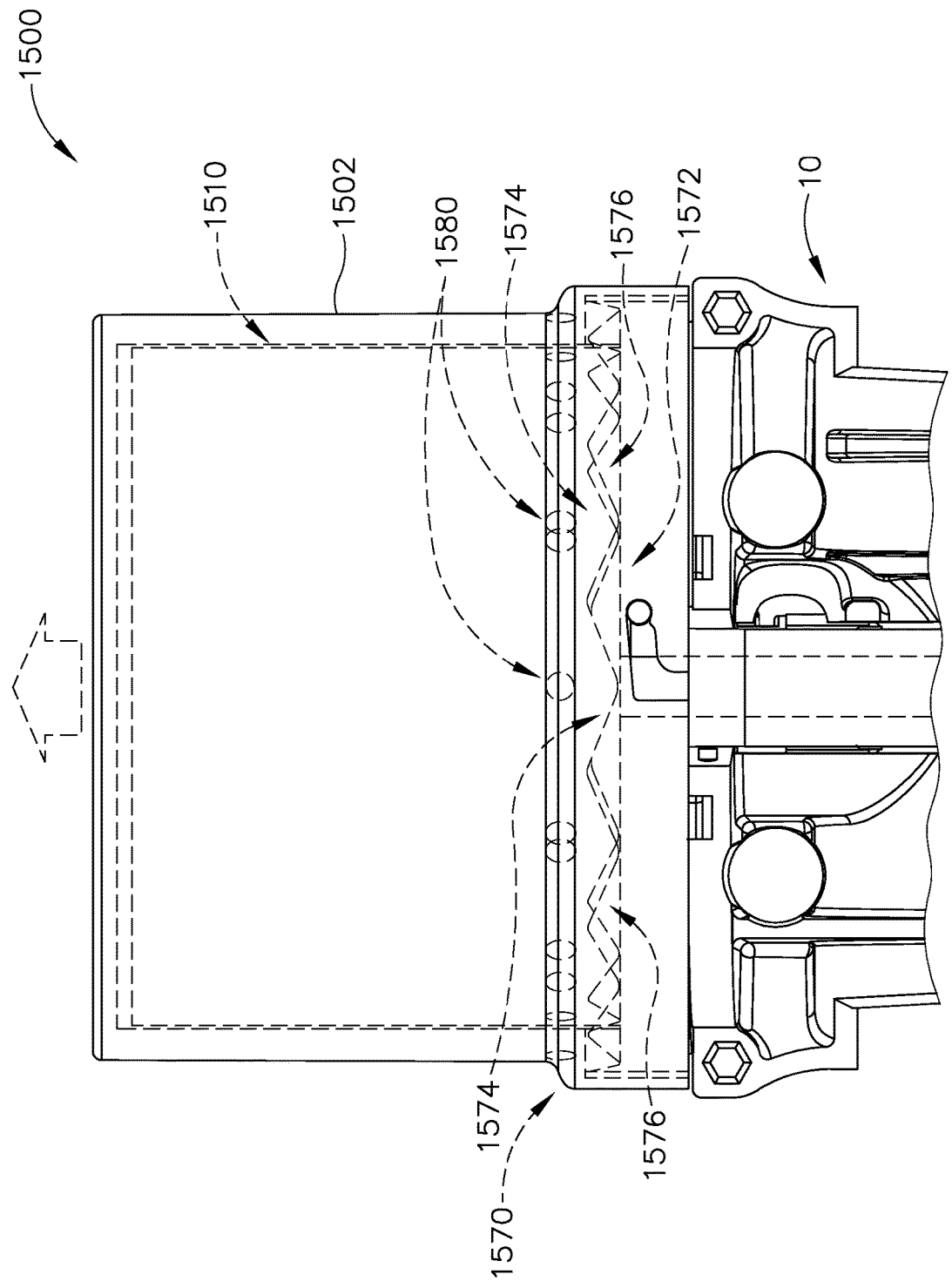

BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006; U.S. Pat. Pub. No. 2008/0146962, entitled "Biopsy System with Vacuum Control Module," published Jun. 19, 2008; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008; U.S. Pat. Pub. No. 2009/0131821, entitled "Graphical User Interface For Biopsy System Control Module," published May 21, 2009; U.S. Pat. Pub. No. 2009/0131820, entitled "Icon-Based User Interface on Biopsy System Control Module," published May 21, 2009; U.S. Pat. Pub. No. 2009/0216152, entitled "Needle Tip for Biopsy Device," published Aug. 27, 2009; U.S. Pat. Pub. No. 2010/0113973, entitled "Biopsy Device with Rotatable Tissue Sample Holder," published May 6, 2010; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0160824, entitled "Biopsy Device with Discrete Tissue Chambers," published Jun. 24, 2010; U.S. Pat. Pub. No. 2010/0317997, entitled "Tetherless Biopsy Device with Reusable Portion," published Dec. 16, 2010; U.S. Pat. Pub. No. 2012/0109007, entitled "Handheld Biopsy Device with Needle Firing," published May 3, 2012; U.S. Pat. Pub. No. 2012/0265095, entitled "Biopsy Device with Motorized Needle Firing," published Oct. 18, 2012; U.S. Pat. Pub. No. 2012/0283563, entitled "Biopsy Device with Manifold Alignment Feature and Tissue Sensor," published Nov. 8, 2012; U.S. Pat. Pub. No. 2012/0310110, entitled "Needle Assembly and Blade Assembly for Biopsy Device," published Dec. 6, 2012; U.S. Pat. Pub. No. 2013/0041256, entitled "Access Chamber and Markers for Biopsy Device," published Feb. 14, 2013; U.S. Pat. Pub. No. 2013/0053724, entitled "Biopsy Device Tissue Sample Holder with Bulk Chamber and Pathology Chamber," published Feb. 28, 2013; U.S. Pub. No. 2013/0144188, entitled "Biopsy Device With Slide-In Probe," published Jun. 6, 2013; U.S. Pub. No. 2013/0324882, entitled "Control for Biopsy Device," published Dec. 5, 2013; U.S. Pub. No. 2013/0218047, entitled "Biopsy Device Valve Assembly," published Aug. 22, 2013; and U.S. Pub. No. 2014/0039343, entitled "Biopsy System," published Feb. 6, 2014. The disclosure of each of the above-cited U.S. patent application Publications, U.S. Non-Provisional patent applications, and U.S. Provisional patent applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, and CORMARK™ brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. patents and U.S. patent application Publications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 18 depicts a perspective view of a transparent cover of the tissue sample holder assembly of FIG. 9;

FIG. 19 depicts a perspective cross-sectional view of the transparent cover of FIG. 18 with the cross-section taken along line 19-19 of FIG. 18;

FIG. 20A depicts a partial top view of the tissue sample holder assembly of FIG. 9 with the tissue sample holder in an indexed position;

FIG. 20B depicts a partial top view of the tissue sample holder assembly of FIG. 9 with the tissue sample holder in an advanced position;

FIG. 21 depicts a perspective view of another tissue sample holder for incorporation into the probe of FIG. 4;

FIG. 39 depicts a perspective view of yet another tissue sample holder for incorporation into the probe of FIG. 4;

FIG. 40 depicts a perspective exploded view of the tissue sample holder of FIG. 39;

FIG. 55 depicts top plan view of the tissue sample holder of FIG. 52 with the manifold in an indexed position; and FIG. 56 depicts a top plan view of the tissue sample holder of FIG. 52 with the manifold in an un-indexed position.

Figure 1:
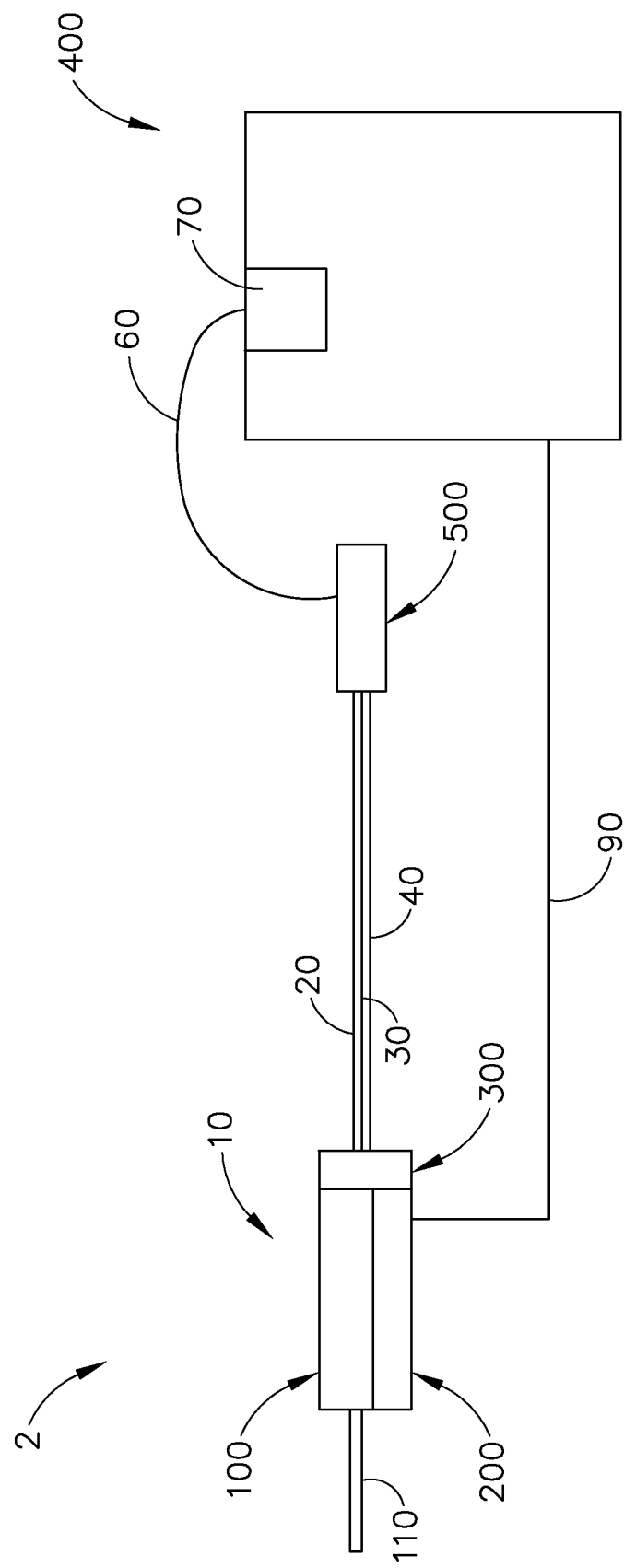
FIG. 1 depicts a schematic view of an exemplary biopsy system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. OVERVIEW OF EXEMPLARY BIOPSY SYSTEM

Figure 2:
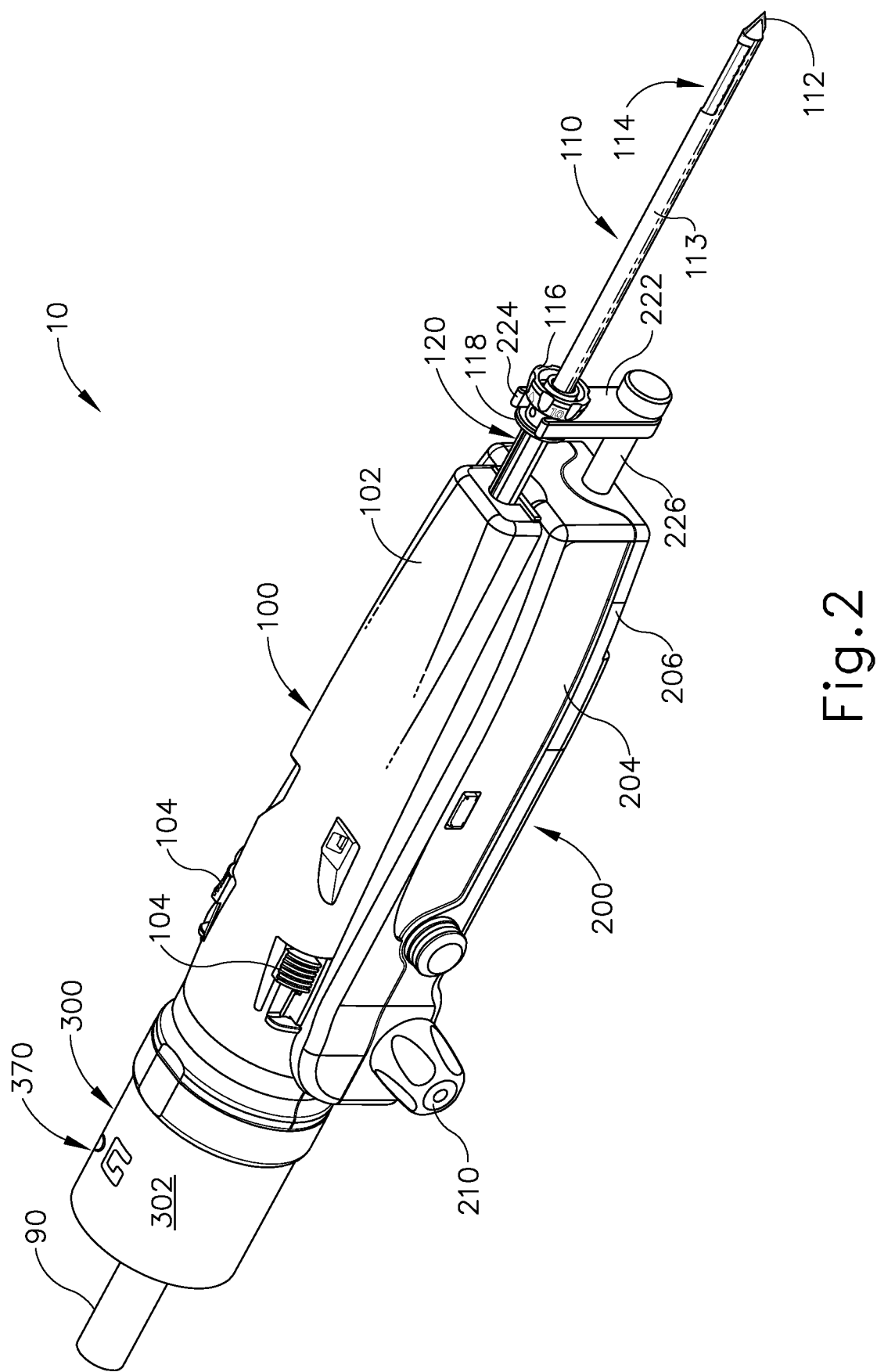
FIG. 2 depicts a perspective view of an exemplary biopsy device of the biopsy system of FIG. 1, including an exemplary probe coupled with an exemplary holster.
Figure 3:
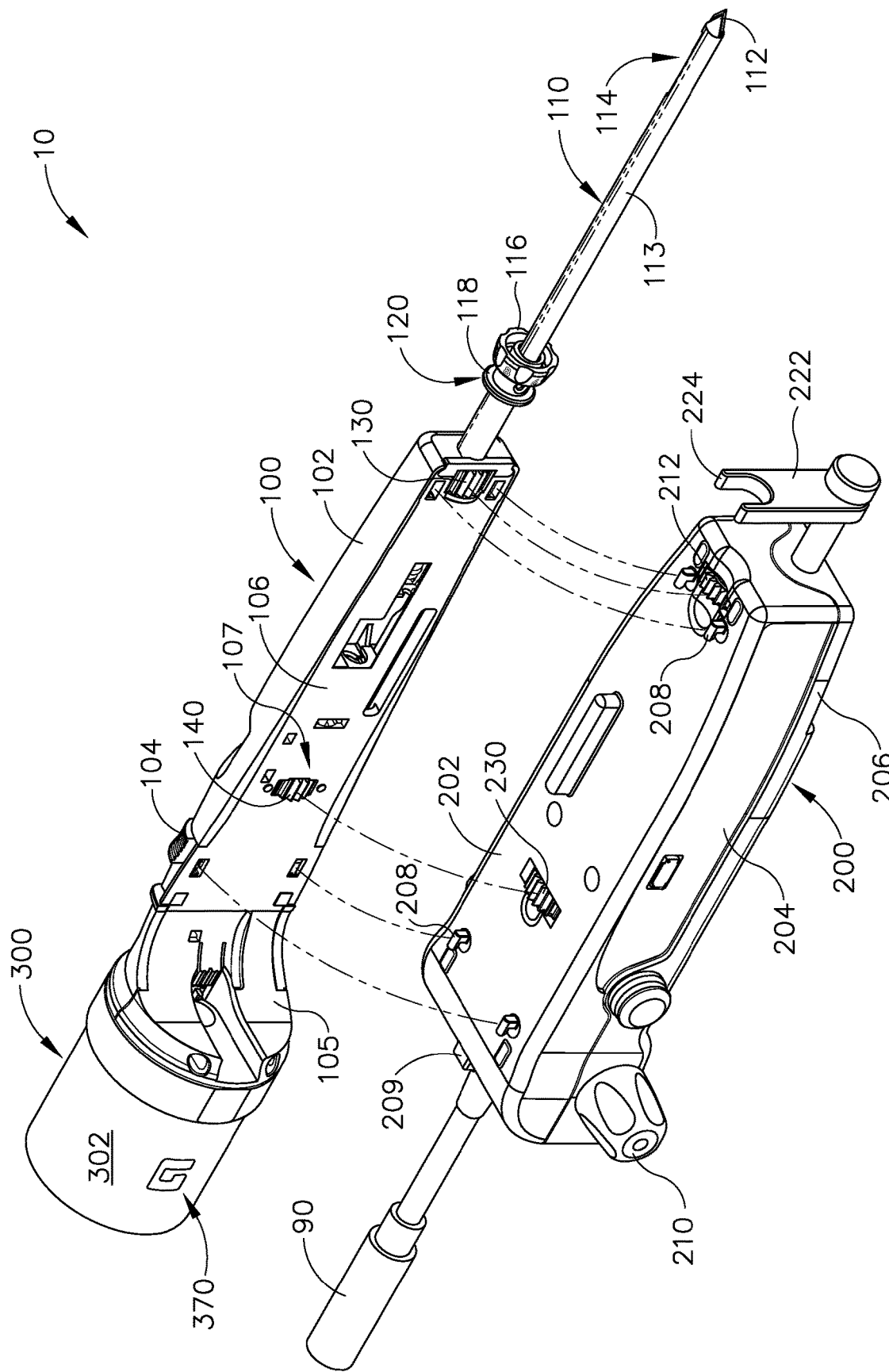
FIG. 3 depicts a perspective view of the biopsy device of FIG. 2, with the probe decoupled from the holster.

FIG. 1 depicts an exemplary biopsy system (2) comprising a biopsy device (10) and a vacuum control module (400). Biopsy device (10) of this example comprises a probe (100) and a holster (200), as shown in FIGS. 2-3. A needle (110) extends distally from probe (100), and is inserted into a patient's tissue to obtain tissue samples. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. EXEMPLARY HOLSTER

As shown in FIG. 3, holster (200) of the present example includes a top housing cover (202), side panels (204), and a housing base (206), which are fixedly secured together. Gears (212, 230) are exposed through top housing cover (202), and mesh with gears (130, 140) of probe (100) when probe (100) and holster (200) are coupled together. In particular, gears (230, 140) drive the actuation assembly of a cutter (150) (see, FIG. 5) within needle (110); while gears (212, 130) are employed to rotate needle (110). A gear (not shown) located at the proximal end of holster (200), meshes with gear (182) of probe (100) to rotate a manifold (310) of tissue sample holder (300).

As noted above, rotation of gear (212) provides rotation of needle (110) relative to probe (100). In the present example, gear (212) is rotated by rotating knob (210). In particular, knob (210) is coupled with gear (212) by a series of gears (not shown) and shafts (not shown), such that rotation of knob (210) rotates gear (212). A second knob (210) extends from the other side of holster (200). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which is incorporated by reference herein. In some other versions, needle (110) is rotated by a motor. In still other versions, needle (110) is simply rotated by rotating a thumbwheel (116). Various other suitable ways in which rotation of needle (110) may be provided will be apparent to those of ordinary skill in the art in view of the teachings herein. It should also be understood that some versions may provide no rotation of needle (110).

Holster (200) also includes a firing rod (226) and fork (222), which couple with needle (110) and fire needle (110) distally. By way of example only, such firing may be useful in instances where biopsy device (10) is mounted to a stereotactic table fixture or other fixture, with a tissue piercing tip (112) adjacent to a patient's breast, such that the needle firing mechanism may be activated to drive needle (110) into the patient's breast. The needle firing mechanism may be configured to drive needle (110) along any suitable range of motion, to drive tip (112) to any suitable distance relative to fixed components of probe (100).

In the present example, the needle firing mechanism is coupled with needle (110) via a firing rod (226) and a firing fork (222). Firing rod (226) and firing fork (222) are unitarily secured together. Firing fork (222) includes a pair of prongs (224) that receive hub member (120) of needle (110) therebetween. Prongs (224) are positioned between an annular flange (118) and thumbwheel (116), such that needle (110) will translate unitarily with firing rod (226) and fork (222). Prongs (224) nevertheless removably receive hub member (120), such that fork (222) may be readily secured to hub member (120) when probe (100) is coupled with holster (200); and such that hub member (120) may be readily removed from fork (222) when probe (100) is decoupled from holster (200). Prongs (224) are also configured to permit hub member (120) to rotate between prongs (224). Other suitable components, configurations, and relationships will be apparent to those of ordinary skill in the art in view of the teachings herein. The internal components of the needle firing mechanism of the present example are configured and arranged as described in U.S. Pat. No. 8,858,465, entitled "Biopsy Device with Motorized Needle Firing," issued Oct. 14, 2014, the disclosure of which is incorporated by reference herein.

Holster (200) includes motors (not shown) to drive gear (230) and the gear (not shown) on the proximal end of holster (200) to thereby rotate and translate cutter (150) and rotate manifold (310) of tissue sample holder (300). Holster (200) also includes a motor (not shown) that is operable to drive firing rod (226), to thereby arm and fire needle (110). All motors referred to herein are contained within holster (200) in the present example and receive power from vacuum control module (400) via cable (90). In addition, data may be communicated between vacuum control module (400) and holster (200) via cable (90). In some other versions, one or more motors are powered by one or more batteries located within holster (200) and/or probe (100). It should therefore be understood that, as with other components described herein, cable (90) is merely optional. As yet another merely illustrative variation, motors may be powered pneumatically, such that cable (90) may be substituted with a conduit communicating a pressurized fluid medium to holster (200). As still other merely illustrative variation, cable (90) may include one or more rotary drive cables that are driven by motors that are located external to holster (200). It should also be understood that two or three of the motors may be combined as a single motor. Other suitable ways in which various the motors may be driven will be apparent to those of ordinary skill in the art in view of the teachings herein.

III. EXEMPLARY PROBE

Probe (100) of the present example includes a needle (110) extending distally from probe (100) that is inserted into a patient's tissue to obtain tissue samples. These tissue samples are deposited in a tissue sample holder (300) at the proximal end of probe (100). As shown in FIG. 1, vacuum control module (400) is coupled with probe (100) via a valve assembly (500) and tubes (20, 30, 40, 60), which is operable to selectively provide vacuum, saline, atmospheric air, and venting to probe (100). The internal components of the valve assembly of the present example are configured and arranged as described in U.S. Pub. No. 2013/0218047, entitled "Biopsy Device Valve Assembly," published Aug. 22, 2013, the disclosure of which is incorporated by reference herein.

As shown in FIGS. 1-6, probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together. Similarly, gear (130) of probe (100) meshes with exposed gear (212) of holster (200) when probe (100) and holster (200) are coupled together.

A. Exemplary Needle Assembly

Needle (110) of the present example comprises a cannula (113) having a tissue piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," issued Aug. 12, 2014, the disclosure of which is incorporated by reference herein. As another merely illustrative example, tip (112) may be configured in accordance with at least some of the teachings in U.S. Pub. No. 2013/0144188, entitled "Biopsy Device with Slide-In Probe," filed Published 6, 2013, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to prolapse therethrough; then from the retracted position back to the extended position to sever the prolaped tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
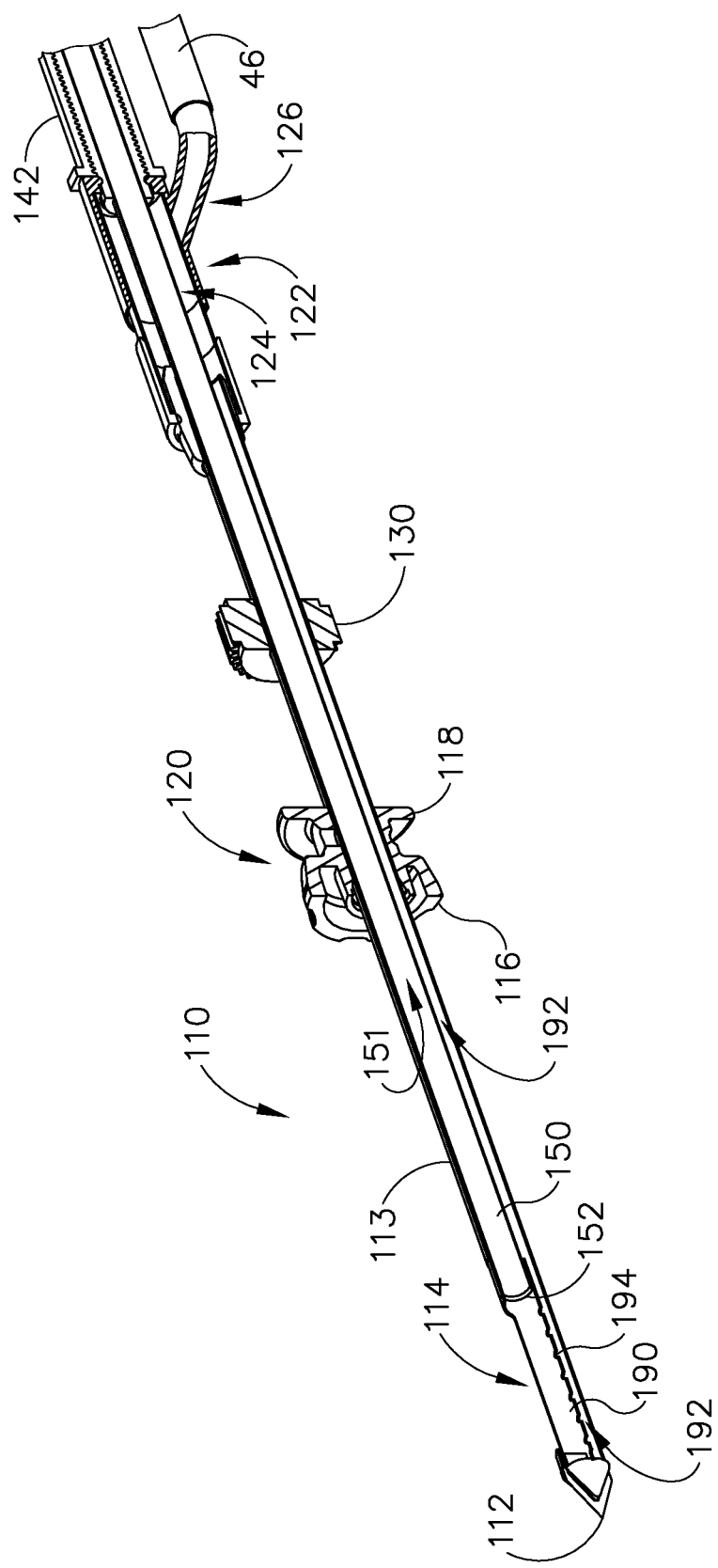
FIG. 6 depicts a cross-sectional view of a needle assembly of the probe of FIG. 4.

As best seen in FIG. 6, needle (110) also includes a longitudinal wall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

A plurality of external openings (not shown) may also be formed in needle (110), and may be in fluid communication with second lumen (192). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings in needle (110) are merely optional.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion (150) of hub member (120) and is keyed to hub member (120), such that rotation of gear (130) will rotate hub member (120) and needle (110); yet hub member (120) and needle (110) may translate relative to gear (130). Gear (130) is rotatably driven by gear (212). Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein.

As shown in FIGS. 4-7, a manifold (122) is provided at the proximal end of needle (110). Manifold (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that manifold (122) provides fluid communication between second lumen (192) and tube (46). Manifold (122) also seals against the exterior of needle (110) such that manifold (122) provides a fluid tight coupling between second lumen (192) and tube (46) even if needle (110) is translated and/or rotated relative to manifold (122), such as during firing of needle (110) or re-orientation of needle (110), respectively.

Figure 4:
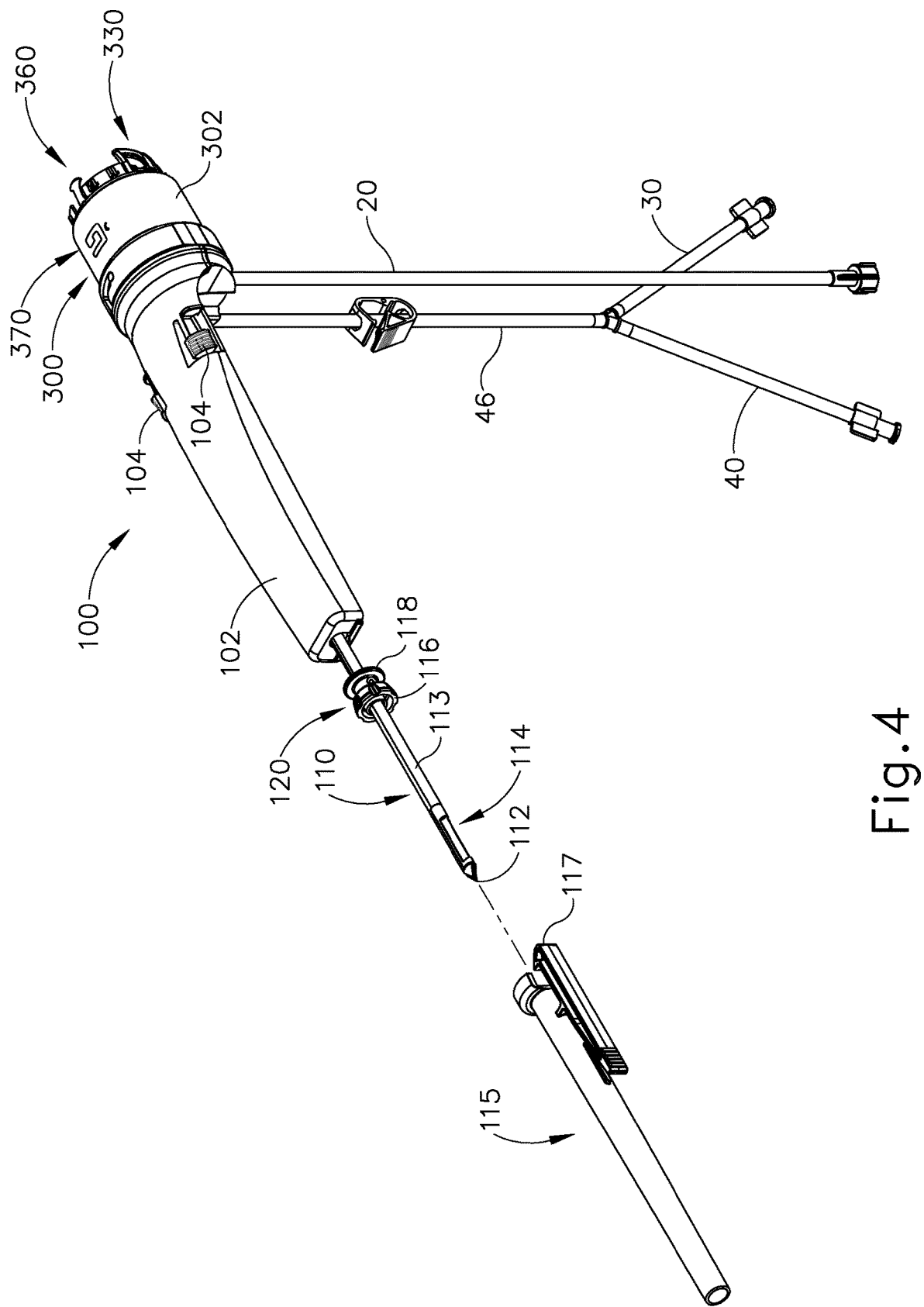
FIG. 4 depicts a perspective view of the probe of the biopsy device of FIG. 2.

As shown in FIG. 4, needle (110) may be provided with a removable cover (115). Cover (115) of this example includes a resiliently biased latch (117) that is configured to engage thumbwheel (116), to thereby removably secure cover (115) to needle (110). Cover (115) is configured to cover tip (112) when latch (117) is engaged with thumbwheel (116), such that cover (115) protects the user of biopsy device (10) from inadvertent contact with tip (112). Cover (115) may also include one or more wiper seals near the proximal end and/or distal end of cover (115), to seal against cannula (113). By way of example only, cover (115) may be configured in accordance with at least some of the teachings in U.S. Provisional Pat. App. No. 61/566,793, the disclosure of which is incorporated by reference herein. Various other suitable configurations for cover (115) will be apparent to those of ordinary skill in the art in view of the teachings herein. Of course, cover (115) may simply be omitted if desired. It should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pub. No. 2008/0214955, the disclosure of which is incorporated by reference herein, and/or in accordance with the teachings of any other reference cited herein.

B. Exemplary Cutter Assembly

Figure 5:
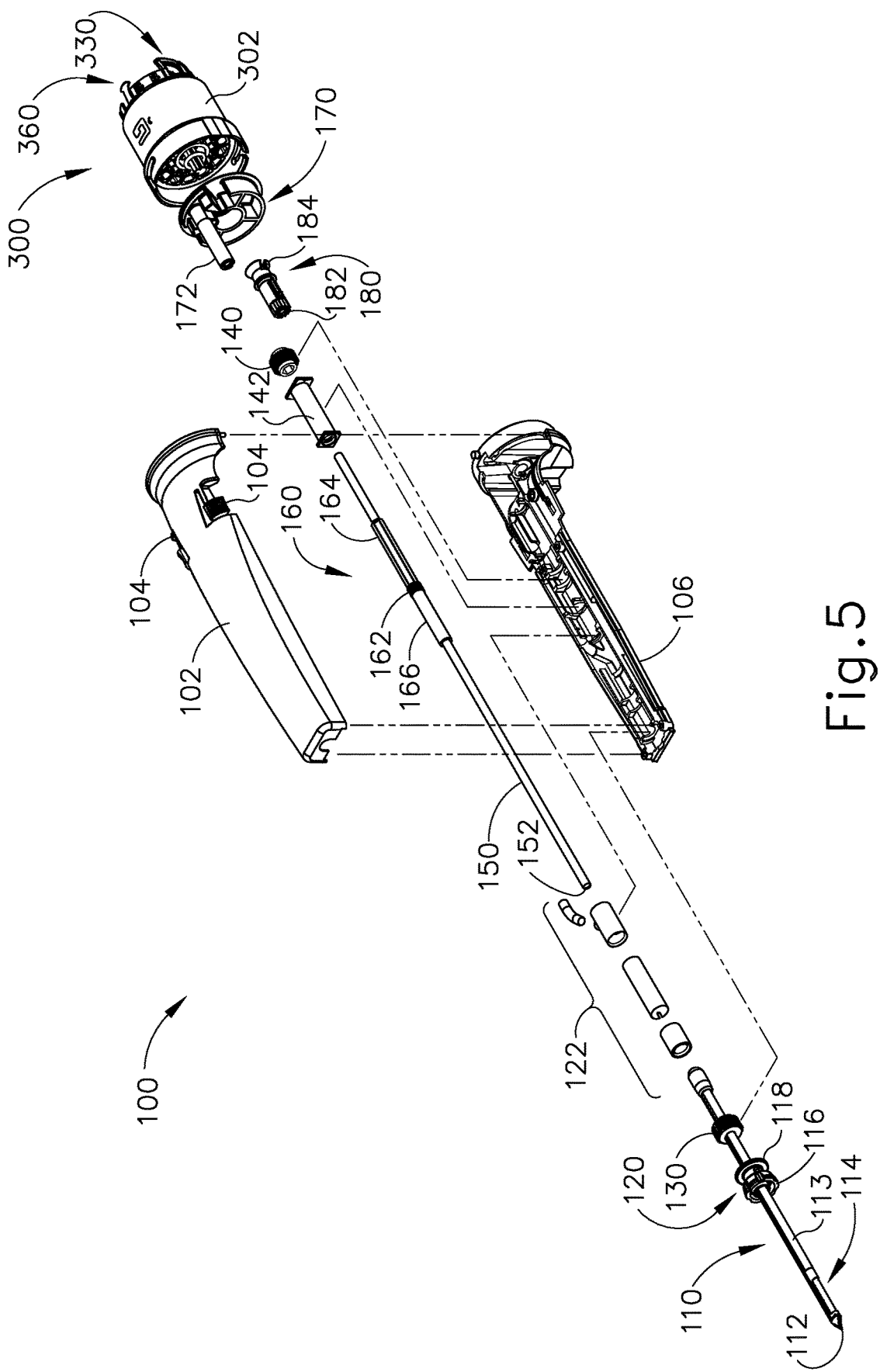
FIG. 5 depicts an exploded view of the probe of FIG. 4.
Figure 7:
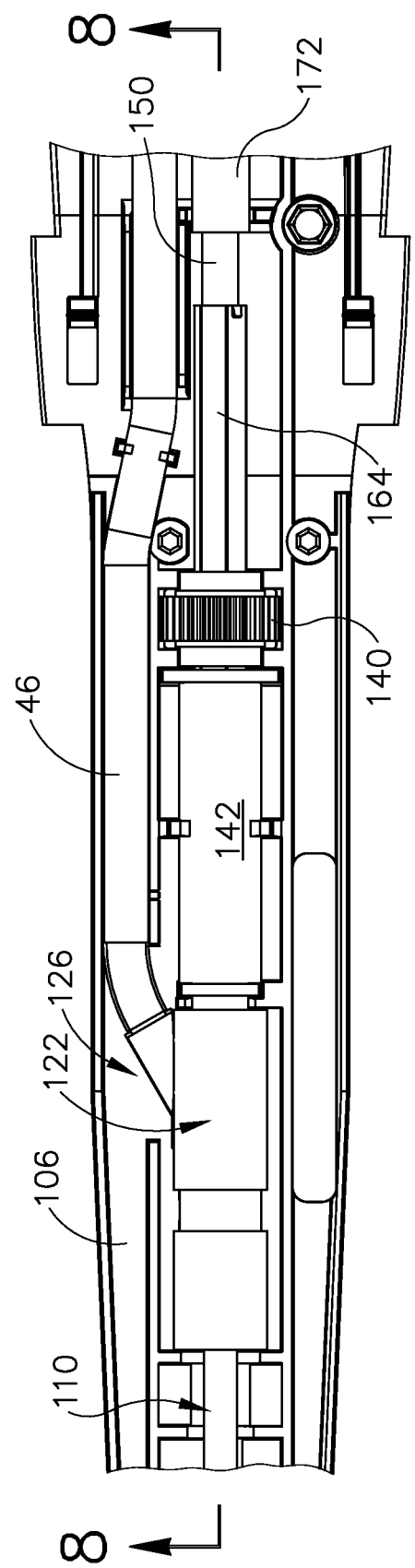
FIG. 7 depicts a partial top plan view of components of the probe of FIG. 4, with a top housing piece removed.

As noted above, cutter (150) is operable to simultaneously translate and rotate relative to needle (110) to sever a tissue sample from tissue protruding through lateral aperture (114). As best seen in FIGS. 5-7 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into manifold (122). Manifold (122) seals against distal portion (166) such that manifold (122) maintains the fluid tight coupling between second lumen (192) and tube (46) even when cutter (150) is translated and rotated relative to manifold (122).

Figure 8:
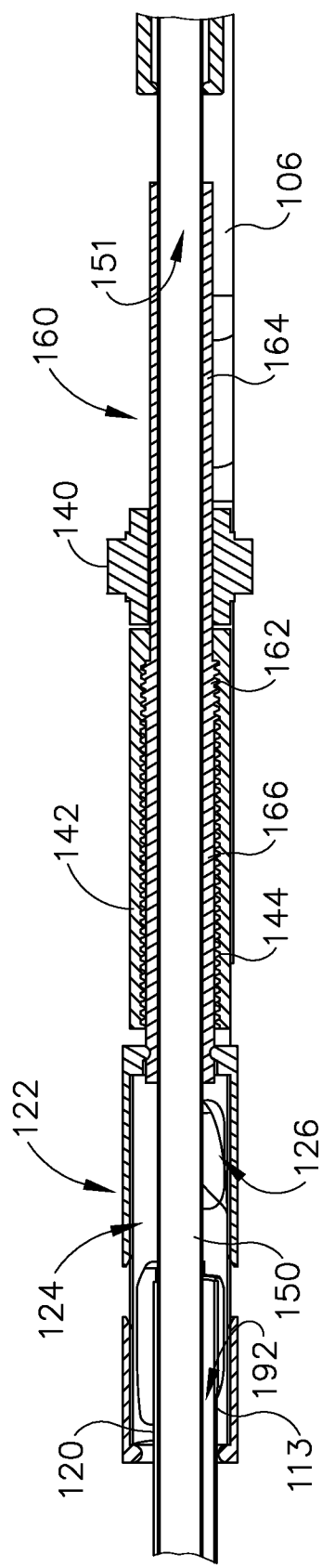
FIG. 8 depicts a side cross-sectional view of the components of FIG. 7, taken along line 8-8 of FIG. 7.

A gear (140) is positioned on flats (164) and includes a set of internal flats (not shown) that complement flats (164). Thus, gear (140) rotates overmold (160) and cutter (150) when gear (140) is rotated. However, overmold (160) is slidable relative to gear (140), such that cutter (150) may translate relative to chassis (106) despite gear (140) being longitudinally fixed relative to chassis (106). Gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (106). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pat. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

C. Exemplary Tissue Sample Holder Assembly

Tissue sample holder (300) of the present example provides a plurality of discrete chambers that are configured to receive tissue samples that are severed by cutter (150) and communicated proximally through lumen (151) of cutter (150). In particular, and as will be described in greater detail below, tissue sample holder (300) includes tissue receiving trays (330) that are removably engaged with a manifold (310). Manifold (310) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with the gear (not shown) on the proximal end of holster (200) when probe (not shown) and holster (200) are coupled together. Gear (182) of probe (100) and the gear (not shown) on the proximal end of holster (200) cooperate to rotate manifold (310) to index tissue chambers relative to lumen (151) of cutter (150) as will be described in greater detail below. A transparent cover (302) is positioned about manifold (310) and is removably secured to chassis (106). While bayonet features provide coupling between cover (302) and chassis (106), it should be understood that any suitable type of coupling may be used. Manifold (310) is freely rotatable within cover (302). However, manifold (310) is engaged with cover (302) such that manifold (310) will decouple relative to chassis (106) when cover (302) is removed from chassis (106). In other words, manifold (310) may be selectively coupled with and removed relative to chassis (106) by coupling and removing cover (302) from chassis (106).

1. Exemplary Manifold

Figure 12:
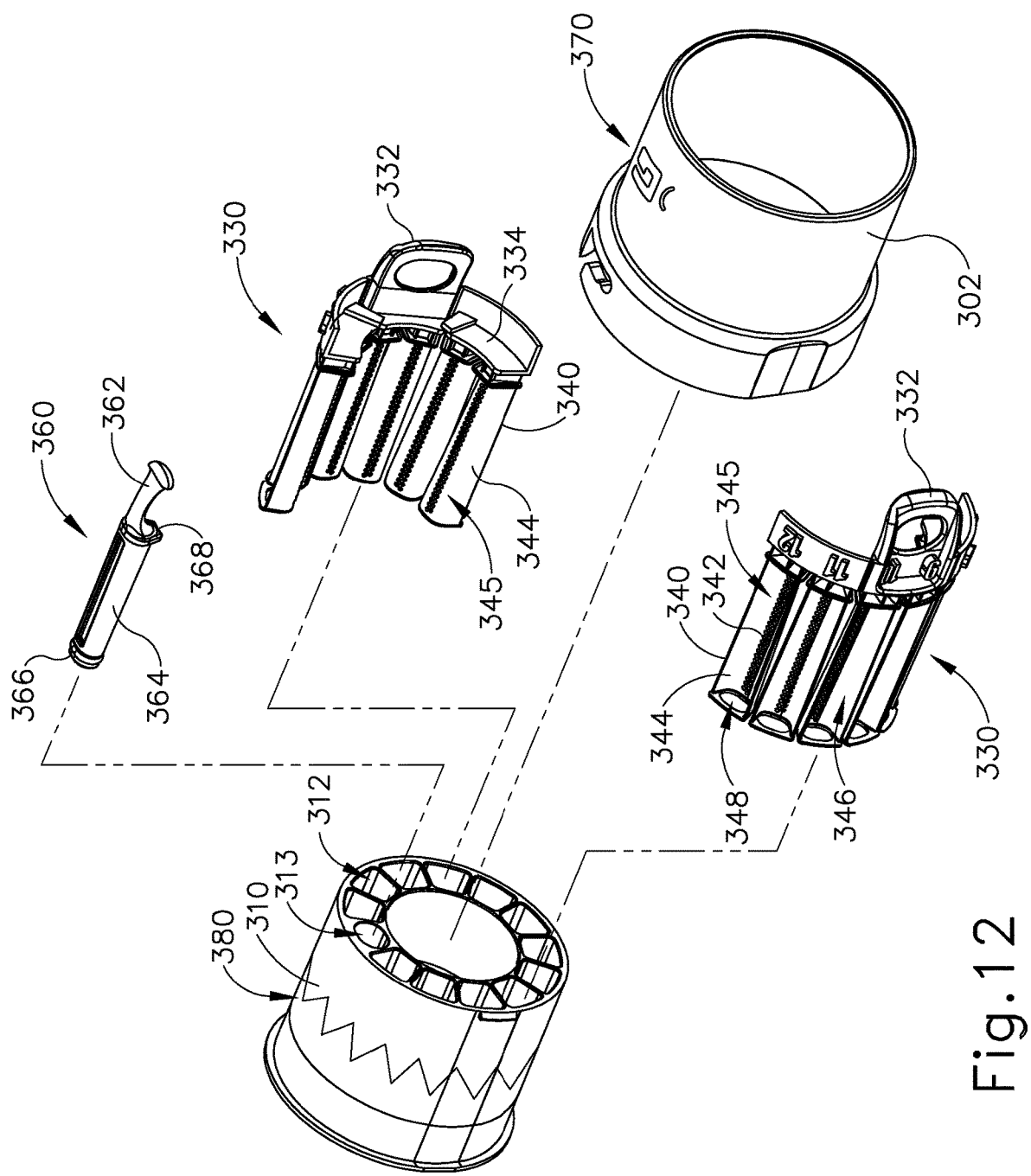
FIG. 12 depicts an exploded view of components of rotatable components of the tissue sample holder assembly of FIG. 9.
Figure 13:
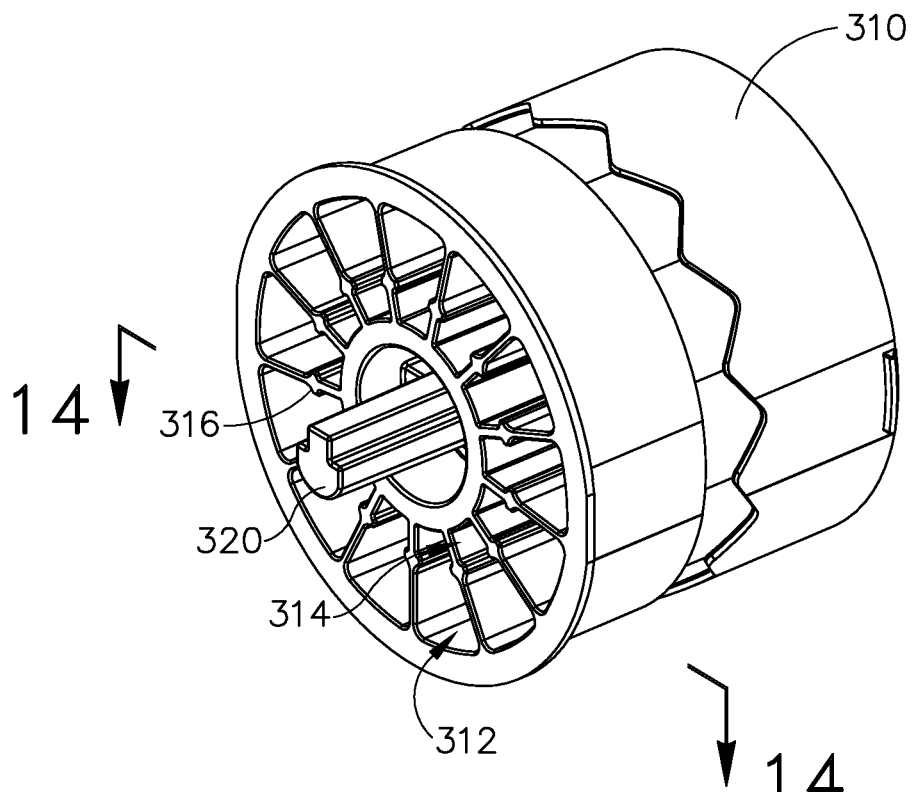
FIG. 13 depicts a perspective view of a rotatable manifold of the tissue sample holder assembly of FIG. 9.
Figure 14:
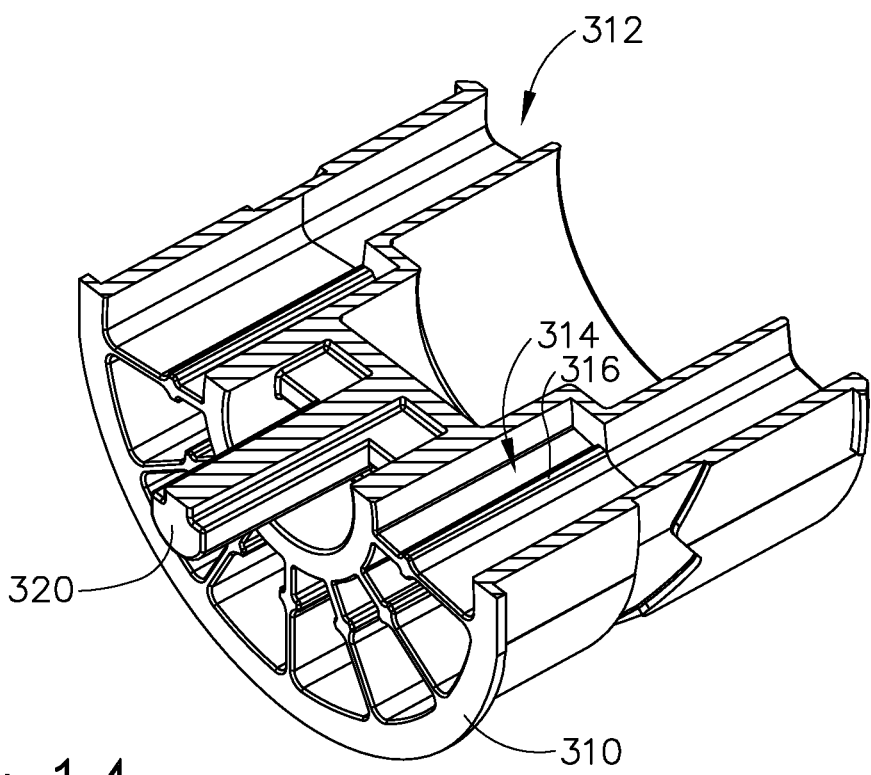
FIG. 14 depicts a cross-sectional view of the manifold of FIG. 13, taken along line 14-14 of FIG. 13.

As best seen in FIGS. 12-14, manifold (310) of the present example defines a plurality of chambers in the form of passages (312) that extend longitudinally through manifold (310) and that are angularly arrayed about the central axis of manifold (310). As best seen in FIG. 14, a lateral recess (314) is associated with a distal portion of each passage (312). Shelves (316) demarcate boundaries between each passage (312) and the associated lateral recess (314). As will be described in greater detail below, passages (312) receive trays (330) while recesses (314) provide pneumatic passages. An additional passage (313) and recess (315) are associated with a plug (360), as will also be described in greater detail below. Manifold (310) also includes a central shaft (320), which is configured to removably engage grasping feature (184). Central shaft (320) couples with grasping feature (184) upon coupling of cover (302) with chassis (106), as described above. Engagement between central shaft (320) and grasping feature (184) provides rotation of manifold (310) upon rotation of gear (182).

Figure 9:
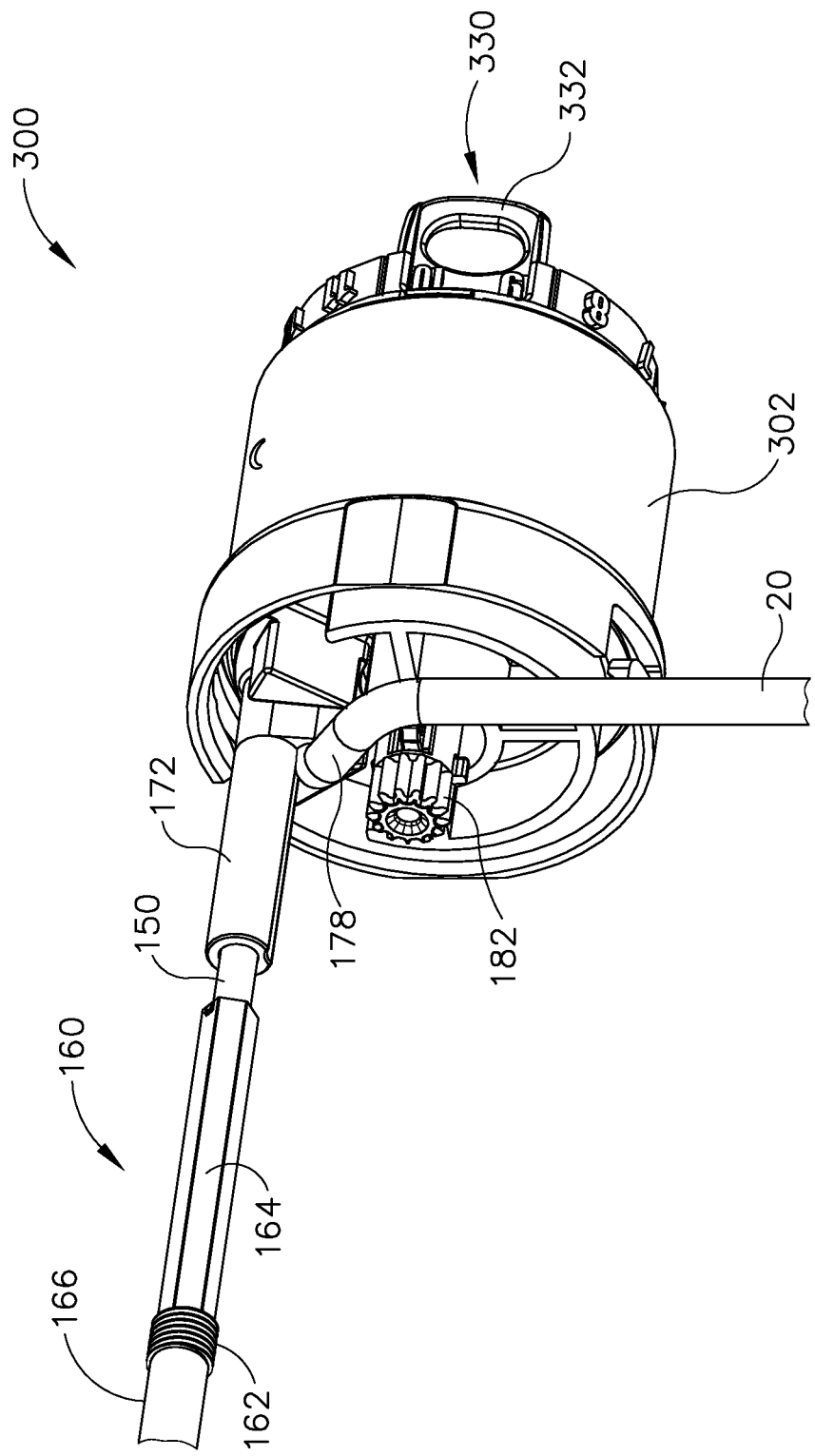
FIG. 9 depicts a perspective view of a tissue sample holder assembly of the probe of FIG. 4.
Figure 10:
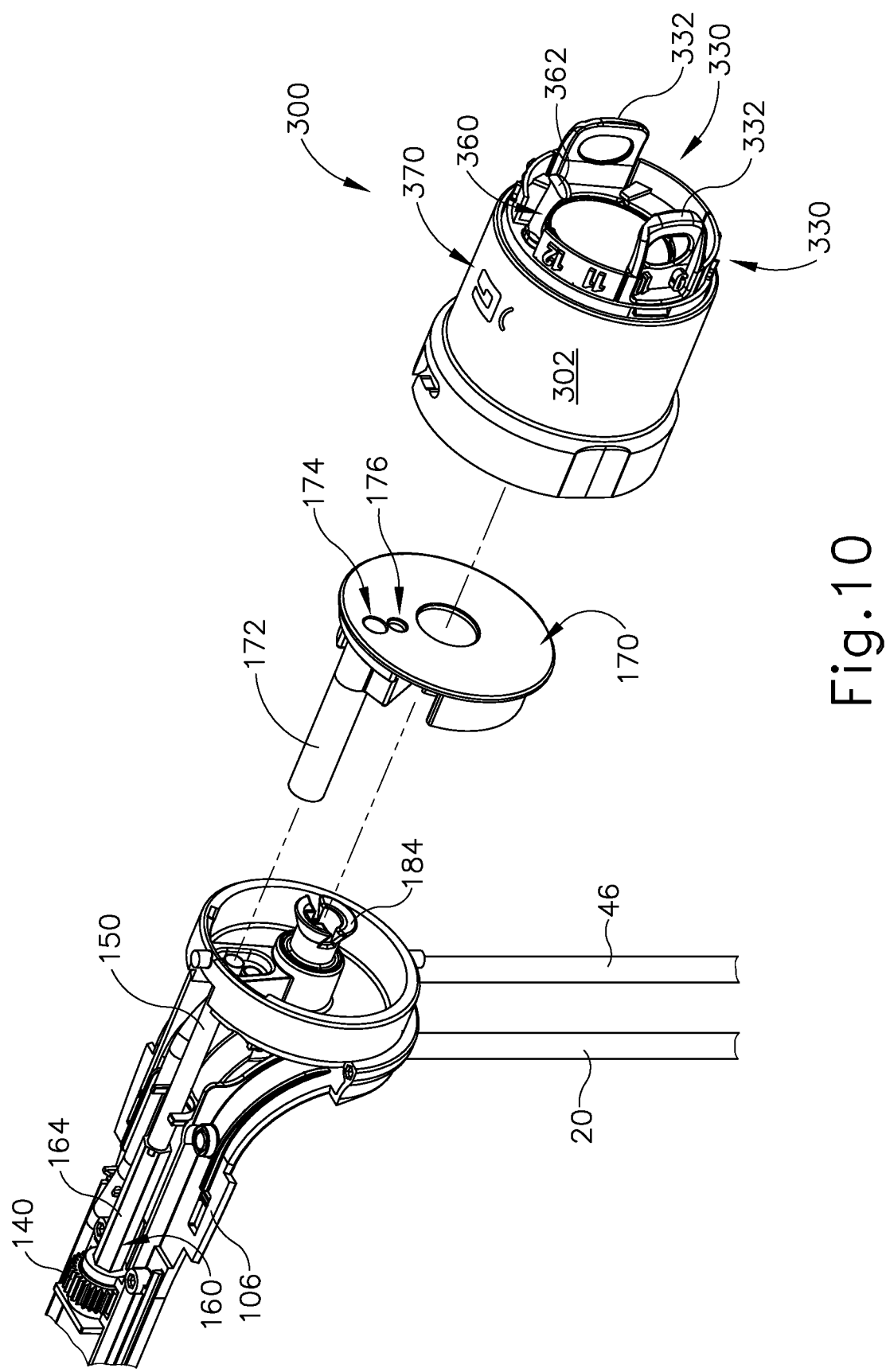
FIG. 10 depicts an exploded view of the tissue sample holder assembly of FIG. 9.
Figure 11:
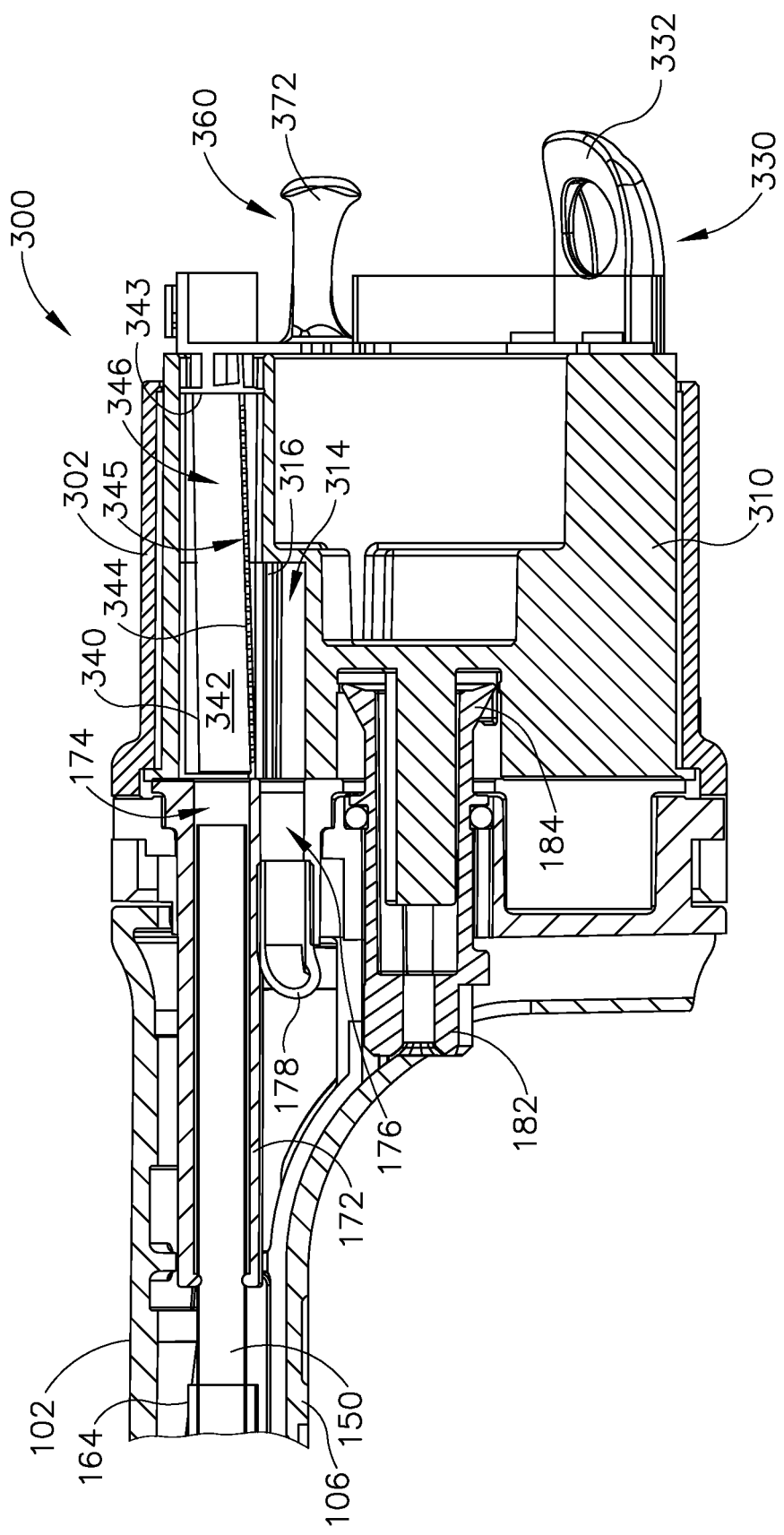
FIG. 11 depicts a side cross-sectional view of the tissue sample holder assembly of FIG. 9, with a tissue sample chamber aligned with the cutter.

As best seen in FIGS. 10-11, a sealing member (170) is provided at the proximal end of chassis (106) and interfaces with the distal face of manifold (310). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of cutter seal (170). This opening (174) is configured to align with whichever passage (312, 313) is at the 12 o'clock position. Another opening (176) is positioned below opening (174). Opening (176) is configured to align with whichever recess (314, 315) is at the 12 o'clock position. As best seen in FIGS. 9 and 11, opening (176) is in fluid communication with a port (178), which is coupled with tube (20). Thus, sealing member (170) provides fluid communication between tube (20) and whichever recess (314, 315) is at the 12 o'clock position. As will be described in greater detail below, manifold (310) further provides fluid communication between such recess (314, 315) and the associated passage (312, 313) at the 12 o'clock position; and thereby further to lumen (151) of cutter (150). In other words, sealing member (170) and manifold (310) cooperatively to provide fluid communication between tube (20) and lumen (151) of cutter (150) via whichever passage (312, 313) and recess (314, 315) are at the 12 o'clock position. It should be understood that sealing member (170) of the present example maintains a fluid tight seal against the distal face of manifold (310), even as manifold (310) is rotated relative to sealing member (170).

2. Exemplary Tissue Holder Trays

Figure 15:
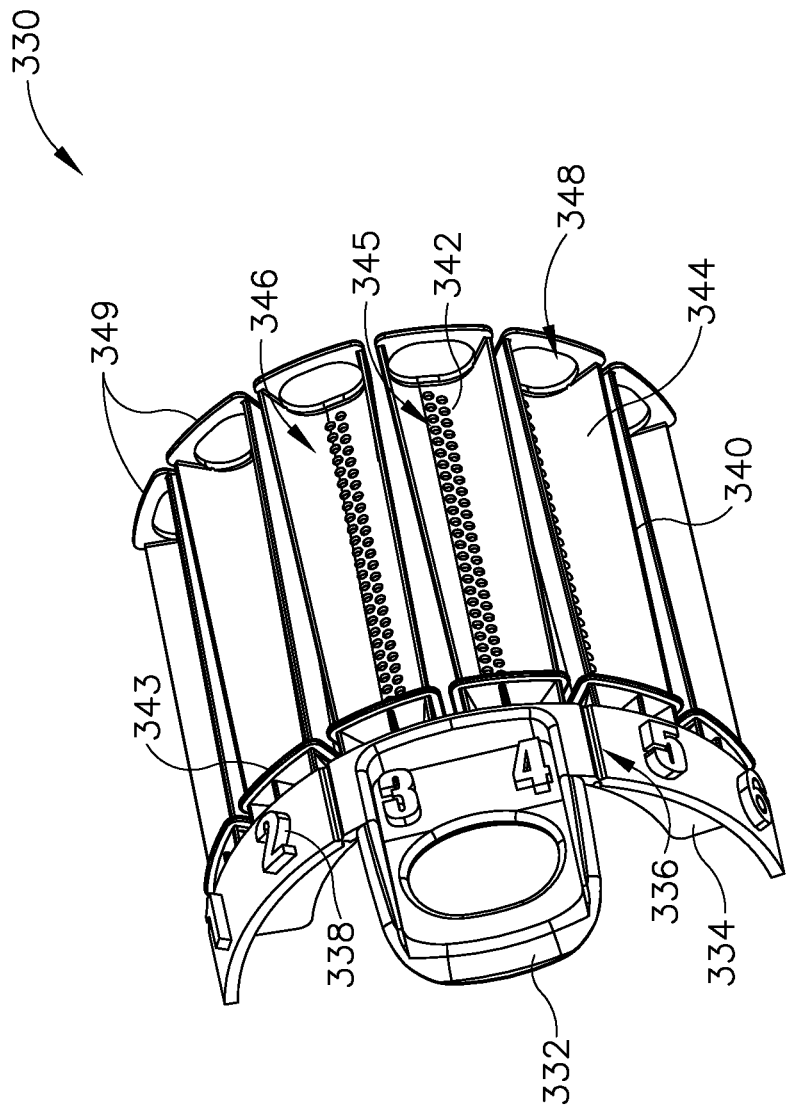
FIG. 15 depicts a perspective view of a tissue sample tray of the tissue sample holder assembly of FIG. 9.

As noted above, tissue sample holder trays (330) are configured to removably engage manifold (310). As best seen in FIG. 15, each tissue sample holder tray (330) of the present example includes a grip (332), a proximal wall (334), and a plurality of strips (340) extending distally from proximal wall (334). Strips (340) are sized and configured for insertion into associated passages (312) of manifold (310). Each strip (340) includes a pair of sidewalls (344) and a floor (342). Each pair of sidewalls (344) and floor (342) together define a corresponding tissue sample chamber (346). An opening (348) is provided at the distal end of each tissue sample chamber (346). Opening is sized and positioned to correspond with opening (174) of sealing member (170). Thus, the lumen (151) of cutter (150) is in fluid communication with the tissue sample chamber (346) of the strip (340) inserted in the passage (312) that is at the 12 o'clock position. As best seen in FIG. 11, strips (340) are configured such that the distal portion of each strip (340) receives support from a corresponding shelf (316) of manifold (310). Each floor (342) includes a plurality of openings (345) that provide fluid communication between tissue sample chamber (346) of strip (340) and lateral recess (314) of the passage (312) associated with strip (340). Thus, vacuum, atmospheric air, etc. that is communicated to opening (176) via tube (20) is further communicated to lumen (151) of cutter (150) via lateral recess (314), openings (345), and tissue sample chamber (346). During operation of biopsy device (10), tissue samples severed by distal edge (152) of cutter (150) are communicated proximally through the lumen (151) of cutter (150) and are then deposited into the tissue sample chamber (346) that is aligned with lumen (151) of cutter (150). Manifold (310) is rotated to successively align tissue sample chambers (346) with lumen (151) of cutter (150), enabling several tissue samples to be separately deposited in different tissue sample chambers (346) during operation of biopsy device (10). Bodily fluids and saline, etc. that are pulled through lumen (151) will pass through tissue sample holder (300) and tube (20) and are eventually deposited in vacuum canister (70).

Each strip (340) also includes a pair of wiper seals (343, 349) that seal against the interior of passage (312) when strip (340) is fully inserted into passage (312). Wiper seals (343, 349) provide a fluid tight seal for tissue sample chambers (346) and further provide frictional resistance to removal of strips (340) from manifold (310). Grips (332) are configured to facilitate removal of strips (340) from manifold (310), such as during or after a biopsy procedure to retrieve or otherwise directly observe tissue samples deposited in tissue sample chambers (346). Trays (330) also include numerical indicia (338) associated with each tissue sample chamber (346). In addition, trays (330) include pinched regions (336) that facilitate flattening of trays (330). In particular, pinched regions (336) provide sufficient flexibility to enable trays (330) to form an arcuate configuration for insertion into manifold (310); while also enabling trays (330) to form a generally flat configuration such as after trays (330) are removed from manifold (310) for inspection of tissue samples in trays (330). In some versions, the foregoing pinched regions (336) are further configured in accordance with at least some of the teachings of U.S. patent Ser. No. 14/208,354, the disclosure of which is incorporated by reference herein.

It should be understood that manifold (310) and/or trays (330) may be configured in numerous other ways. By way of example only, manifold (310) and/or trays (330) may be configured in accordance with at least some of the teachings of U.S. Pat. Pub. No. 2008/0214955, the disclosure of which is incorporated by reference herein. As another merely illustrative example, manifold (310) and/or trays (330) may be configured in accordance with at least some of the teachings of U.S. Pat. Pub. No. 2010/0160824, the disclosure of which is incorporated by reference herein. It should also be understood that tissue sample holder (300) need not necessarily position chambers (346) coaxially with lumen (151) of cutter (150). Tissue sample holder (300) may index chambers (346) relative to cutter (150) in any other suitable fashion. For instance, chambers (346) may extend along axes that are always offset from the axis of lumen (151), along axes that are oblique or perpendicular relative to the axis of lumen (151), or along other axes. Similarly, it should be understood that manifold (310) may rotate about an axis that is oblique or perpendicular relative to the axis of lumen (151). Yet in other examples, tissue sample holder trays (330) may be used in conjunction with a imaging system which may be configured in accordance with at least some of the teachings of U.S. application Ser. No. 14/208,354, entitled "Biopsy Device," filed Sep. 18, 2014, the disclosure of which is incorporated by reference herein. Still other suitable configurations will be apparent to those of ordinary skill in the art in view of the teachings herein.

3. Exemplary Accessory Chamber and Plug

Figure 16:
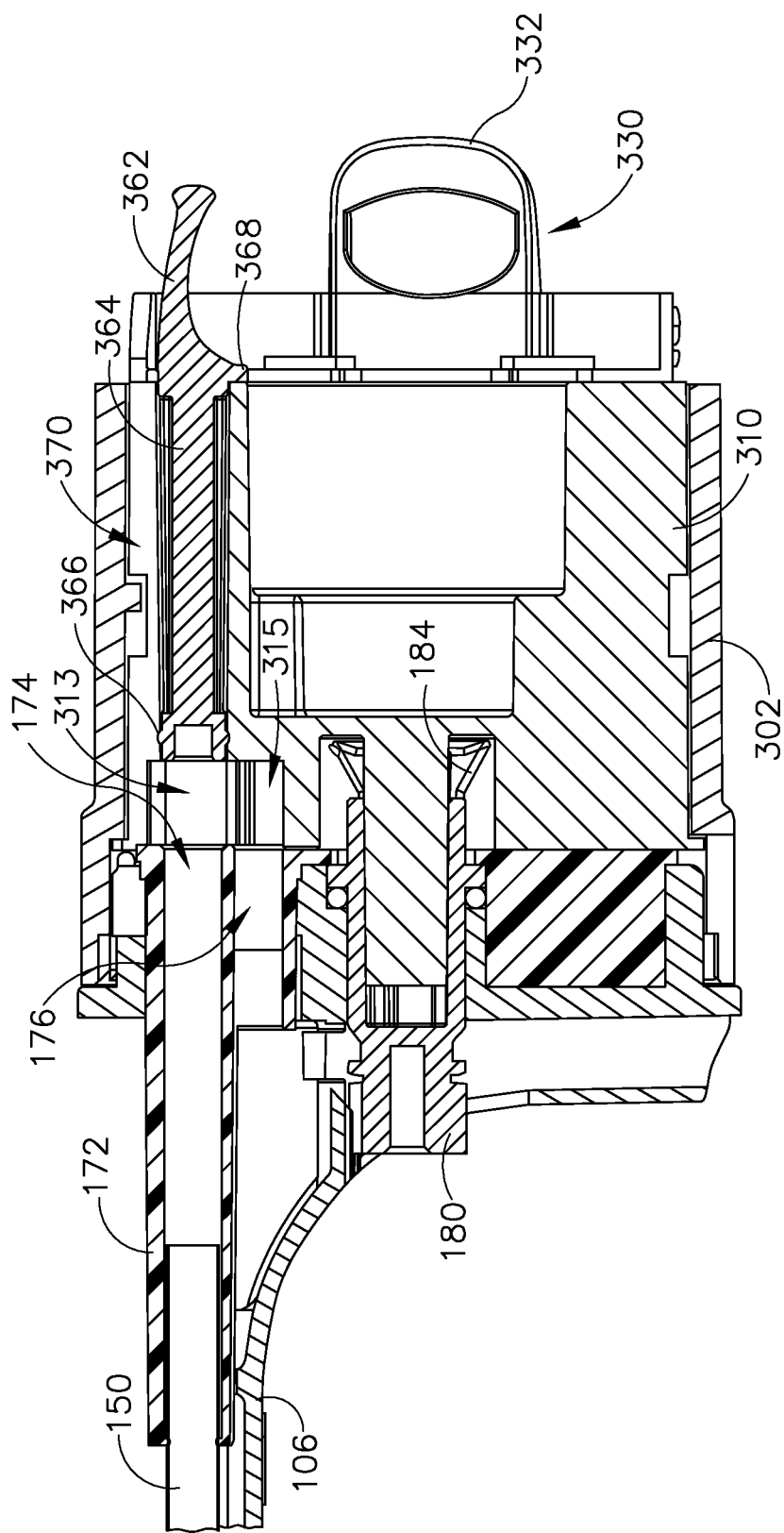
FIG. 16 depicts a side cross-sectional view of the tissue sample holder assembly of FIG. 9, with a plug aligned with the cutter.

As best seen in FIGS. 12 and 16 and as noted above, tissue sample holder (300) of the present example includes a plug (360) that is received in a dedicated passage (313) of manifold (310). Plug (360) includes a grip (362) and a longitudinally extending body (364). Body (364) extends through part of the length of passage (313), distally terminating at the longitudinal position corresponding with the proximal end of recess (315). Plug (360) includes a pair of seals (366, 368) that seal against the interior of passage (313) when plug (360) is fully inserted in passage (313). Seals (366, 368) thus keep passage (313) fluid tight when plug (360) is inserted in passage (313). Passage (313) is configured to receive the shaft of a biopsy site marker applier. Passage (313) may also receive an instrument for delivering medicine, etc. to a biopsy site. By way of example only, passage (313) may receive an adapter configured to provide an interface between passage (313) and a conventional medicine delivery device. An example of such an adapter and other uses/configurations for a passage like passage (313) are described in U.S. Pat. Pub. No. 2008/0221480, the disclosure of which is incorporated by reference herein. Plug (360) and/or passage (313) may also be configured and operable in accordance with at least some of the teachings of U.S. Pat. No. 8,938,285, entitled "Access Chamber and Markers for Biopsy Device," issued Jan. 20, 2015, the disclosure of which is incorporated by reference herein. Still other suitable configurations will be apparent to those of ordinary skill in the art in view of the teachings herein. In some other versions, plug (360) and/or passage (313) are simply omitted.

IV. EXEMPLARY TISSUE SAMPLE HOLDER INDEXING SYSTEM

Figure 17:
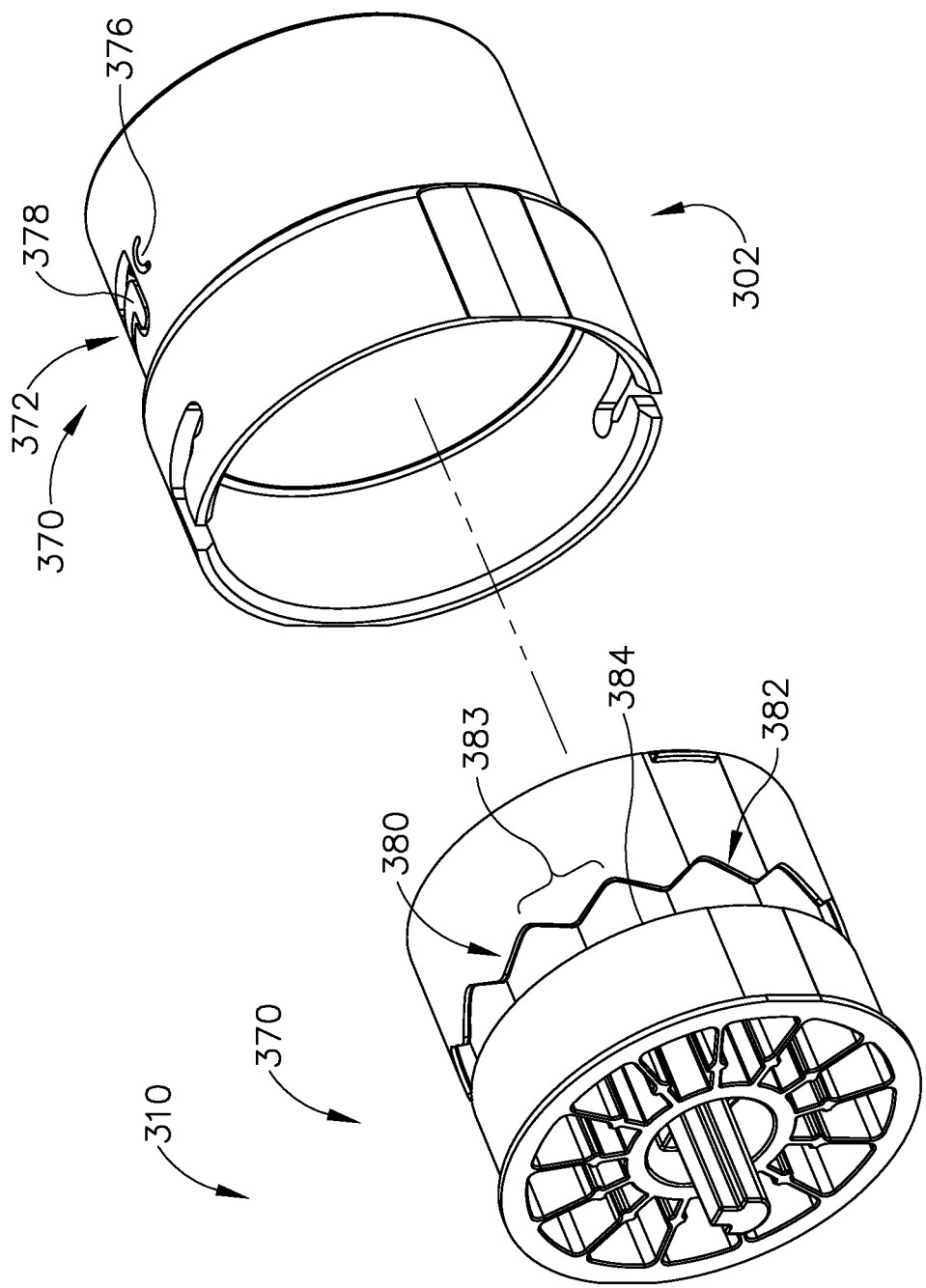
FIG. 17 depicts a enlarged exploded view of the rotatable manifold and a transparent cover of the tissue sample holder assembly of FIG. 9.

FIG. 17 shows an exploded view of the tissue sample holder (300) showing manifold (310) and transparent cover (302). As described above, manifold (310) is configured to rotate relative to transparent cover (302) thereby indexing passages (312) with cutter lumen (151). Tissue sample holder (300) includes tissue sample holder indexing system (370). Indexing system (370) comprises transparent cover (302) having a plurality of followers (372) which engage a recessed feature (380) of manifold (310) to bias manifold (310) toward a plurality of discrete rotational positions, as will be described in further detail below.

As described above, manifold (310) comprises recessed feature (380). Recessed feature (380) comprises a camming feature (382) and a retention feature (384). As can be seen, camming feature (382) comprises a plurality of rounded triangular surfaces (383). As will be described in further detail below, rounded triangular surfaces (383) are operable to translate manifold (310) relative to transparent cover (302) as manifold (310) is rotated. It will be appreciated that rounded triangular surfaces (383) may comprise a variety of shapes and/or sizes beyond rounded triangles. For instance, rounded triangular surfaces (383) may be sinusoidal in shape, wavy, or the like. Of course, other shapes and/or sizes of rounded triangular surfaces (383) will be apparent to those of ordinary skill in the art in view of the teachings herein.

Retention feature (384) is shown as a flat, proximally facing annular surface extending around the perimeter of manifold (310). The flat surface is shown as being orthogonal to the longitudinal axis of manifold (310). As will be described in greater detail below, retention feature (384) is operable to cooperate with camming feature (382) to index manifold (310) with cutter lumen (151).

FIGS. 17-19 show transparent cover (302) in a plurality of different views. As can best be seen in FIG. 17, transparent cover (302) includes a plurality of followers (372). In the present example, each follower (372) includes a rounded protrusion (374) which is configured to engage recessed feature (380) of manifold (310). Each follower (372) may also comprise either a static support (376) or a resiliently biased arm (378), depending upon which surface (e.g., camming feature (382) or retention feature (384)) of recessed feature (380) the particular follower (372) is configured to engage. Resiliently biased arm (378) is configured to support a protrusion (374) radially, yet permit protrusion (374) to move longitudinally from its resiliently biased position. Static support (376) is configured to hold a protrusion (374) in a static position relative to transparent cover (302).

As can be seen in FIG. 18, one side of transparent cover (302) is configured with followers (372) having a static support (376) and a resiliently biased arm (378) while another side of transparent cover (302) is configured with a single follower (372) having a resiliently biased arm (378). Of course, other configurations of followers (372) may be utilized as will be apparent to those of ordinary skill in the art in view of the teachings herein. As can best be seen in FIG. 19, static support (376) and resiliently biased arm (378) are positioned such that their respective protrusions (374) are radially and longitudinally offset relative to each other. It will be appreciated that protrusion (374) of static support (376) is positioned to engage camming feature (382) of recessed feature (380), while protrusion (374) of resiliently biased arm (378) is positioned to engage retention feature (384) of recessed feature (380).

FIGS. 20A-B show indexing system (370) in an exemplary mode of operation. Generally, FIG. 20A shows indexing system (370) in an indexed state, where an individual passage (312, 313) of manifold (310) is aligned with cutter lumen (151). Likewise, FIG. 20B shows indexing system (370) in an unindexed state where manifold (310) is rotating from one passage (312, 313) to another passage (312, 313). Once manifold (310) rotates to the position shown in FIG. 20B, it may continue to rotate and indexing system (370) will return to the state shown in FIG. 20A with another passage (312, 313) aligned with cutter lumen (151). Accordingly, indexing system (370) provides an additional mechanism (beyond that provided by grasping feature (184)) to ensure that a particular passage (312, 313) is aligned with cutter lumen (151).

As can be seen in FIG. 20A, indexing system (370) is in an indexed state. In the indexed state, protrusion (374) of static support (376) is engaged by the proximal most portion of camming feature (382). Protrusion (374) of static support (376) is urged to the proximal most portion of camming feature (382) by protrusion (374) of resiliently biased arm (378). In particular, protrusion (374) of resiliently biased arm (378) is configured to engage retention feature (384) of manifold (310). Accordingly, resiliently biased arm (378), via the engagement by protrusion (374), resiliently biases manifold (310) distally. With manifold (310) resiliently biased distally, protrusion of static support (376) is urged to the proximal most portion of camming feature (382).

Indexing system (370) shifts from the indexed state (FIG. 20A) to the unindexed state (FIG. 20B) by manifold (310) rotating about central shaft (320). In particular, as manifold (310) rotates, the rotational force applied to central shaft (320) by grasping feature (184) is converted into a longitudinal force via protrusion (374) of static support (376) and camming feature (382) of manifold (310). In other words, as manifold (310) rotates, manifold (310) also translates relative to transparent cover (302) as protrusion (374) of static support (376) travels along camming feature (382) of manifold (310). It should be understood that the force generated by the rotation of manifold (310) is sufficient to overcome the resilient bias provided by resiliently biased arm (378) of transparent cover (302). Thus, resiliently biased arm (378) is shown as being bent in the proximal direction in FIG. 20B.

For manifold (310) to index another passage (312, 313) with cutter lumen (151), manifold (310) may continue to rotate about central shaft (320). Once manifold (310) is indexed with another passage (312, 313), indexing system (370) will return to the indexed state depicted in FIG. 20A. In particular, as manifold (310) rotates, protrusion (374) of static support (376) will continue to travel along camming feature (382). Accordingly, protrusion (374) of resiliently biased arm (378) will begin to resiliently bias manifold proximally as protrusion (374) of static support (376) travels along camming feature (382).

It should be understood that the coupling between central shaft (320) and grasping feature (184) may have some amount of backlash such that central shaft (320) may move without corresponding movement of grasping feature (184). Thus, while a passage (312, 313) of manifold (310) may be indexed solely by central shaft (320) and grasping feature (184), indexing system may be operable to overcome any misindexing caused by backlash between central shaft (320) and grasping feature (184). Of course, in other versions backlash may be minimal and indexing system (370) may merely provide a secondary mechanism for indexing passages (312, 313) of manifold (310) with cutter lumen (151). Additionally, in some examples the mechanical motion provided by grasping feature (184) may be eliminated and tissue sample holder (300) may be configured for manual rotation. In such examples, indexing system (370) may provide the sole mechanism for indexing passages (312, 313) of manifold (310) with cutter lumen (151).

V. EXEMPLARY ALTERNATIVE INDEXING SYSTEM WITH HEMISPHERICAL INDEXING FEATURES

While indexing system (370) described above provides one set of exemplary features for indexing tissue sample holder (300), numerous other configurations may be used. As will be understood, various tissue sample holders similar to tissue sample holder (300) may provide indexing systems of various alternative configurations. Such alternatively configured indexing systems may be desirable for numerous reasons, as will be described in greater detail below. For instance, in some circumstances, the indexing systems described herein may generally provide enhanced operability. Additionally or in alternative, such indexing systems may be desirable to enhance usability in conjunction with manual rotation of the tissue sample holder. While various alternative tissue sample holders are described below, it should be understood that other examples will be apparent to those of ordinary skill in the art in view of the teachings herein. It should be further understood that various features and/or structures of tissue sample holders described with respect to a particular tissue sample holder herein may be readily incorporated with other tissue sample holders described herein.

FIG. 21 shows an exemplary alternative tissue sample holder (1000). Tissue sample holder (1000) is substantially the same as tissue sample holder (300) described above, unless otherwise noted herein. For instance, like with tissue sample holder (300), tissue sample holder (1000) is configured to be readily incorporated into biopsy device (10) as described above. Alternatively, tissue sample holder (1000) may be configured for incorporation into any other suitable biopsy device (10). Merely exemplary alternative biopsy devices into which tissue sample holder may be readily incorporated are described in U.S. Pub. No. 2015/0065913, entitled "Tissue Collection Assembly for Biopsy Device," published on Mar. 5, 2015, the disclosure of which is incorporated by reference herein.

Figure 22:
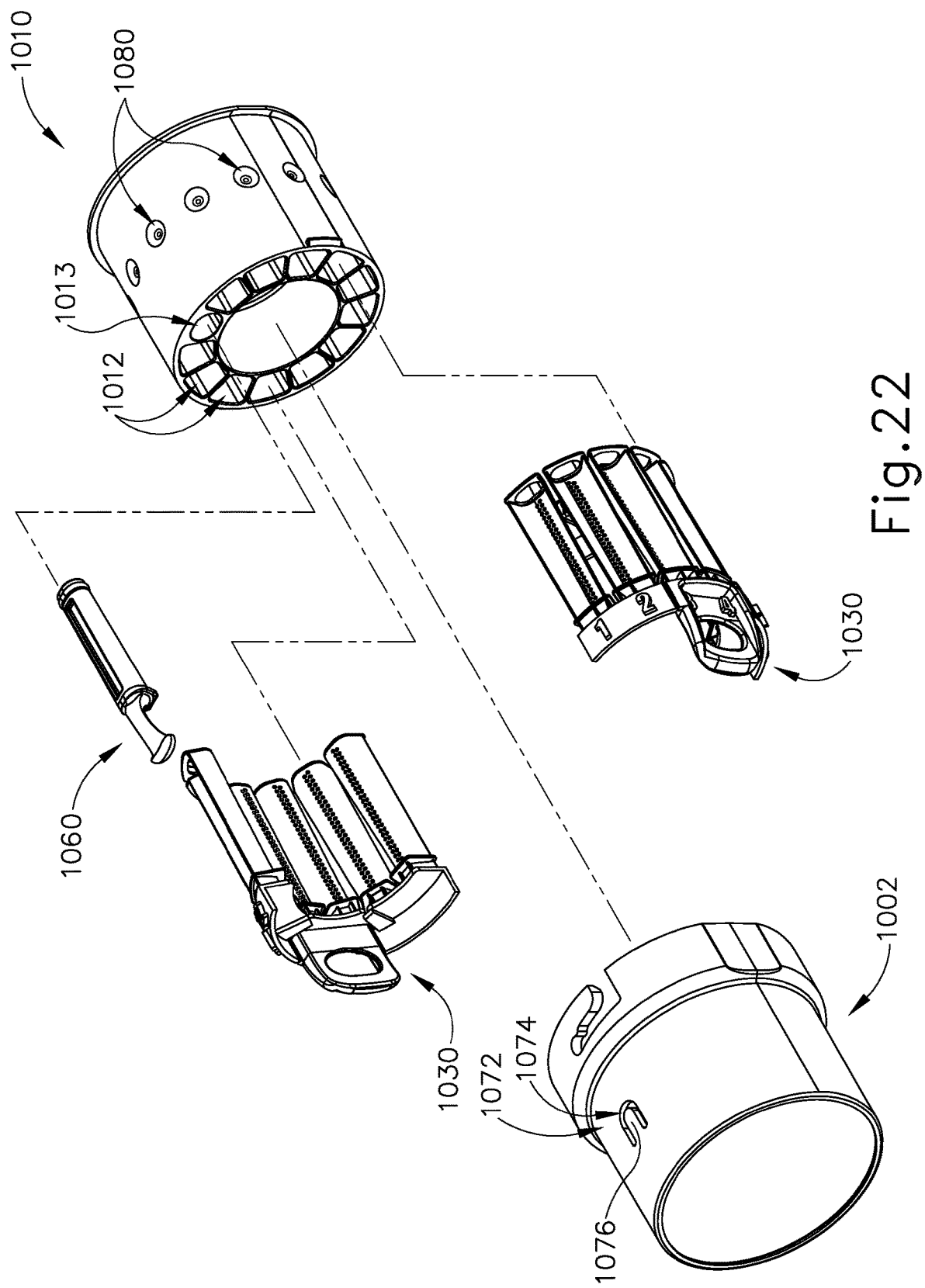
FIG. 22 depicts a perspective exploded view of the tissue sample holder of FIG. 21.

As can best be seen in FIG. 22, tissue sample holder (1000) comprises a manifold (1010) and transparent cover (1002). As similarly described above with respect to manifold (310), manifold (1010) is configured to rotate relative to transparent cover (1002) thereby indexing a plurality of passages (1012) containing trays (1030) with cutter lumen (151) of biopsy device (10). In addition to passages (1012), manifold (1010) comprises a single passage (1013) for receipt of a plug (1060), similar to plug (360) described above. It should be understood that manifold (1010) and cover (1002) are substantially the same as manifold (310) and cover (302) described above, unless otherwise noted herein.

Like with tissue sample holder (300) described above, tissue sample holder (1000) includes tissue sample holder indexing system (1070). Indexing system (1070) comprises transparent cover (1002) having a resiliently biased tab (1072) which engages a plurality of discrete indexing features (1080) oriented around the circumference of manifold (1010) to bias manifold (1010) toward a plurality of discrete rotational positions, as will be described in further detail below.

Figure 23:
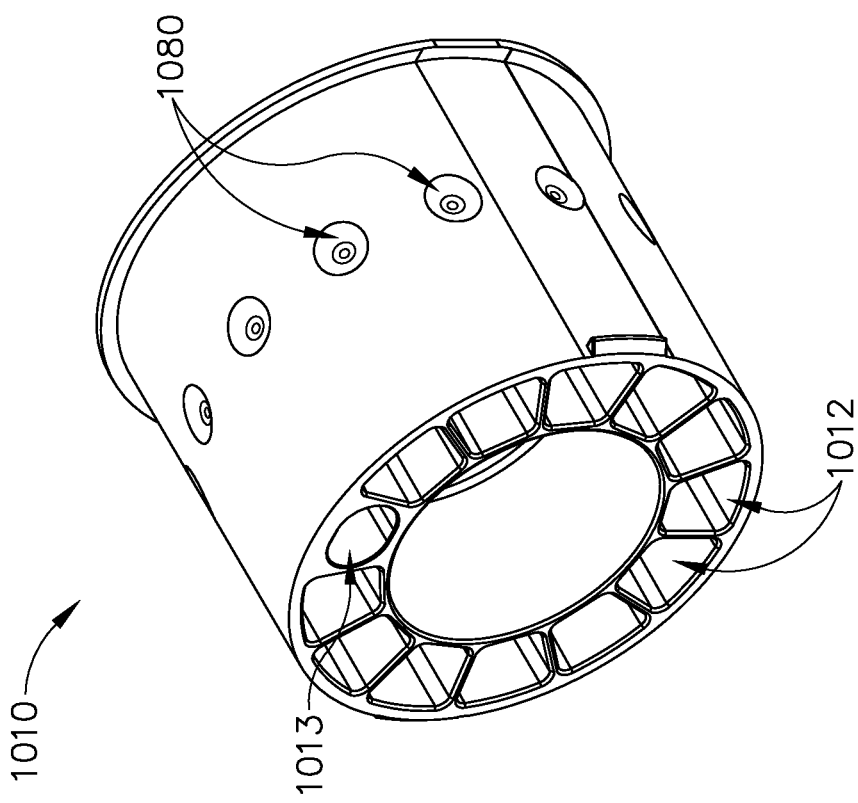
FIG. 23 depicts a perspective view of a manifold of the tissue sample holder of FIG. 21.

As can be seen in FIG. 23, manifold (1010) comprises thirteen discrete indexing features (1080). Each indexing feature (1080) is generally formed as a rounded indentation extending inwardly from the exterior surface of manifold (1010). Manifold (1010) of the present example has a single indexing feature (1018) corresponding to each passage (1012, 1013). As will be described in further detail below, indexing features (1080) are operable to engage with transparent cover (1002) to urge manifold (1010) relative to transparent cover (1002) to a particular indexing position. It will be appreciated that each indexing feature (1080) may comprise a variety of shapes and/or sizes beyond rounded indentations. Additionally, although a plurality of discrete indexing features (1080) is shown, it should be understood that in other examples indexing features (1080) may be connected to each other. In other words, indexing features (1080) may alternatively comprise a single feature of variable depth extending circumferentially around manifold (1010). Of course, other shapes, sizes, and/or configurations of indexing features (1080) will be apparent to those of ordinary skill in the art in view of the teachings herein.

Figure 24:
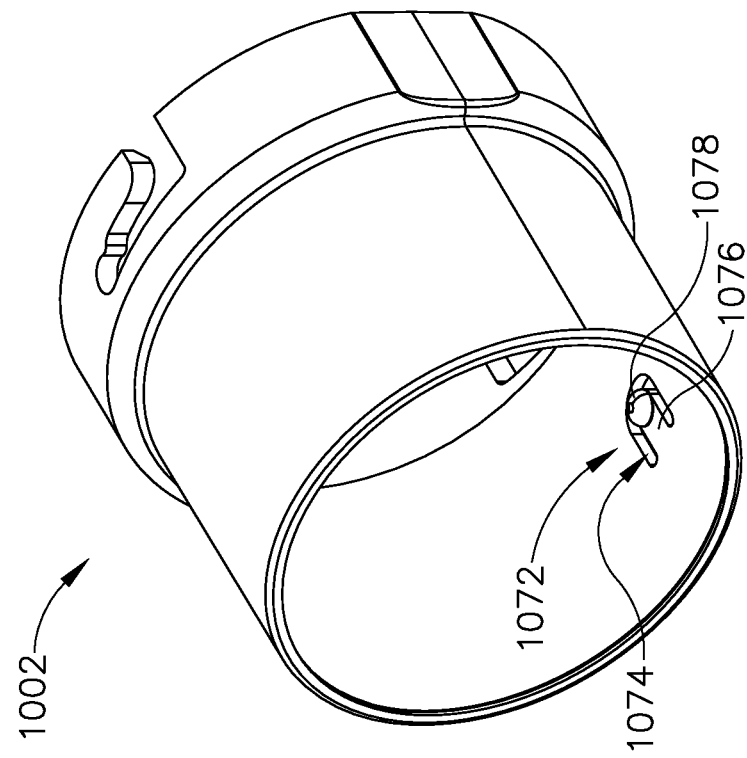
FIG. 24 depicts a perspective view of a transparent cover of the tissue sample holder of FIG. 21.

FIG. 24 shows transparent cover (1002) in greater detail. As can be seen, transparent cover (1002) includes resilient tab (1072), which is of integral construction with transparent cover (1002). In the present example, resilient tab (1072) is defined by a single slot (1074) extending through transparent cover (1002). Resilient tab (1072) comprises a resilient arm (1076) and a manifold engagement portion (1078). Resilient arm (1076) is configured to flex or elastically deform as resilient tab (1072) engages and disengages with indexing features (1080). Manifold engagement portion (1078) extends into the inner diameter of transparent cover (1002) and has a generally hemispherical shape. It should be understood that the particular shape of manifold engagement portion (1078) generally corresponds to the particular shape of each indexing feature (1080). Thus, in examples where the shapes of indexing features (1080) are varied, the particular shape of manifold engagement portion (1078) may likewise be varied. As will be understood, the combination of resilient arm (1076) and manifold engagement portion (1078) provides a detent relationship that permits resilient tab (1072) to travel into and out of indexing features (1080) as manifold (1010) is rotated to sequentially bias a particular passage (1012, 1013) of manifold (1010) into alignment cutter lumen (115). Although the present example is shown as having a single resilient tab (1072), it should be understood that in other examples any suitable number of resilient tabs (1072) may be used. Additionally, although resilient tab (1072) is shown in the present example as being integral with transparent cover (1002), in other examples resilient tab (1072) may be a separate component fixedly secured to transparent cover (1002).

Figure 25:
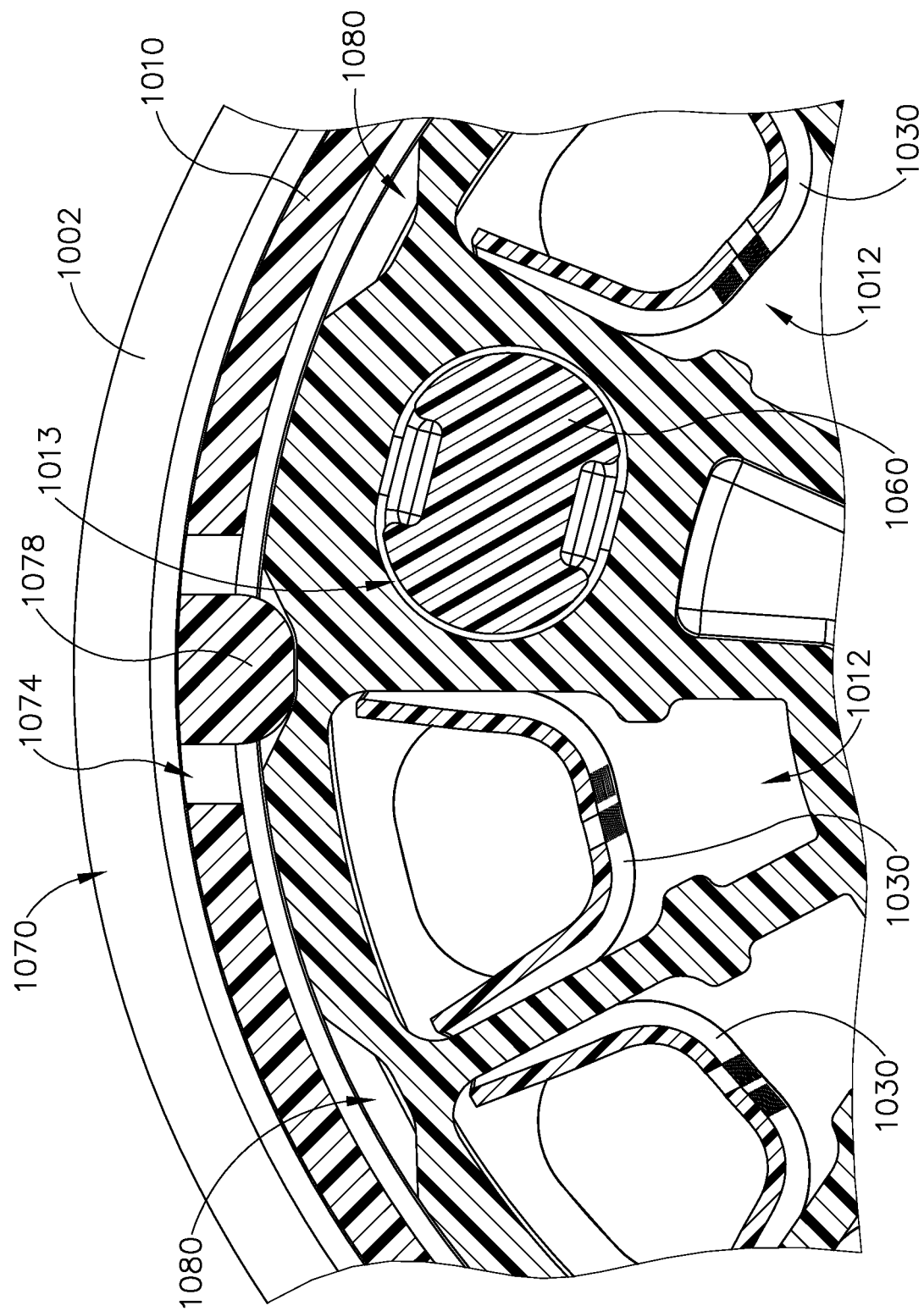
FIG. 25 depicts a partial cross-sectional end view of the tissue sample holder of FIG. 21, with the cross-section taken along line 25-25 of FIG. 21 and the manifold in an indexed position.
Figure 26:
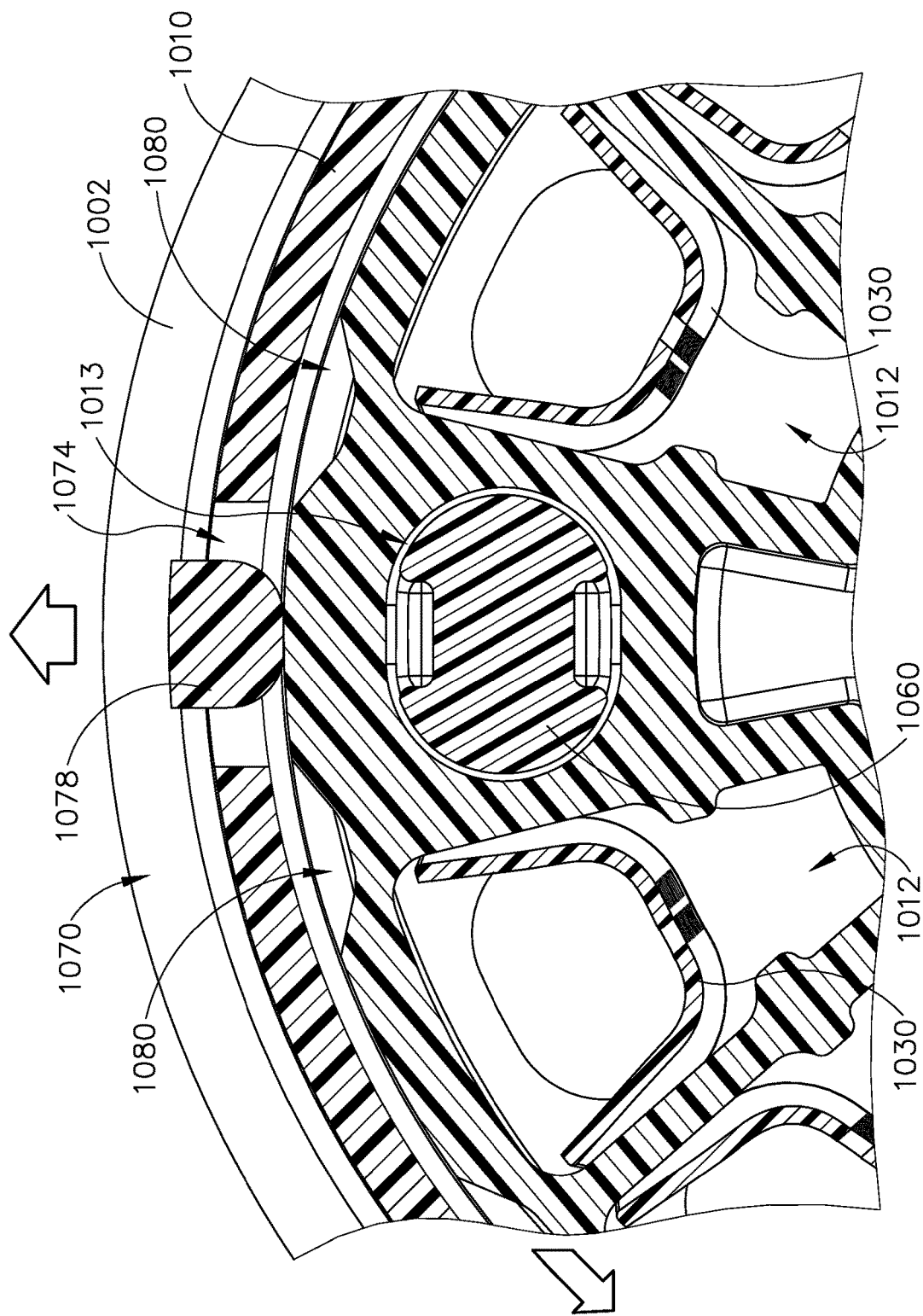
FIG. 26 depicts another partial cross-sectional end view of the tissue sample holder of FIG. 21, with the manifold in an un-indexed position.

FIGS. 25 and 26 show indexing system (1070) in an exemplary mode of operation. Generally, FIG. 25 shows indexing system (1070) in an indexed state, where an individual passage (1012, 1013) of manifold (1010) is aligned with cutter lumen (151). Likewise, FIG. 26 shows indexing system (1070) in an unindexed state where manifold (1010) is rotating from one passage (1012, 1013) to another passage (1012, 1013). Once manifold (1010) rotates to the position shown in FIG. 26, it may continue to rotate and indexing system (1070) will return to the state shown in FIG. 25 with another passage (1012, 1013) aligned with cutter lumen (151). Accordingly, indexing system (1070) provides an additional mechanism (beyond that provided by grasping feature (184)) to ensure that a particular passage (1012, 1013) is aligned with cutter lumen (151).

As can be seen in FIG. 25, indexing system (1070) is in an indexed state. In the indexed state, manifold engagement portion (1078) of resilient tab (1072) is disposed within a corresponding indexing feature (1080). Additionally, resilient arm (1076) is in a relaxed state, holding manifold engagement portion (1078) within indexing feature (1080) and thereby biasing manifold (1010) in the position shown in FIG. 25.

Indexing system (1070) shifts from the indexed state (FIG. 25) to the unindexed state (FIG. 26) by manifold (1010) rotating relative to transparent cover (1002) via a central shaft (not shown) as similarly described above with respect to manifold (310). As manifold (1010) rotates, the rotational force drives manifold engagement portion (1078) upwardly out of a particular indexing feature (1080). Motion of manifold engagement portion (1078) upwardly is against the resilient bias of resilient arm (1076) such that resilient arm (1076) elastically deforms thereby storing at least some energy within resilient arm (1076).

For manifold (1010) to index another passage (1012, 1013) with cutter lumen (151), manifold (1010) may continue to rotate relative to transparent cover (1002) via the central shaft. Once manifold (1010) is indexed with another passage (1012, 1013), indexing system (1070) will return to the indexed state depicted in FIG. 25 (but with manifold (1010) indexed to a different passage). In particular, as manifold (1010) rotates, the energy stored in resilient arm (1076) will drive manifold engagement portion (1078) downwardly into another indexing feature (1080). Accordingly, such a force causes indexing system (1070) to bias manifold (1010) toward a position where manifold engagement portion (1078) and a particular indexing feature (1080) is aligned. It should be understood that the relative positioning of manifold engagement portion (1078) and each indexing feature (1080) is configured to index a particular passage (1012, 1013) with cutter lumen (115). Thus, when manifold engagement portion (1078) engages with a particular indexing feature (1080), a corresponding passage (1012, 1013) is correspondingly indexed with cutter lumen (115).

It should be understood that the coupling between the central shaft and grasping feature (184) may have some amount of backlash such that the central shaft may move without corresponding movement of grasping feature (184). Thus, while a passage (1012, 1013) of manifold (1010) may be indexed solely by the central shaft and grasping feature (184), indexing system (1070) may be operable to overcome any misindexing caused by backlash between the central shaft and grasping feature (184). Of course, in other versions backlash may be minimal and indexing system (1070) may merely provide a secondary mechanism for indexing passages (1012, 1013) of manifold (1010) with cutter lumen (151). Additionally, in some examples the mechanical motion provided by grasping feature (184) may be eliminated and tissue sample holder (1000) may be configured for manual rotation. In such examples, indexing system (1070) may provide the sole mechanism for indexing passages (1012, 1013) of manifold (1010) with cutter lumen (151).

VI. EXEMPLARY ALTERNATIVE INDEXING SYSTEM WITH TRIANGULAR INDEXING FEATURES

Figure 27:
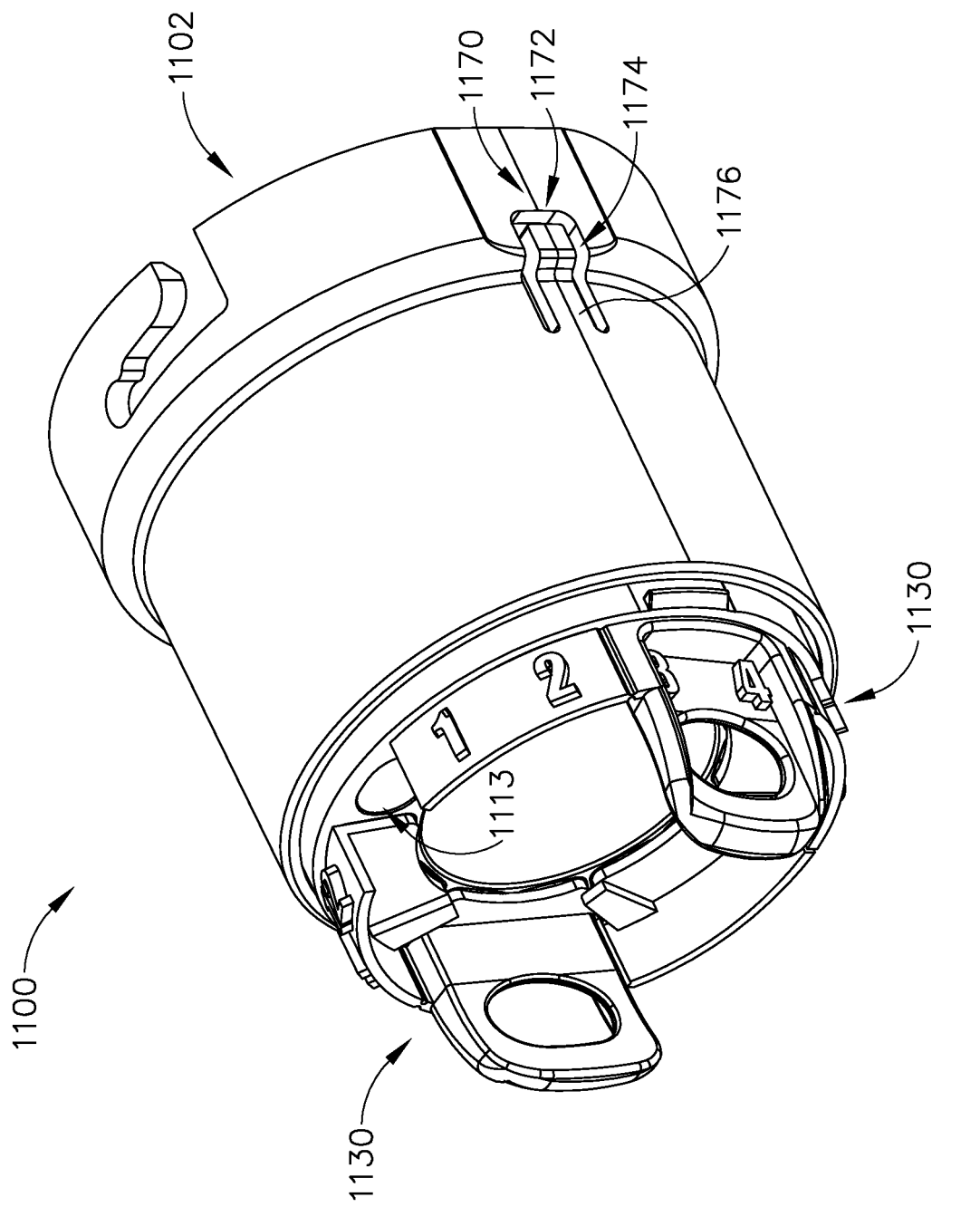
FIG. 27 depicts a perspective view of still another tissue sample holder for incorporation into the probe of FIG. 4.
Figure 28:
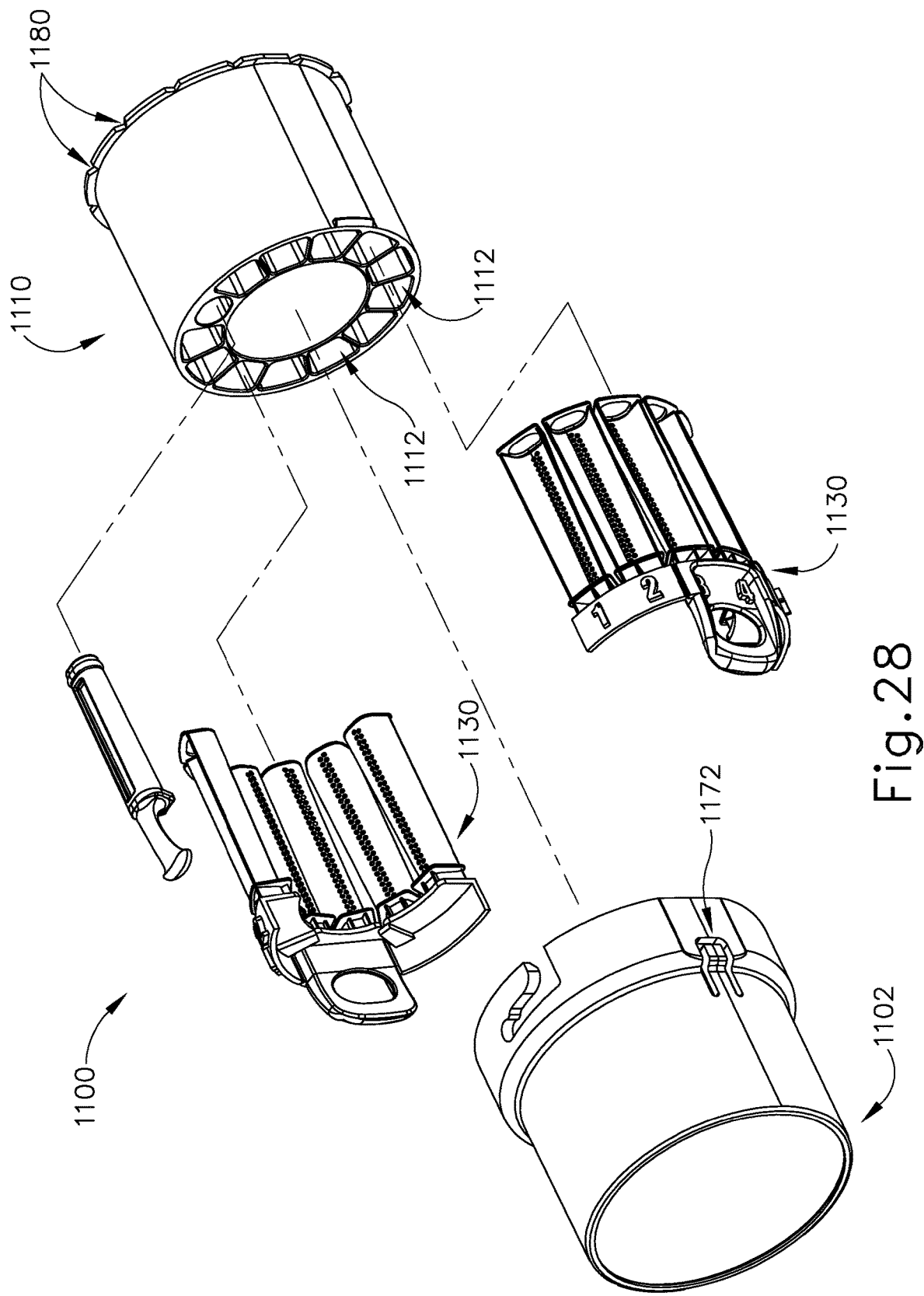
FIG. 28 depicts a perspective exploded view of the tissue sample holder of FIG. 27.

FIG. 27 shows another exemplary alternative tissue sample holder (1100). Tissue sample holder (1100) is substantially the same as tissue sample holder (300) described above, unless otherwise noted herein. For instance, like with tissue sample holder (300), tissue sample holder (1100) is configured to be readily incorporated into biopsy device (10) as described above. Alternatively, tissue sample holder (1100) may be configured for incorporation into any other suitable biopsy device (10). Merely exemplary alternative biopsy devices into which tissue sample holder may be readily incorporated are described in U.S. Pub. No. 2015/0065913, entitled "Tissue Collection Assembly for Biopsy Device," published on Mar. 5, 2015, the disclosure of which is incorporated by reference herein.

As can best be seen in FIG. 22, tissue sample holder (1100) comprises a manifold (1110) and transparent cover (1102). As similarly described above with respect to manifold (310), manifold (1110) is configured to rotate relative to transparent cover (1102) thereby indexing a plurality of passages (1112) containing trays (1130) with cutter lumen (151) of biopsy device (10). In addition to passages (1112), manifold (1110) comprises a single passage (1113) for receipt of a plug (1160) that is substantially the same as plug (360) described above. It should be understood that manifold (1110) and cover (1102) are substantially the same as manifold (310) and cover (302) described above, unless otherwise noted herein.

Like with tissue sample holder (300) described above, tissue sample holder (1100) includes tissue sample holder indexing system (1170). Indexing system (1170) comprises transparent cover (1102) having a resiliently biased tab (1172) which engages a plurality of discrete indexing features (1180) oriented around the circumference of manifold (1110) to bias manifold (1110) toward a plurality of discrete rotational positions, as will be described in further detail below.

Figure 29:
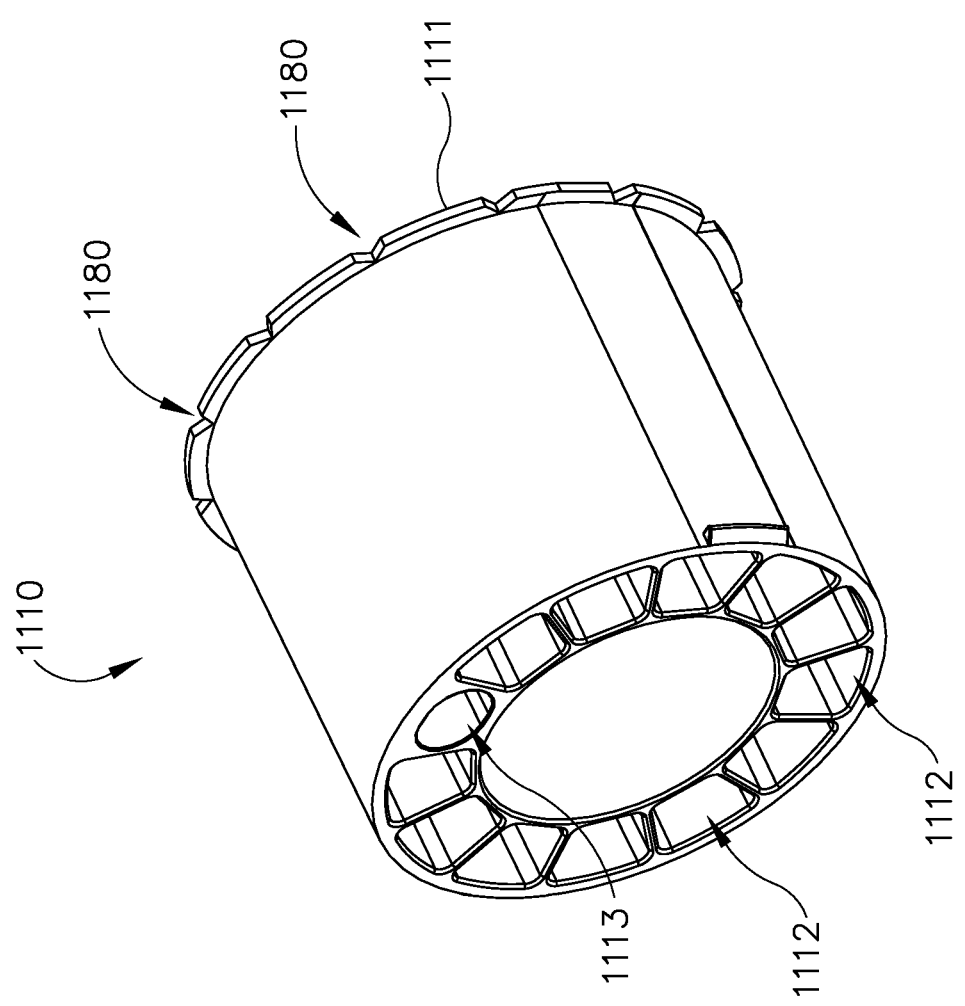
FIG. 29 depicts a perspective view of a manifold of the tissue sample holder of FIG. 27.

As can be seen in FIG. 29, manifold (1110) comprises thirteen discrete indexing features (1180). Each indexing feature (1180) is generally formed as a triangular indentation extending inwardly from the exterior surface of the proximal flange (1111) of manifold (1110). Manifold (1110) of the present example has a single indexing feature (1180) corresponding to each passage (1112, 1113). As will be described in further detail below, indexing features (1180) are operable to engage with transparent cover (1102) to urge manifold (1110) relative to transparent cover (1102) to a particular indexing position. It will be appreciated that each indexing feature (1180) may comprise a variety of shapes and/or sizes beyond triangular indentations. Additionally, although a plurality of discrete indexing features (1180) is shown, it should be understood that in other examples indexing features (1180) may be connected to each other. In other words, indexing features (1180) may alternatively comprise a single feature of variable depth extending circumferentially around manifold (1110). Of course, other shapes, sizes, and/or configurations of indexing features (1180) will be apparent to those of ordinary skill in the art in view of the teachings herein.

Figure 30:
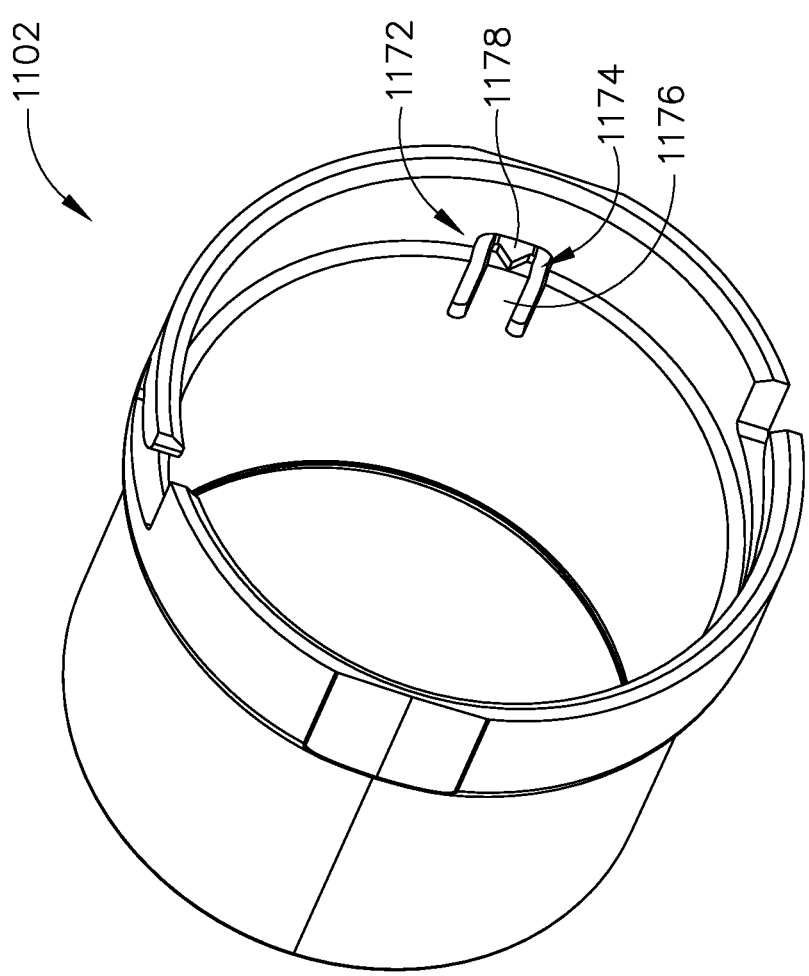
FIG. 30 depicts a perspective view of a transparent cover of the tissue sample holder of FIG. 27.

FIG. 30 shows transparent cover (1102) in greater detail. As can be seen, transparent cover (1102) includes resilient tab (1172), which is of integral construction with transparent cover (1102). In the present example, resilient tab (1172) is defined by a single slot (1174) extending through transparent cover (1102). Resilient tab (1172) comprises a resilient arm (1176) and a manifold engagement portion (1178). Resilient arm (1176) is configured to flex or elastically deform as resilient tab (1172) engages and disengages with indexing features (1118). Manifold engagement portion (1178) extends into the inner diameter of transparent cover (1102) having a generally triangular shape. It should be understood that the particular shape of manifold engagement portion (1178) generally corresponds to the particular shape of each indexing feature (1180). Thus, in examples where the shapes of indexing features (1180) are varied, the particular shape of manifold engagement portion (1178) may likewise be varied. As will be understood, the combination of resilient arm (1176) and manifold engagement portion (1078) permits resilient tab (1172) to travel into and out of indexing features (1180) as manifold (1110) is rotated to sequentially bias a particular passage (1112, 1113) of manifold (1110) into alignment cutter lumen (115). Although the present example is shown as having a single resilient tab (1172), it should be understood that in other examples any suitable number of resilient tabs (1172) may be used. Additionally, although resilient tab (1172) is shown in the present example as being integral with transparent cover (1102), in other examples resilient tab (1172) may be a separate component fixedly secured to transparent cover (1102).

Figure 31:
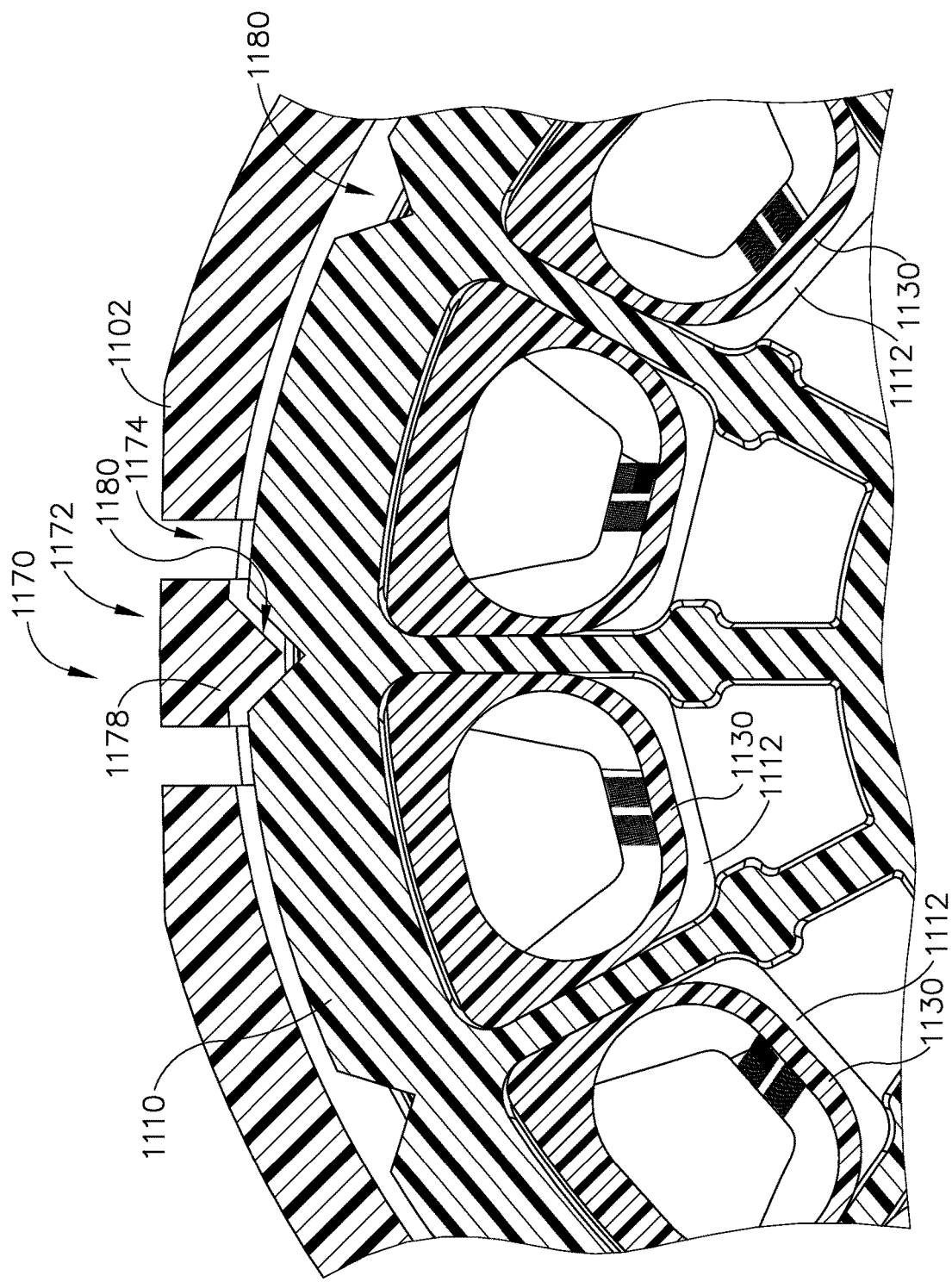
FIG. 31 depicts a partial cross-sectional end view of the tissue sample holder of FIG. 27, with the cross-section taken along line 31-31 of FIG. 27 and the manifold in an indexed position.
Figure 32:
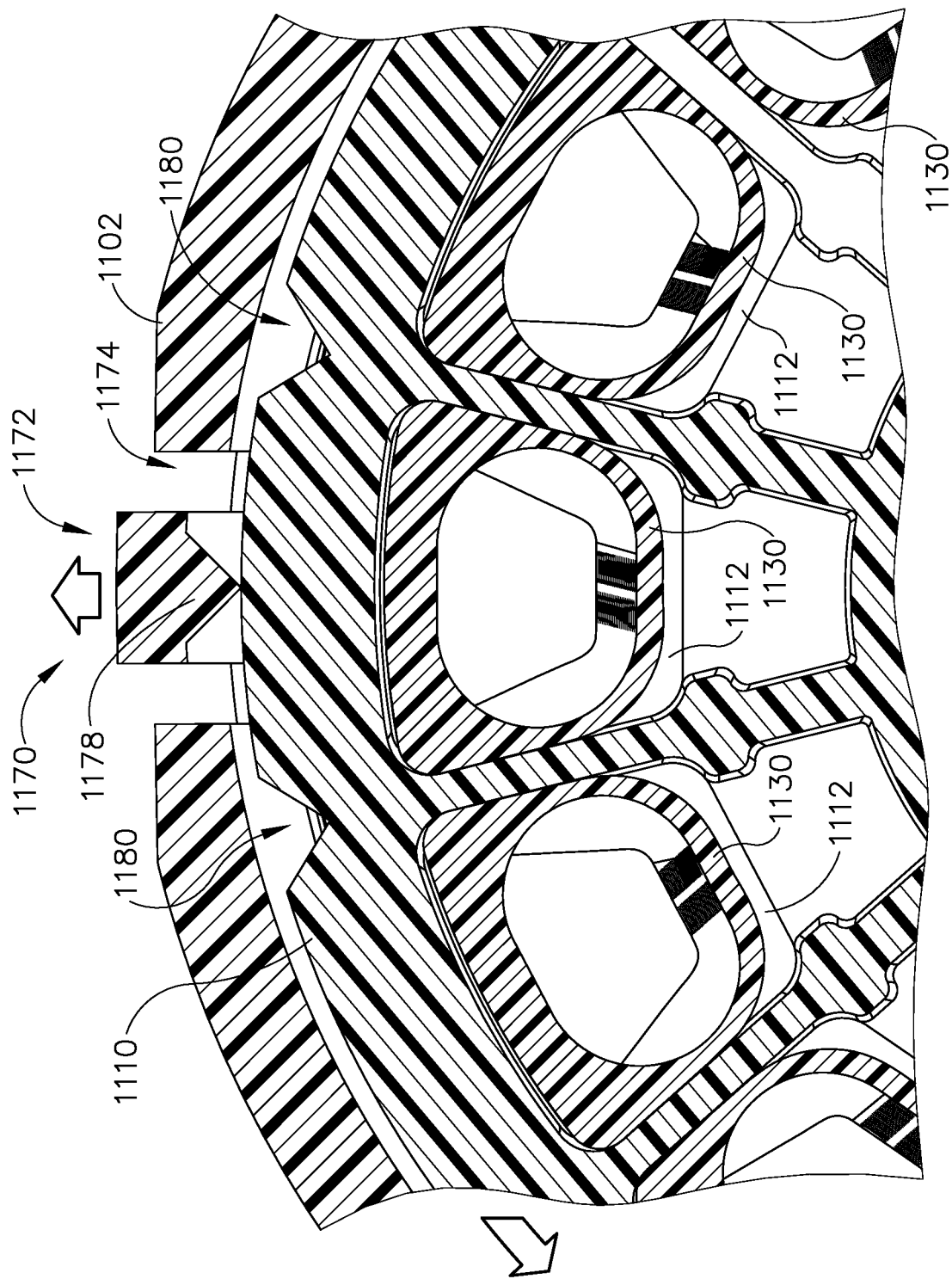
FIG. 32 depicts another partial cross-sectional end view of the tissue sample holder of FIG. 27, with the manifold in an un-indexed position.

FIGS. 31 and 32 show indexing system (1170) in an exemplary mode of operation. Generally, FIG. 31 shows indexing system (1170) in an indexed state, where an individual passage (1112, 1113) of manifold (1110) is aligned with cutter lumen (151). Likewise, FIG. 32 shows indexing system (1170) in an unindexed state where manifold (1110) is in the process of rotating from one passage (1112, 1113) to another passage (1112, 1113). Once manifold (1110) rotates to the position shown in FIG. 32, it may continue to rotate and indexing system (1170) will return to the state shown in FIG. 31 with another passage (1112, 1113) aligned with cutter lumen (151). Accordingly, indexing system (1170) provides an additional mechanism (beyond that provided by grasping feature (184)) to ensure that a particular passage (1112, 1113) is aligned with cutter lumen (151).

As can be seen in FIG. 31, indexing system (1170) is in an indexed state. In the indexed state, manifold engagement portion (1178) of resilient tab (1172) is disposed within a corresponding indexing feature (1180). Additionally, resilient arm (1176) is in a relaxed state, holding manifold engagement portion (1178) within indexing feature (1180) and thereby biasing manifold (1110) in the position shown in FIG. 31.

Indexing system (1170) shifts from the indexed state (FIG. 31) to the unindexed state (FIG. 32) by manifold (1110) rotating relative to transparent cover (1102) via a central shaft (not shown) as similarly described above with respect to manifold (310). As manifold (1110) rotates, the rotational force drives manifold engagement portion (1178) upwardly out of a particular indexing feature (1180). Motion of manifold engagement portion (1178) upwardly is against the resilient bias of resilient arm (1176) such that resilient arm (1176) elastically deforms thereby storing at least some energy within resilient arm (1176).

For manifold (1110) to index another passage (1112, 1113) with cutter lumen (151), manifold (1110) may continue to rotate relative to transparent cover (1102) via the central shaft. Once manifold (1110) is indexed with another passage (1112, 1113), indexing system (1170) will return to the indexed state depicted in FIG. 31 (but with manifold (1110) indexed to a different passage). In particular, as manifold (1110) rotates, the energy stored in resilient arm (1176) will drive manifold engagement portion (1178) downwardly into another indexing feature (1180). Accordingly, such a force causes indexing system (1170) to bias manifold (1110) toward a position where manifold engagement portion (1178) and a particular indexing feature (1180) is aligned. It should be understood that the relative positioning of manifold engagement portion (1178) and each indexing feature (1180) is configured to index a particular passage (1112, 1113) with cutter lumen (115). Thus, when manifold engagement portion (1178) engages with a particular indexing feature (1180), a corresponding passage (1112, 1113) is correspondingly indexed with cutter lumen (115).

It should be understood that the coupling between the central shaft and grasping feature (184) may have some amount of backlash such that the central shaft may move without corresponding movement of grasping feature (184). Thus, while a passage (1112, 1113) of manifold (1110) may be indexed solely by the central shaft and grasping feature (184), indexing system (1170) may be operable to overcome any misindexing caused by backlash between the central shaft and grasping feature (184). Of course, in other versions backlash may be minimal and indexing system (1170) may merely provide a secondary mechanism for indexing passages (1112, 1113) of manifold (1110) with cutter lumen (151). Additionally, in some examples the mechanical motion provided by grasping feature (184) may be eliminated and tissue sample holder (1100) may be configured for manual rotation. In such examples, indexing system (1170) may provide the sole mechanism for indexing passages (1112, 1113) of manifold (1110) with cutter lumen (151).

VII. EXEMPLARY ALTERNATIVE INDEXING SYSTEM WITH SEMI-CYLINDRICAL INDEXING FEATURES

Figure 33:
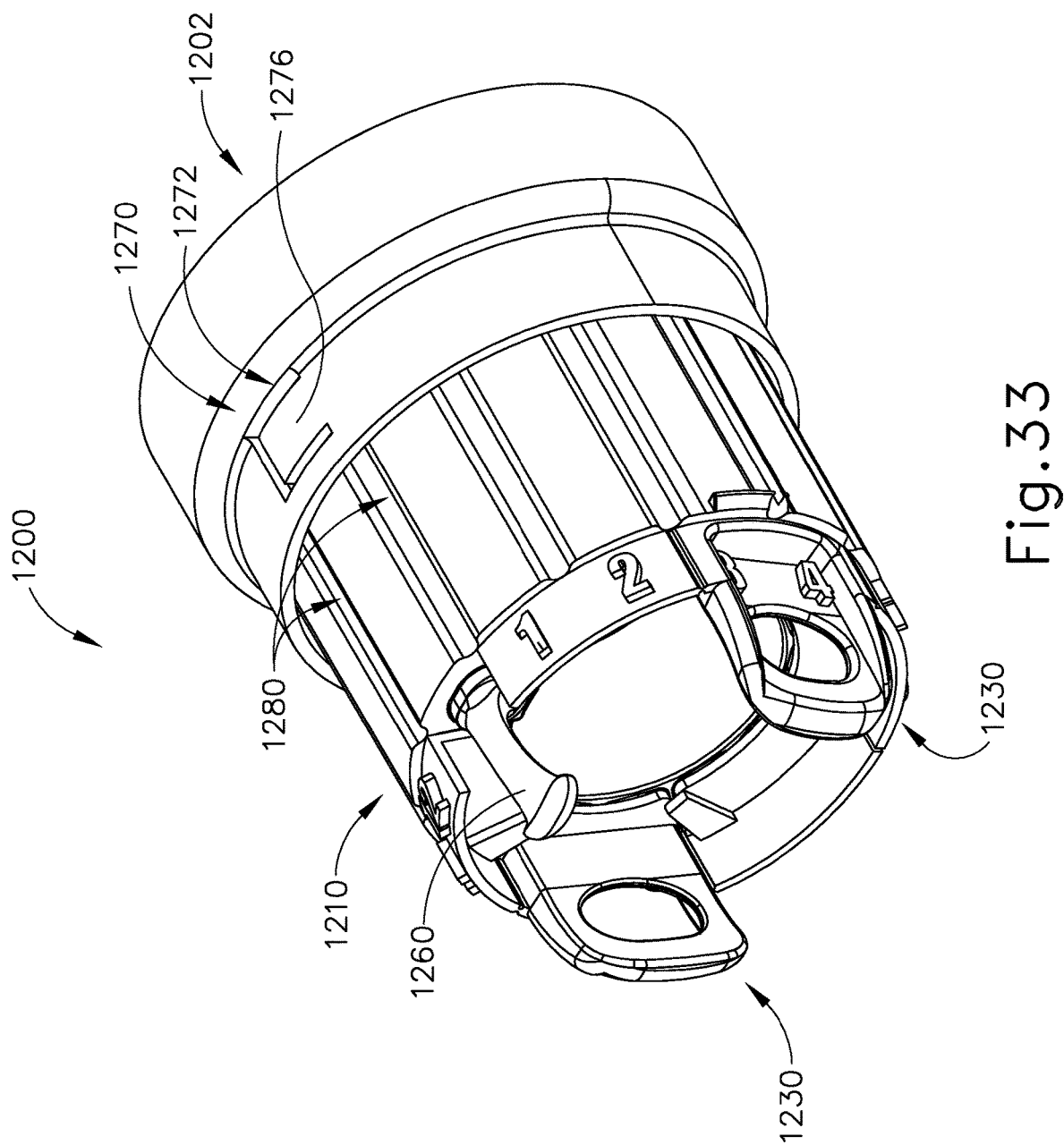
FIG. 33 depicts a perspective view of yet another tissue sample holder for incorporation into the probe of FIG. 4.

FIG. 33 shows still another exemplary alternative tissue sample holder (1200). Tissue sample holder (1200) is substantially the same as tissue sample holder (300) described above, unless otherwise noted herein. For instance, like with tissue sample holder (300), tissue sample holder (1200) is configured to be readily incorporated into biopsy device (10) as described above. Alternatively, tissue sample holder (1200) may be configured for incorporation into any other suitable biopsy device (10). Merely exemplary alternative biopsy devices into which tissue sample holder may be readily incorporated are described in U.S. Pub. No. 2015/0065913, entitled "Tissue Collection Assembly for Biopsy Device," published on Mar. 5, 2015, the disclosure of which is incorporated by reference herein.

Figure 34:
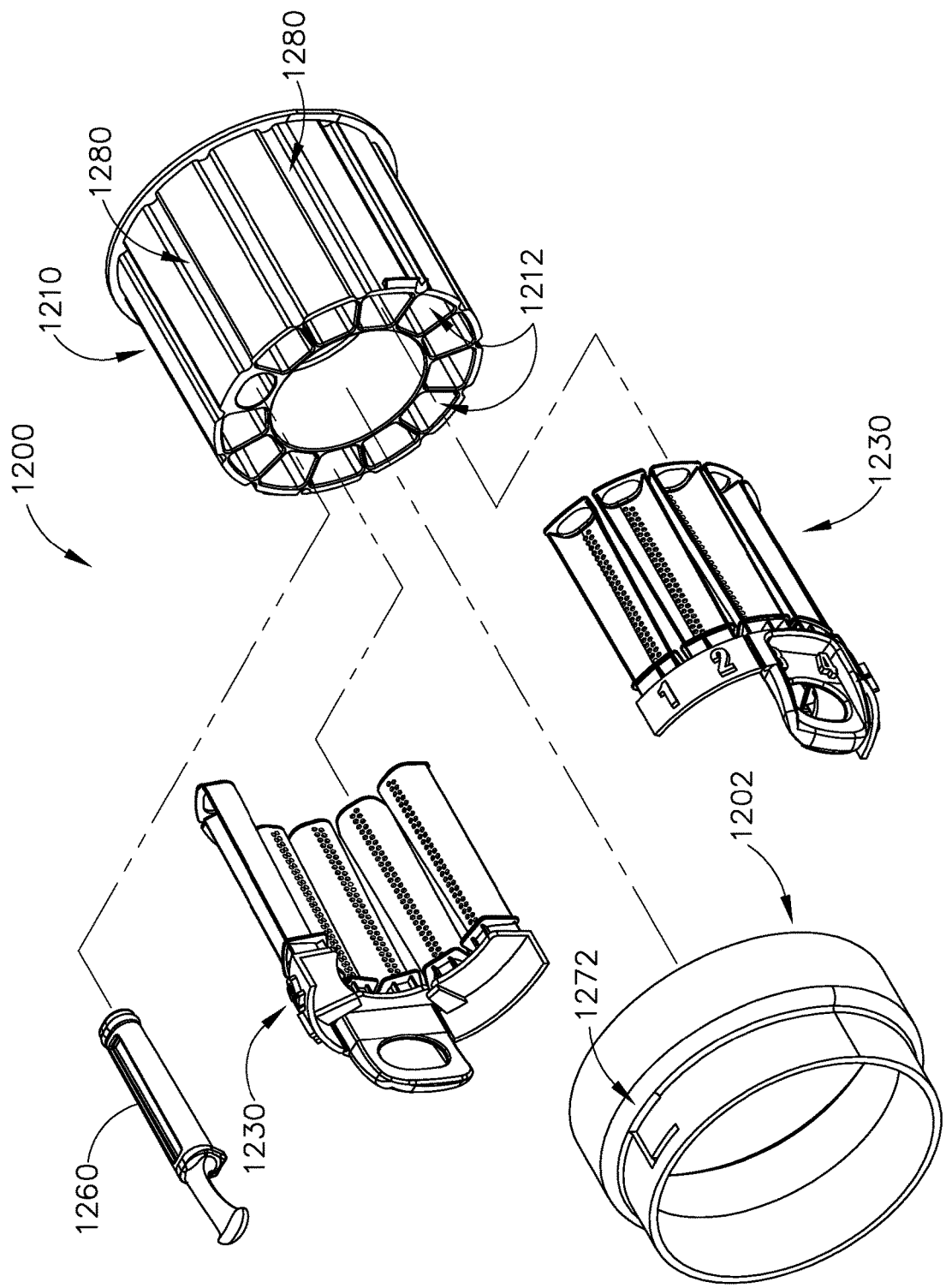
FIG. 34 depicts a perspective exploded view of the tissue sample holder of FIG. 33.

As can best be seen in FIG. 34, tissue sample holder (1200) comprises a manifold (1210) and transparent cover (1202). As similarly described above with respect to manifold (310), manifold (1210) is configured to rotate relative to transparent cover (1202) thereby indexing a plurality of passages (1212) containing trays (1230) with cutter lumen (151) of biopsy device (10). In addition to passages (1212), manifold (1210) comprises a single passage (1213) for receipt of a plug (1260) that is substantially the same as plug (360) described above. It should be understood that manifold (1210) and cover (1202) are substantially the same as manifold (310) and cover (302) described above, unless otherwise noted herein.

Like with tissue sample holder (300) described above, tissue sample holder (1200) includes tissue sample holder indexing system (1270). Indexing system (1270) comprises transparent cover (1202) having a resiliently biased tab (1272) which engage a plurality of discrete indexing features (1280) oriented around the circumference of manifold (1210) to bias manifold (1210) toward a plurality of discrete rotational positions, as will be described in further detail below.

Figure 35:
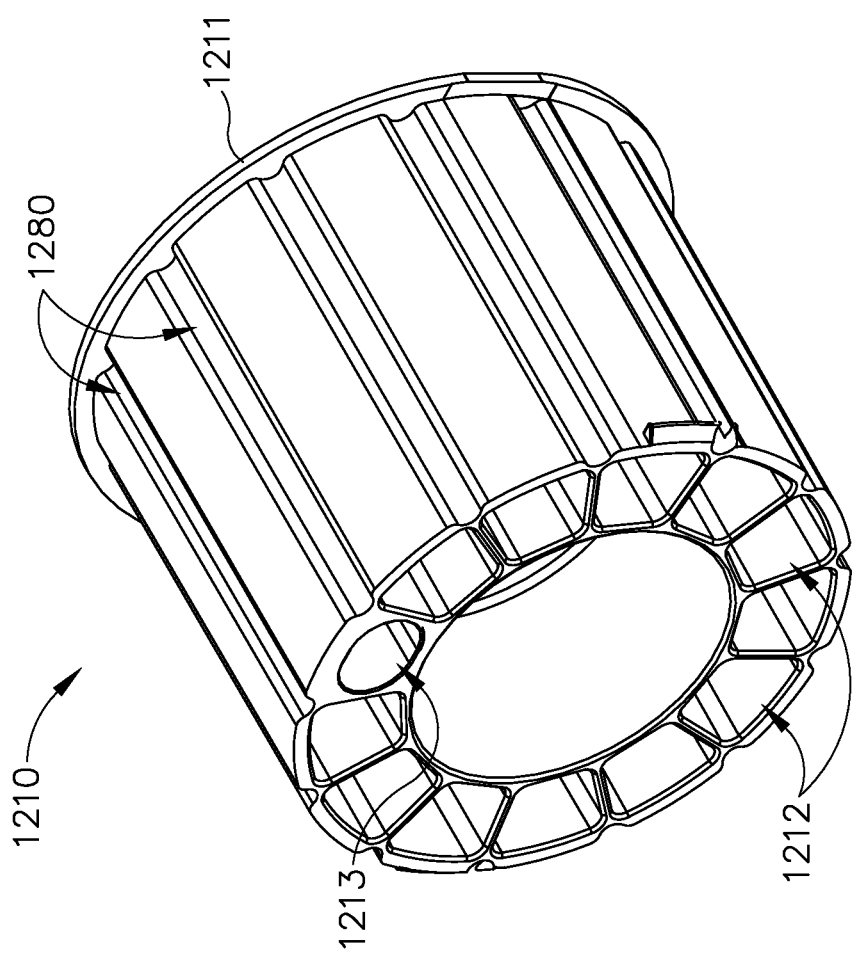
FIG. 35 depicts a perspective view of a manifold of the tissue sample holder of FIG. 33.

As can be seen in FIG. 35, manifold (1210) comprises thirteen discrete indexing features (1380). Each indexing feature (1280) is generally formed as an elongate semi-cylindrical indentation extending inwardly from the exterior surface of manifold (1210). Each indexing feature (1280) extends longitudinally from the distal end of manifold (1210) to a proximal flange (1211). Because of this longitudinal extension, it should be understood that indexing features (1280) may also have the function of providing a grip feature on manifold (1210). Such a feature may be desirable to permit manifold (1210) to be manually rotatable.

Manifold (1210) of the present example has a single indexing feature (1280) corresponding to each passage (1212, 1213). As will be described in further detail below, indexing features (1280) are operable to engage with transparent cover (1202) to urge manifold (1210) relative to transparent cover (1202) to a particular indexing position. It will be appreciated that each indexing feature (1280) may comprise a variety of shapes and/or sizes beyond semi-cylindrical indentations. Additionally, although a plurality of discrete indexing features (1280) is shown, it should be understood that in other examples indexing features (1280) may be connected to each other. In other words, indexing features (1280) may alternatively comprise a single feature of variable depth extending circumferentially around manifold (1210). Of course, other shapes, sizes, and/or configurations of indexing features (1280) will be apparent to those of ordinary skill in the art in view of the teachings herein.

Figure 36:
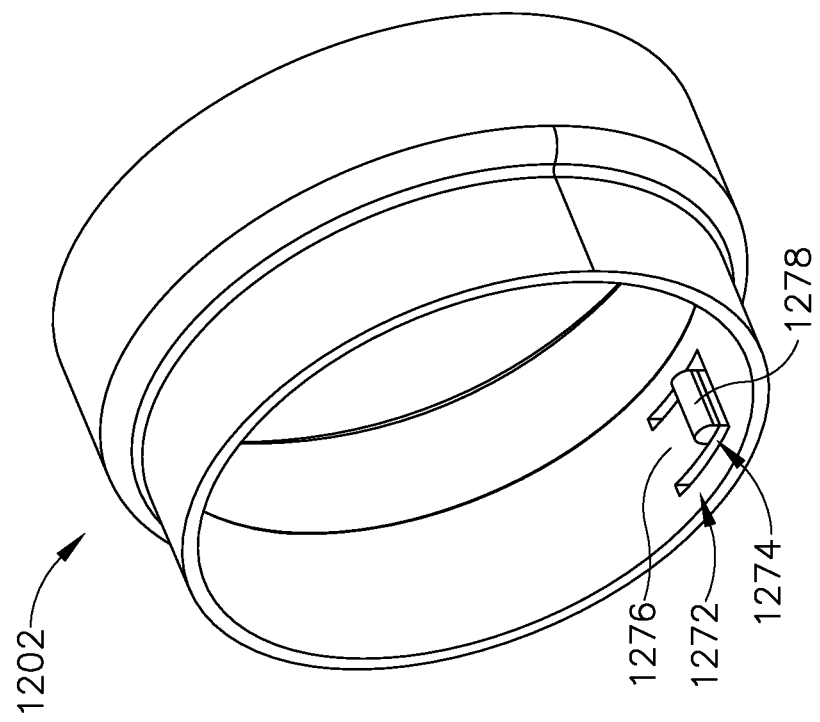
FIG. 36 depicts a perspective view of a transparent cover of the tissue sample holder of FIG. 33.

FIG. 36 shows transparent cover (1202) in greater detail. As can be seen, transparent cover (1202) includes resilient tab (1272), which is of integral construction with transparent cover (1202). In the present example, resilient tab (1272) is defined by a single slot (1274) extending through transparent cover (1202). Resilient tab (1272) comprises a resilient arm (1276) and a manifold engagement portion (1278). Resilient arm (1276) is configured to flex or elastically deform as resilient tab (1272) engages and disengages with indexing features (1218). Manifold engagement portion (1278) extends into the inner diameter of transparent cover (1202) having a generally semi-cylindrical shape. It should be understood that the particular shape of manifold engagement portion (1278) generally corresponds to the particular shape of each indexing feature (1280). Thus, in examples where the shapes of indexing features (1280) are varied, the particular shape of manifold engagement portion (1278) may likewise be varied. As will be understood, the combination of resilient arm (1276) and manifold engagement portion (1278) permits resilient tab (1272) to travel into and out of indexing features (1280) as manifold (1210) is rotated to sequentially bias a particular passage (1212, 1213) of manifold (1210) into alignment cutter lumen (115). Although the present example is shown as having a single resilient tab (1272), it should be understood that in other examples any suitable number of resilient tabs (1272) may be used. Additionally, although resilient tab (1272) is shown in the present example as being integral with transparent cover (1202), in other examples resilient tab (1272) may be a separate component fixedly secured to transparent cover (1202).

Unlike transparent cover (302) described above, transparent cover (1202) only partially covers manifold (1210) when transparent cover (1202) is inserted onto manifold (1210). As can best be seen in FIG. 33, a portion of manifold (1210) is exposed, while a portion of manifold (1210) is disposed within transparent cover (1202). As will be understood, such a configuration may be desirable to permit an operator to use indexing features (1280) as grips for manual rotation of manifold (1210). In other examples, transparent cover (1202) may be configured to expose any suitable amount of manifold (1210). In should be understood that such a feature of transparent cover (1202) is merely optional and in other examples transparent cover (1202) may be configured to completely cover manifold (1210) similarly to transparent cover (302) described above.

Figure 37:
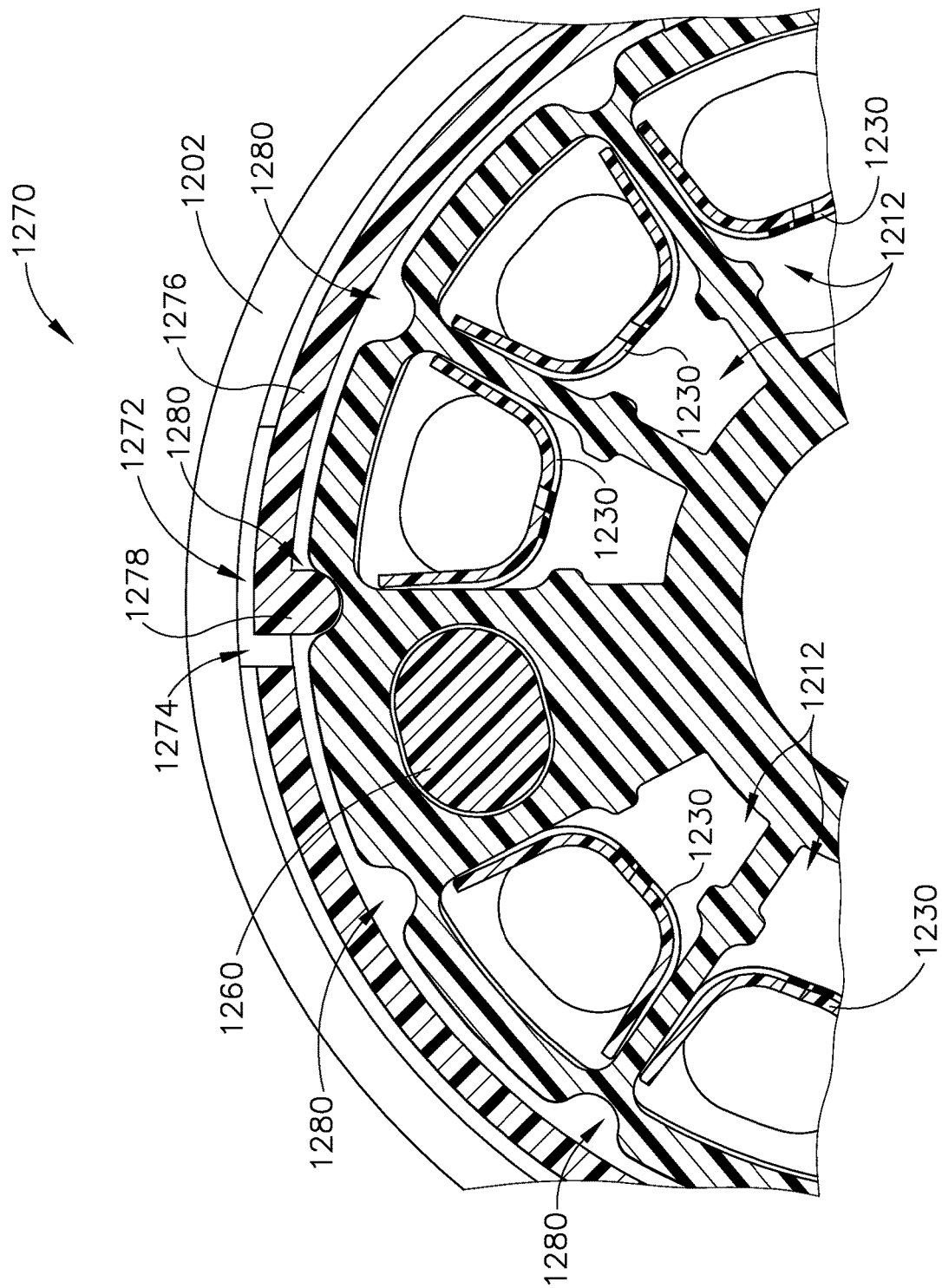
FIG. 37 depicts a partial cross-sectional end view of the tissue sample holder of FIG. 33, with the cross-section taken along line 37-37 of FIG. 33 and the manifold in an indexed position.
Figure 38:
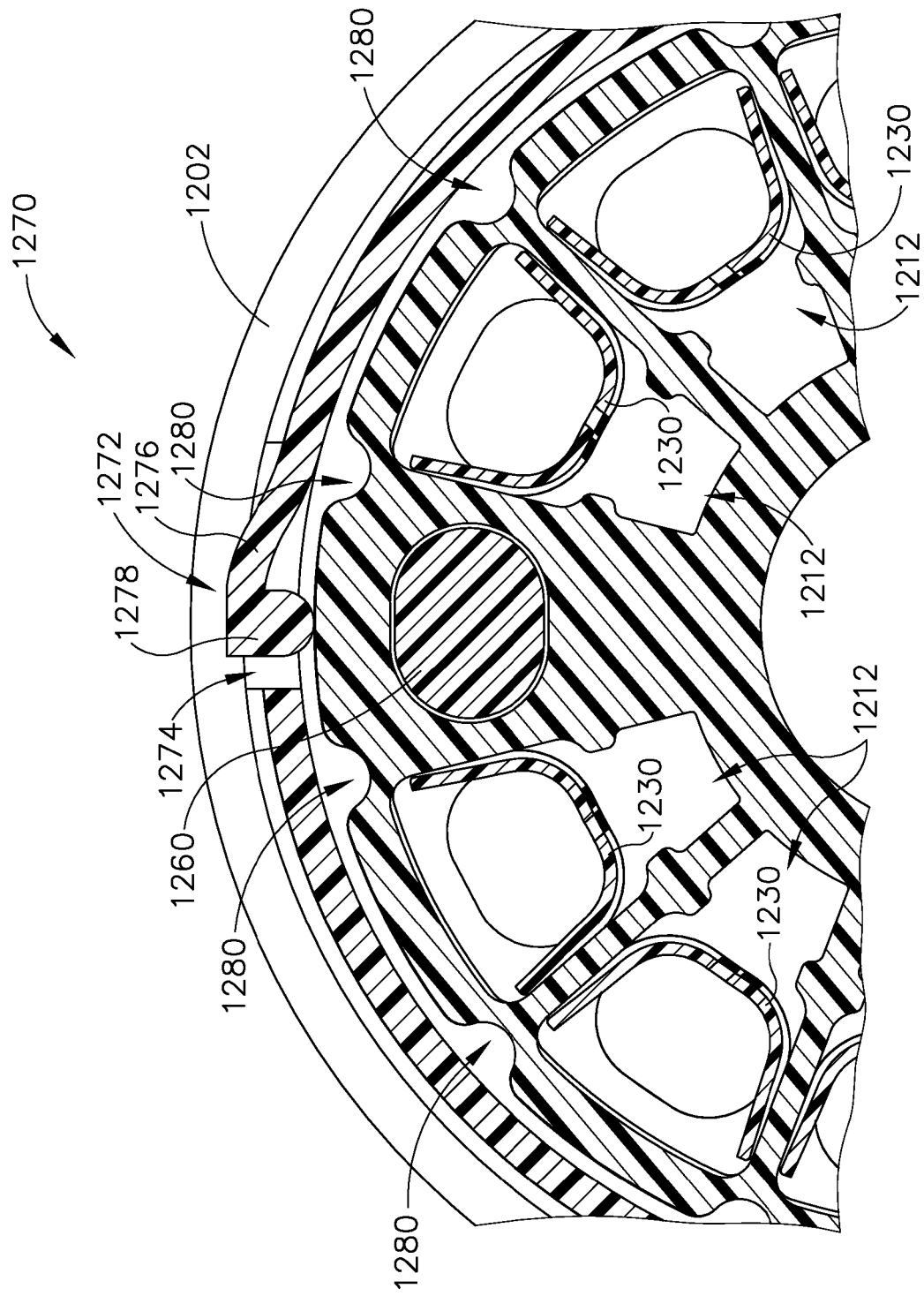
FIG. 38 depicts another partial cross-sectional end view of the tissue sample holder of FIG. 33, with the manifold in an un-indexed position.

FIGS. 37 and 38 show indexing system (1270) in an exemplary mode of operation. Generally, FIG. 37 shows indexing system (1270) in an indexed state, where an individual passage (1212, 1213) of manifold (1210) is aligned with cutter lumen (151). Likewise, FIG. 38 shows indexing system (1270) in an unindexed state where manifold (1210) is in the process of rotating from one passage (1212, 1213) to another passage (1212, 1213). Once manifold (1210) rotates to the position shown in FIG. 37, it may continue to rotate and indexing system (1270) will return to the state shown in FIG. 37 with another passage (1212, 1213) aligned with cutter lumen (151). Accordingly, indexing system (1270) provides an additional mechanism (beyond that provided by grasping feature (184)) to ensure that a particular passage (1212, 1213) is aligned with cutter lumen (151).

As can be seen in FIG. 38, indexing system (1270) is in an indexed state. In the indexed state, manifold engagement portion (1278) of resilient tab (1272) is disposed within a corresponding indexing feature (1280). Additionally, resilient arm (1276) is in a relaxed state, holding manifold engagement portion (1278) within indexing feature (1280) and thereby biasing manifold (1210) in the position shown in FIG. 37.

Indexing system (1270) shifts from the indexed state (FIG. 37) to the unindexed state (FIG. 38) by manifold (1210) rotating relative to transparent cover (1202) via a central shaft (not shown) as similarly described above with respect to manifold (310). As manifold (1210) rotates, the rotational force drives manifold engagement portion (1278) upwardly out of a particular indexing feature (1280). Motion of manifold engagement portion (1278) upwardly is against the resilient bias of resilient arm (1276) such that resilient arm (1276) elastically deforms thereby storing at least some energy within resilient arm (1276).

For manifold (1210) to index another passage (1212, 1213) with cutter lumen (151), manifold (1210) may continue to rotate relative to transparent cover (1202) via the central shaft. Once manifold (1210) is indexed with another passage (1212, 1213), indexing system (1270) will return to the indexed state depicted in FIG. 37 (but with manifold (1210) indexed to a different passage). In particular, as manifold (1210) rotates, the energy stored in resilient arm (1276) will drive manifold engagement portion (1278) downwardly into another indexing feature (1280). Accordingly, such a force causes indexing system (1270) to bias manifold (1210) toward a position where manifold engagement portion (1278) and a particular indexing feature (1280) is aligned. It should be understood that the relative positioning of manifold engagement portion (1278) and each indexing feature (1280) is configured to index a particular passage (1212, 1213) with cutter lumen (115). Thus, when manifold engagement portion (1278) engages with a particular indexing feature (1280), a corresponding passage (1212, 1213) is correspondingly indexed with cutter lumen (115).

It should be understood that the coupling between the central shaft and grasping feature (184) may have some amount of backlash such that the central shaft may move without corresponding movement of grasping feature (184). Thus, while a passage (1212, 1213) of manifold (1210) may be indexed solely by the central shaft and grasping feature (184), indexing system (1270) may be operable to overcome any misindexing caused by backlash between the central shaft and grasping feature (184). Of course, in other versions backlash may be minimal and indexing system (1270) may merely provide a secondary mechanism for indexing passages (1212, 1213) of manifold (1210) with cutter lumen (151). Additionally, in some examples the mechanical motion provided by grasping feature (184) may be eliminated and tissue sample holder (1200) may be configured for manual rotation. In such examples, indexing system (1270) may provide the sole mechanism for indexing passages (1212, 1213) of manifold (1210) with cutter lumen (151). Where manual rotation is utilized (in addition to or in lieu of motion provided by grasping feature (184), it should be understood that indexing features (1280) may also provide a grip feature such that an operator may gasp and rotate manifold (1210) using the portion of indexing features (1280) extending out of transparent cover (1202) for increased grip.

VIII. EXEMPLARY ALTERNATIVE INDEXING SYSTEM WITH PROTRUDING SEMI-CYLINDRICAL INDEXING FEATURE

FIG. 39 shows yet another exemplary alternative tissue sample holder (1300). Tissue sample holder (1300) is substantially the same as tissue sample holder (300) described above, unless otherwise noted herein. For instance, like with tissue sample holder (300), tissue sample holder (1300) is configured to be readily incorporated into biopsy device (10) as described above. Alternatively, tissue sample holder (1300) may be configured for incorporation into any other suitable biopsy device (10). Merely exemplary alternative biopsy devices into which tissue sample holder may be readily incorporated are described in U.S. Pub. No. 2015/0065913, entitled "Tissue Collection Assembly for Biopsy Device," published on Mar. 5, 2015, the disclosure of which is incorporated by reference herein.

As can best be seen in FIG. 40, tissue sample holder (1300) comprises a manifold (1310) and transparent cover (1302). As similarly described above with respect to manifold (310), manifold (1310) is configured to rotate relative to transparent cover (1302) thereby indexing a plurality of passages (1312) containing trays (1330) with cutter lumen (151) of biopsy device (10). In addition to passages (1312), manifold (1310) comprises a single passage (1313) for receipt of a plug (1360) that is substantially the same as plug (360) described above. It should be understood that manifold (1310) and cover (1302) are substantially the same as manifold (310) and cover (302) described above, unless otherwise noted herein.

Like with tissue sample holder (300) described above, tissue sample holder (1300) includes tissue sample holder indexing system (1370). Indexing system (1370) comprises transparent cover (1302) having a resiliently biased tab (1372) which engage a plurality of discrete indexing features (1380) oriented around the circumference of manifold (1310) to bias manifold (1310) toward a plurality of discrete rotational positions, as will be described in further detail below.

Figure 41:
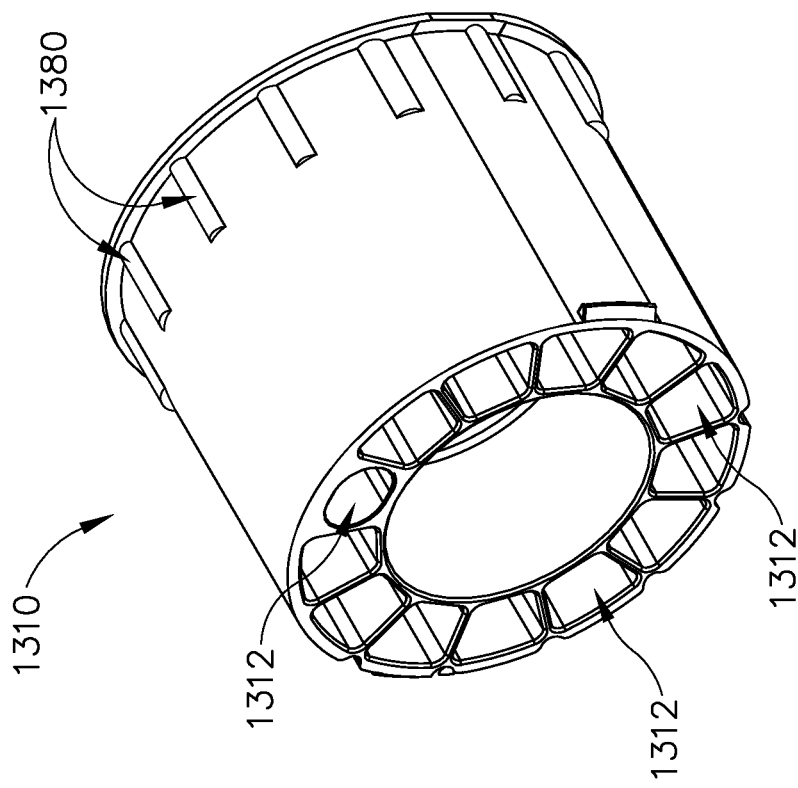
FIG. 41 depicts a perspective view of a manifold of the tissue sample holder of FIG. 39.

As can be seen in FIG. 41, manifold (1310) comprises thirteen discrete indexing features (1380). Each indexing feature (1380) is generally formed as an elongate semi-cylindrical indentation extending outwardly from the exterior surface of manifold (1310). Each indexing feature (1380) extends longitudinally from a proximal flange (1311) partially across the longitudinal length of manifold (1310). Although each indexing feature (1380) is shown as only extending partially across the longitudinal length of manifold (1310), it should be understood that in other examples each indexing feature may extend for the entire longitudinal length of manifold (1310). In such examples, indexing features (1380) may have the function of providing a grip feature on manifold (1310). Such a feature may be desirable to permit manifold (1310) to be manually rotatable.

Manifold (1310) of the present example has a single indexing feature (1380) corresponding to each passage (1312, 1313). As will be described in further detail below, indexing features (1380) are operable to engage with transparent cover (1302) to urge manifold (1310) relative to transparent cover (1302) to a particular indexing position. It will be appreciated that each indexing feature (1380) may comprise a variety of shapes and/or sizes beyond semi-cylindrical indentations. Additionally, although a plurality of discrete indexing features (1380) is shown, it should be understood that in other examples indexing features (1380) may be connected to each other. In other words, indexing features (1380) may alternatively comprise a single feature of variable thickness extending circumferentially around manifold (1310). Of course, other shapes, sizes, and/or configurations of indexing features (1380) will be apparent to those of ordinary skill in the art in view of the teachings herein.

Figure 42:
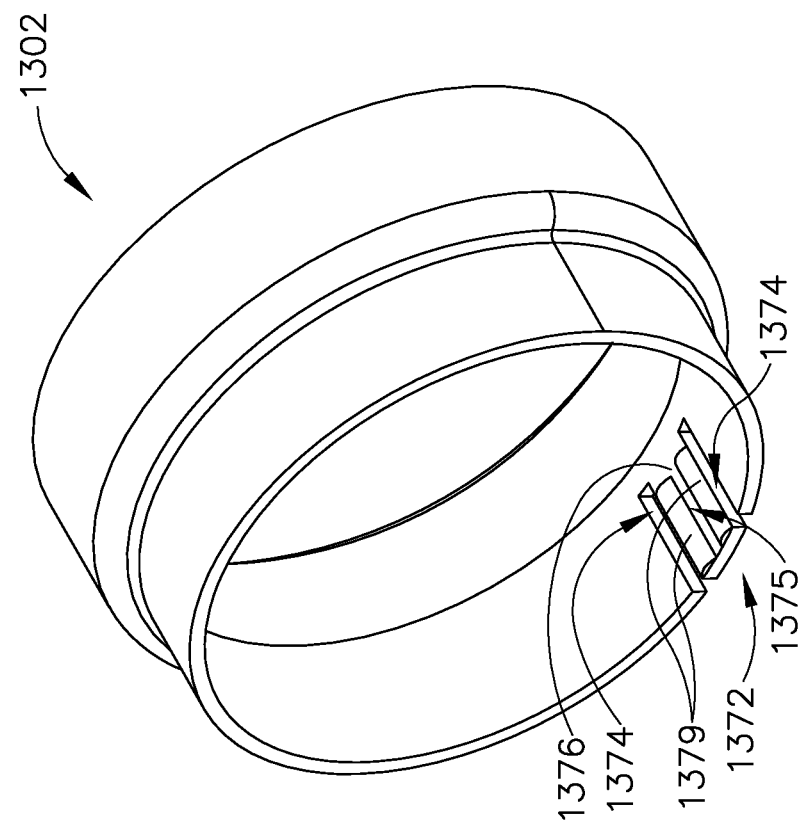
FIG. 42 depicts a perspective view of a transparent cover of the tissue sample holder of FIG. 39.

FIG. 42 shows transparent cover (1302) in greater detail. As can be seen, transparent cover (1302) includes resilient tab (1372), which is of integral construction with transparent cover (1302). In the present example, resilient tab (1372) is defined by two slots (1374) extending through transparent cover (1302). Resilient tab (1372) comprises a resilient arm (1376) and a manifold engagement portion (1278). Resilient arm (1376) is configured to flex or elastically deform as resilient tab (1372) engages and disengages with indexing features (1318). Manifold engagement portion (1378) comprises two parallel protrusions (1379) extending into the inner diameter of transparent cover (1302). Protrusions (1379) comprise a generally semi-cylindrical shape and are spaced from each other a distance corresponding to the size of indexing features (1380) such that the space between each protrusion is configured to receive indexing feature (1380). It should be understood that the particular shape of manifold engagement portion (1378) generally corresponds to the particular shape of each indexing feature (1380). Thus, in examples where the shapes of indexing features (1380) are varied, the particular shape of manifold engagement portion (1378) may likewise be varied. As will be understood, the combination of resilient arm (1376) and manifold engagement portion (1378) permits resilient tab (1372) to engage and disengage from indexing features (1380) as manifold (1310) is rotated to sequentially bias a particular passage (1312, 1313) of manifold (1310) into alignment cutter lumen (115). Although the present example is shown as having a single resilient tab (1372), it should be understood that in other examples any suitable number of resilient tabs (1372) may be used. Additionally, although resilient tab (1372) is shown in the present example as being integral with transparent cover (1302), in other examples resilient tab (1372) may be a separate component fixedly secured to transparent cover (1302).

Unlike transparent cover (302) described above, transparent cover (1302) only partially covers manifold (1310) when transparent cover (1302) is inserted onto manifold (1310). As can best be seen in FIG. 39, a portion of manifold (1310) is exposed, while a portion of manifold (1310) is disposed within transparent cover (1302). As will be understood, such a configuration may be desirable to permit an operator to grip manifold (1310) for manual rotation of manifold (1310). In other examples, transparent cover (1302) may be configured to expose any suitable amount of manifold (1310). In should be understood that such a feature of transparent cover (1302) is merely optional and in other examples transparent cover (1302) may be configured to completely cover manifold (1310) similarly to transparent cover (302) described above. It should be further understood that in still other examples, indexing features (1380) may also extend distally along manifold (1310) such that indexing features (1380) are accessible for use as grips as similarly described above with respect to manifold (1210).

Figure 43:
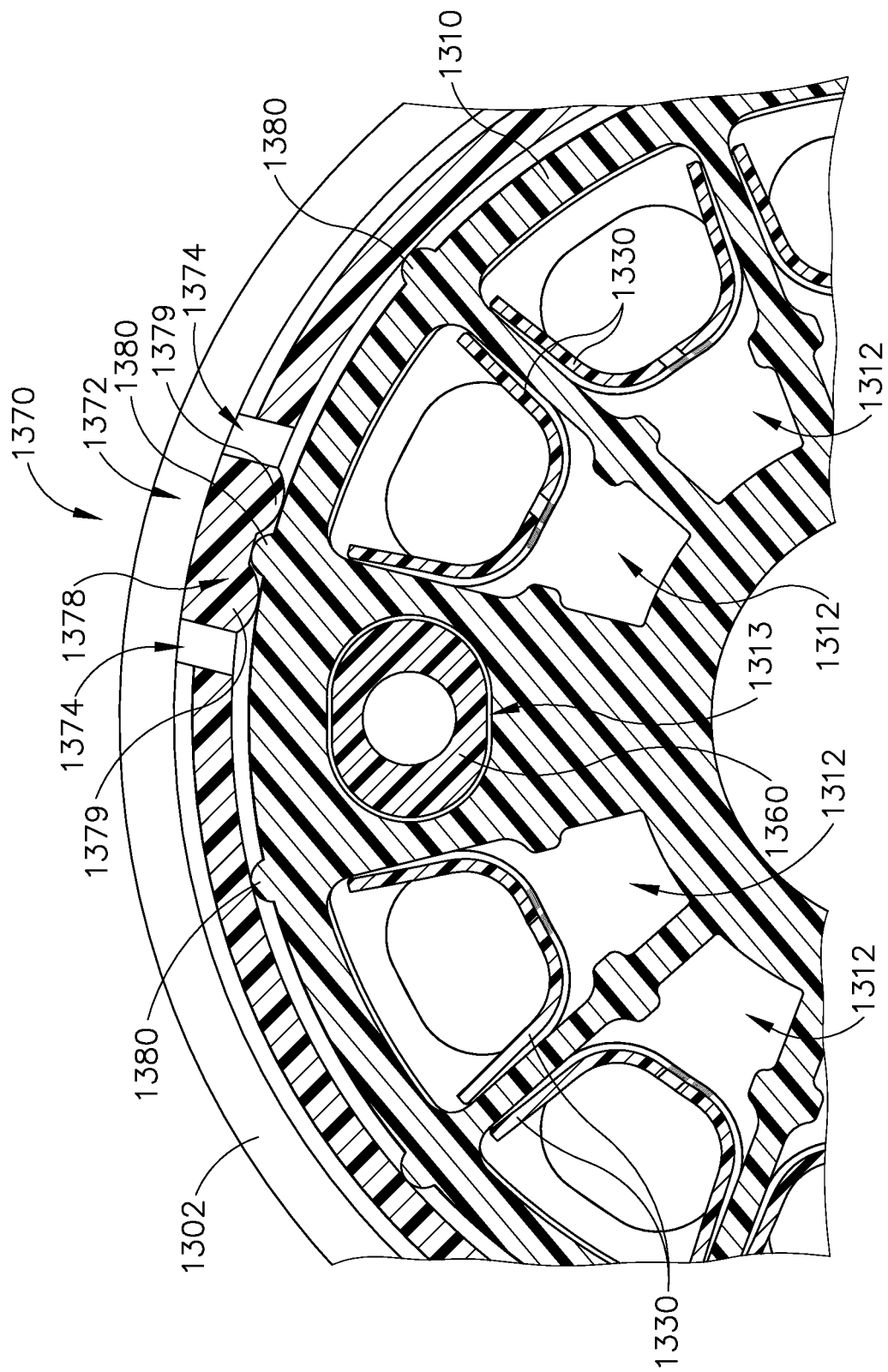
FIG. 43 depicts a partial cross-sectional end view of the tissue sample holder of FIG. 39, with the cross-section taken along line 43-43 of FIG. 39 and the manifold in an indexed position.
Figure 44:
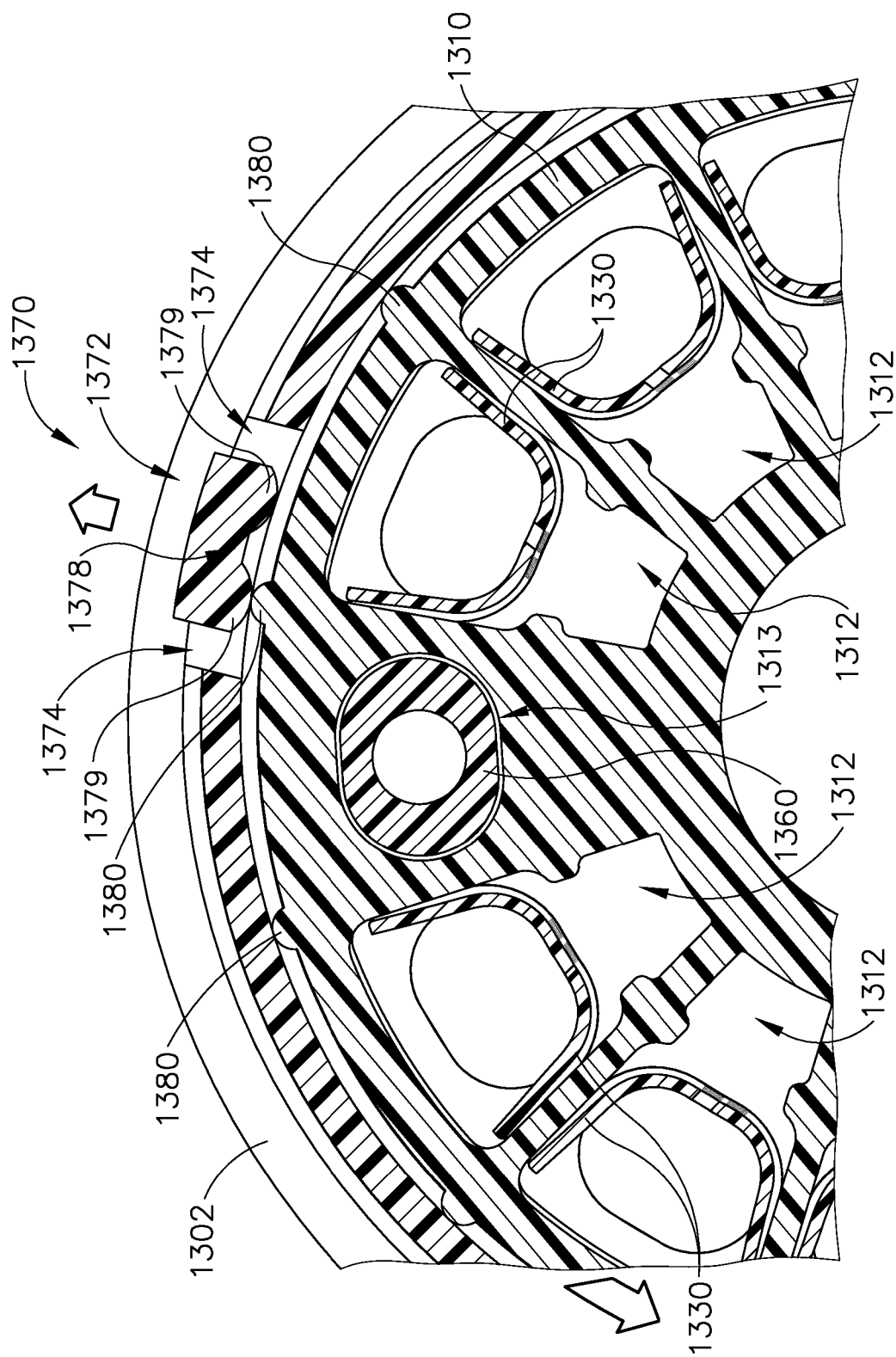
FIG. 44 depicts another partial cross-sectional end view of the tissue sample holder of FIG. 39, with the manifold in an partially un-indexed position.
Figure 45:
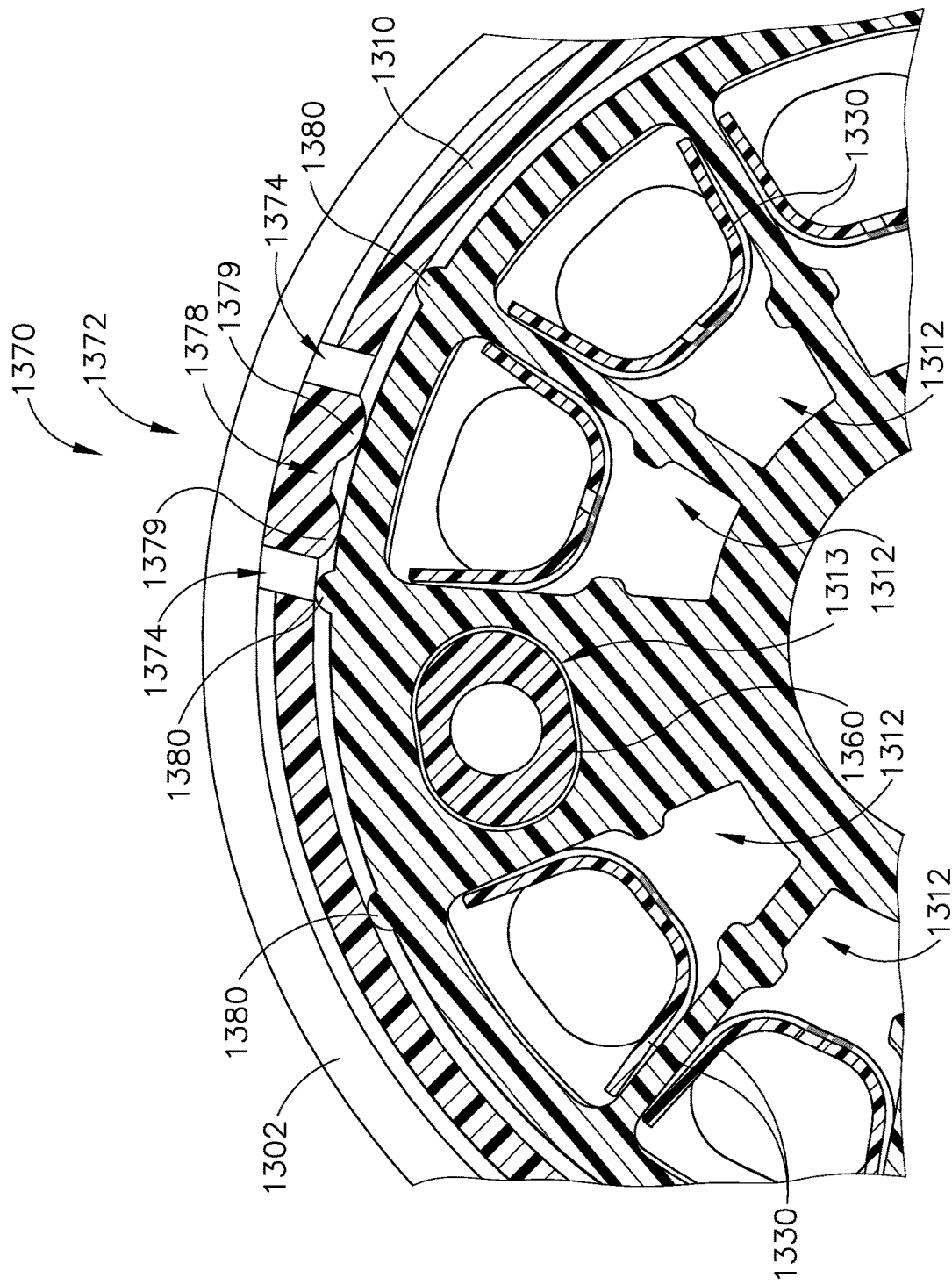
FIG. 45 depicts still another partial cross-sectional end view of the tissue sample holder of FIG. 39, with the manifold in a fully un-indexed position.

FIGS. 43-45 show indexing system (1370) in an exemplary mode of operation. Generally, FIG. 43 shows indexing system (1370) in an indexed state, where an individual passage (1312, 1313) of manifold (1310) is aligned with cutter lumen (151). Likewise, FIGS. 44 and 45 show indexing system (1370) in an unindexed state where manifold (1310) is in the process of rotating from one passage (1312, 1313) to another passage (1312, 1313). Once manifold (1310) rotates to the position shown in FIG. 45, it may continue to rotate and indexing system (1370) will return to the state shown in FIG. 43 with another passage (1312, 1313) aligned with cutter lumen (151). Accordingly, indexing system (1370) provides an additional mechanism (beyond that provided by grasping feature (184)) to ensure that a particular passage (1312, 1313) is aligned with cutter lumen (151).

As can be seen in FIG. 43, indexing system (1370) is in an indexed state. In the indexed state, manifold engagement portion (1378) of resilient tab (1372) is disposed such that a corresponding indexing feature (1380) is engaged between each protrusion (1379). Additionally, resilient arm (1376) is in a relaxed state, holding manifold engagement portion (1378) in engagement with indexing feature (1380) and thereby biasing manifold (1310) in the position shown in FIG. 43.

Indexing system (1370) shifts from the indexed state (FIG. 43) to the unindexed state (FIGS. 44, 45) by manifold (1310) rotating relative to transparent cover (1302) via a central shaft (not shown) as similarly described above with respect to manifold (310). As manifold (1310) rotates, the rotational force drives manifold engagement portion (1378) upwardly out of engagement with a particular indexing feature (1380) as shown in FIG. 44. Motion of manifold engagement portion (1378) upwardly is against the resilient bias of resilient arm (1376) such that resilient arm (1376) elastically deforms thereby storing at least some energy within resilient arm (1376).

For manifold (1310) to index another passage (1312, 1313) with cutter lumen (151), manifold (1310) may continue to rotate relative to transparent cover (1302) via the central shaft. Once manifold (1310) is indexed with another passage (1312, 1313), indexing system (1370) will return to the indexed state depicted in FIG. 43 (but with manifold (1310) indexed to a different passage). In particular, as manifold (1310) rotates, the energy stored in resilient arm (1376) will drive manifold engagement portion (1378) downwardly into engagement with another indexing feature (1380). Accordingly, such a force causes indexing system (1370) to bias manifold (1310) toward a position where manifold engagement portion (1378) and a particular indexing feature (1380) is aligned. It should be understood that the relative positioning of manifold engagement portion (1378) and each indexing feature (1380) is configured to index a particular passage (1312, 1313) with cutter lumen (115). Thus, when manifold engagement portion (1378) engages with a particular indexing feature (1380), a corresponding passage (1312, 1313) is correspondingly indexed with cutter lumen (115).

It should be understood that the coupling between the central shaft and grasping feature (184) may have some amount of backlash such that the central shaft may move without corresponding movement of grasping feature (184). Thus, while a passage (1312, 1313) of manifold (1310) may be indexed solely by the central shaft and grasping feature (184), indexing system (1370) may be operable to overcome any misindexing caused by backlash between the central shaft and grasping feature (184). Of course, in other versions backlash may be minimal and indexing system (1370) may merely provide a secondary mechanism for indexing passages (1312, 1313) of manifold (1310) with cutter lumen (151). Additionally, in some examples the mechanical motion provided by grasping feature (184) may be eliminated and tissue sample holder (1300) may be configured for manual rotation. In such examples, indexing system (1370) may provide the sole mechanism for indexing passages (1312, 1313) of manifold (1310) with cutter lumen (151). Where manual rotation is utilized (in addition to or in lieu of motion provided by grasping feature (184), it should be understood that an operator may gasp and rotate manifold (1310) via the portion of manifold (1310) extending out of transparent cover (1302).

IX. EXEMPLARY ALTERNATIVE INDEXING SYSTEM WITH COMPOUND TRIANGULAR INDEXING FEATURES

Figure 46:
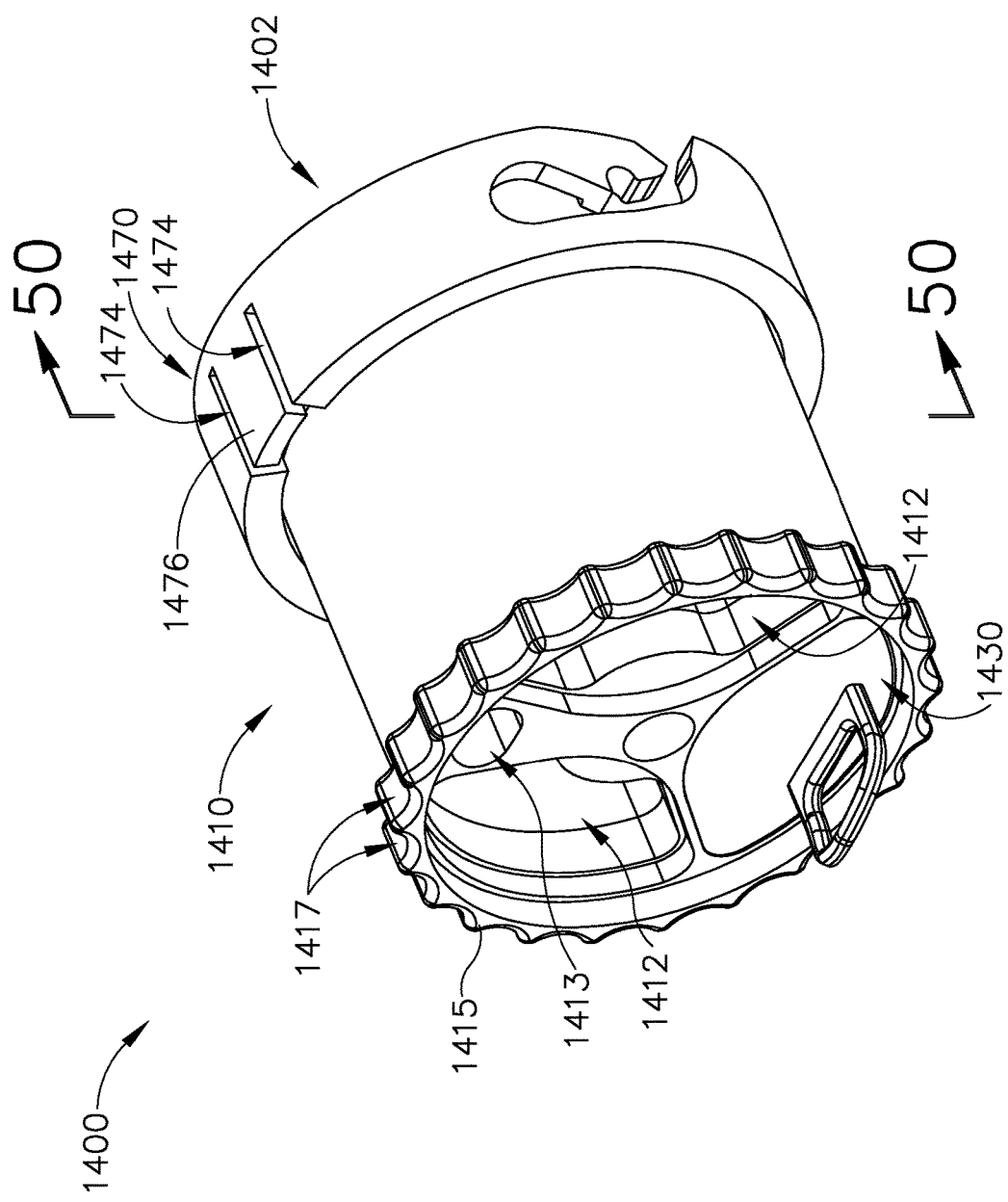
FIG. 46 depicts a perspective view of yet another tissue sample holder for incorporation into the probe of FIG. 4.

FIG. 46 shows yet another exemplary alternative tissue sample holder (1400). Tissue sample holder (1400) is substantially the same as tissue sample holder (300) described above, unless otherwise noted herein. For instance, like with tissue sample holder (300), tissue sample holder (1400) is configured to be readily incorporated into biopsy device (10) as described above. Alternatively, tissue sample holder (1400) may be configured for incorporation into any other suitable biopsy device (10). Merely exemplary alternative biopsy devices into which tissue sample holder may be readily incorporated are described in U.S. Pub. No. 2015/0065913, entitled "Tissue Collection Assembly for Biopsy Device," published on Mar. 5, 2015, the disclosure of which is incorporated by reference herein.

Figure 47:
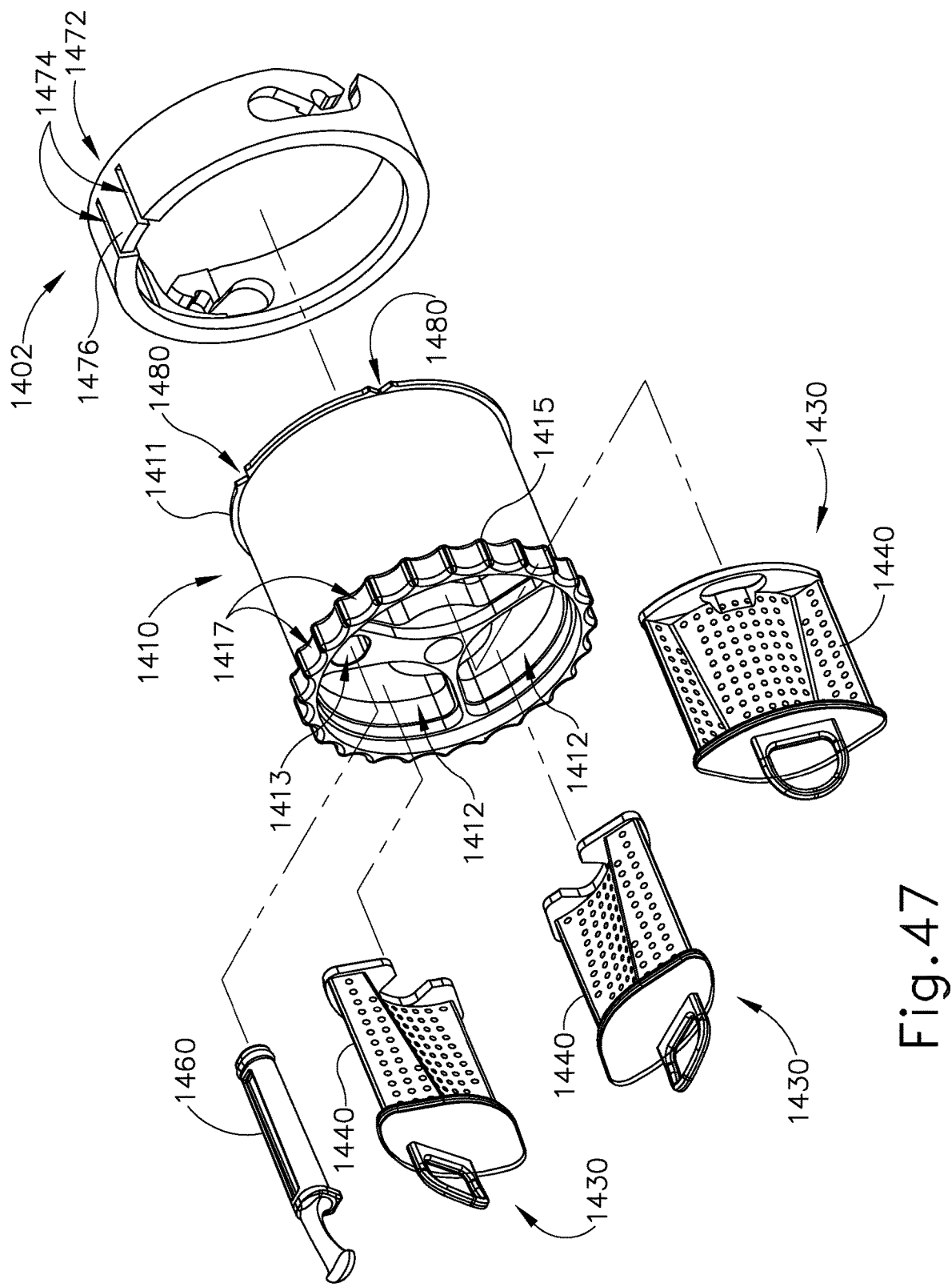
FIG. 47 depicts a perspective exploded view of the tissue sample holder of FIG. 46.

As can best be seen in FIG. 47, tissue sample holder (1400) comprises a manifold (1410) and transparent cover (1402). As similarly described above with respect to manifold (310), manifold (1410) is configured to rotate relative to transparent cover (1402) thereby indexing a plurality of passages (1412) containing trays (1430) with cutter lumen (151) of biopsy device (10). However, unlike manifold (310) described above, manifold (1410) of the present example comprises three passages (1412) instead of twelve. Accordingly, each tray (1430) of the present example is configured to be slidably disposed in a respective passage (1412). Additionally, each tray comprises a single strip (1440) instead of a plurality as with trays (330) described above. In some examples, such a configuration may be desirable to permit each strip (1440) to receive a plurality of tissue samples instead of just a single tissue sample as described above with respect to strips (340). It should be understood that in some examples, trays (1430) may be constructed in accordance with at least some of the teachings of U.S. Pub. No. 2015/0065913, entitled "Tissue Collection Assembly for Biopsy Device," published on Mar. 5, 2015, the disclosure of which is incorporated by reference herein.

Manifold (1410) further comprises a grip flange (1415). Grip flange (1415) extends outwardly from the outer diameter of the proximal end of manifold (1410). Generally, grip flange (1415) is configured to permit an operator to grip manifold (1410) to manually rotate manifold (1410). In particular, grip flange (1415) includes a plurality of indentations (1417) extending circularly around the outer diameter of grip flange (1415). It should be understood that indentations (1417) are configured to enhance the grippability characteristics of grip flange (1415). Although each indentation (1417) is shown as being semi-cylindraceous, it should be understood that in other examples indentations (1417) may have any suitable configuration such as knurled, hemispherical, and/or etc.

In addition to passages (1412), manifold (1410) comprises a single passage (1413) for receipt of a plug (1460) that is substantially the same as plug (360) described above. It should be understood that manifold (1410) and cover (1402) are substantially the same as manifold (310) and cover (302) described above, unless otherwise noted herein.

Like with tissue sample holder (300) described above, tissue sample holder (1400) includes tissue sample holder indexing system (1470). Indexing system (1470) comprises transparent cover (1402) having a resiliently biased tab (1472) which engage a plurality of discrete indexing features (1480) oriented around the circumference of manifold (1410) to bias manifold (1410) toward a plurality of discrete rotational positions, as will be described in further detail below.

Figure 48:
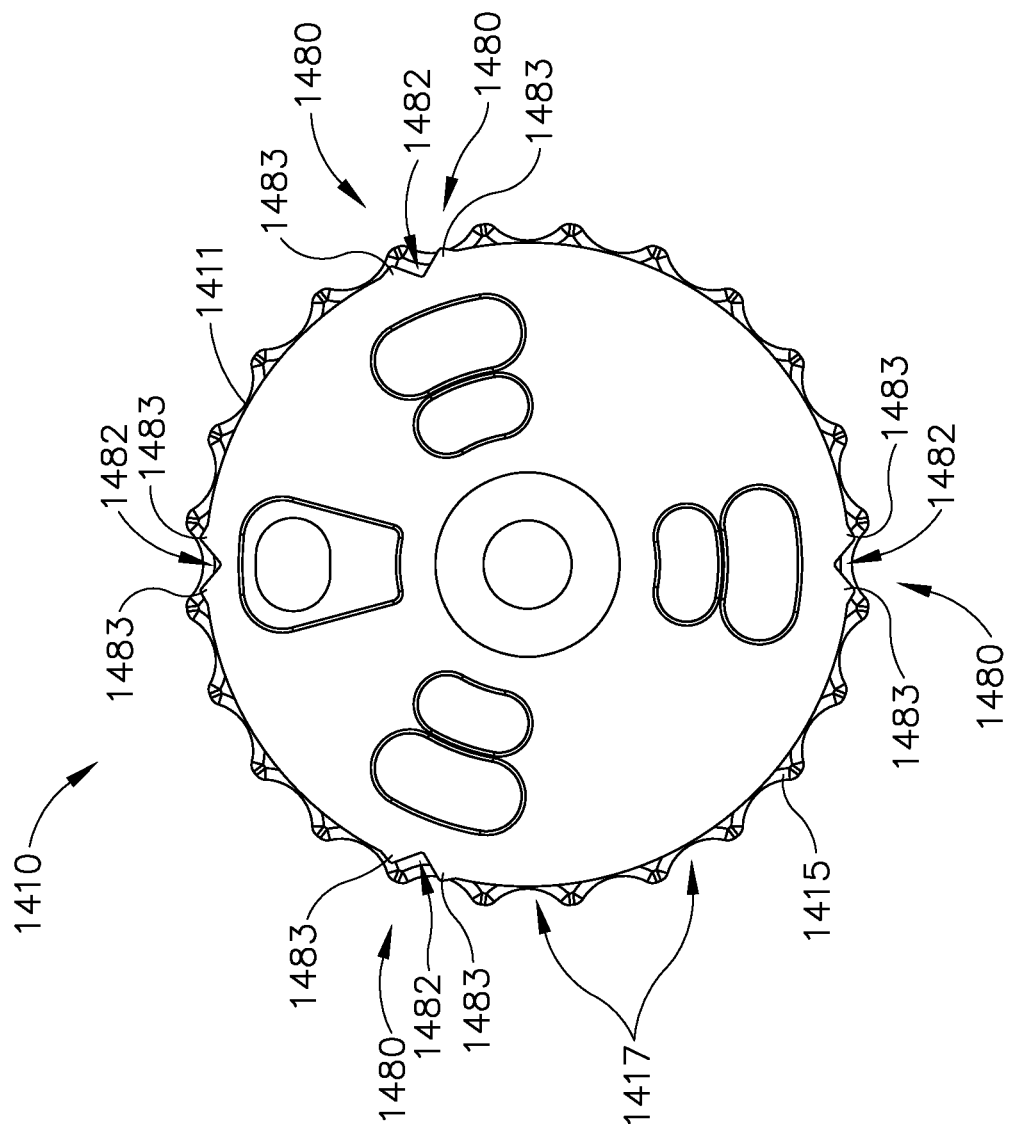
FIG. 48 depicts a an end view of a manifold of the tissue sample holder of FIG. 46.

As can be seen in FIG. 48, manifold (1410) comprises a plurality of discrete indexing features (1480). Each indexing feature (1480) is generally formed a triangular indentation (1482) and a pair of outwardly extending protrusions (1483). Each triangular indentation (1482) is disposed in a flange (1411) on the distal end of manifold (1410). Triangular indentation (1482) further extends entirely through proximal flange (1411) and partially into the outer diameter of manifold (1410). One each side of each of each triangular indentation of indexing feature. Each protrusion (1483) protrudes outwardly from the outer diameter of flange (1411) on each side of triangular indentation (1482). As will be described in greater detail below, each triangular indentation (1482) is generally configured to receive at least a portion of transparent cover (1402) to thereby index manifold (1410) into a given position. As will also be described in greater detail below, protrusions (1483) are generally configured to engage with at least a portion of transparent cover (1402) to provide tactile feedback to an operator when manifold (1410) is rotated relative to transparent cover (1402) manually.

Manifold (1410) of the present example has a single indexing feature (1480) corresponding to each passage (1412, 1413). As will be described in further detail below, indexing features (1480) are operable to engage with transparent cover (1402) to urge manifold (1410) relative to transparent cover (1402) to a particular indexing position. It will be appreciated that each indexing feature (1480) may comprise a variety of shapes and/or sizes beyond semi-cylindrical indentations. Additionally, although a plurality of discrete indexing features (1480) is shown, it should be understood that in other examples indexing features (1480) may be connected to each other. In other words, indexing features (1480) may alternatively comprise a single feature of variable thickness extending circumferentially around manifold (1410). Of course, other shapes, sizes, and/or configurations of indexing features (1480) will be apparent to those of ordinary skill in the art in view of the teachings herein.

Figure 49:
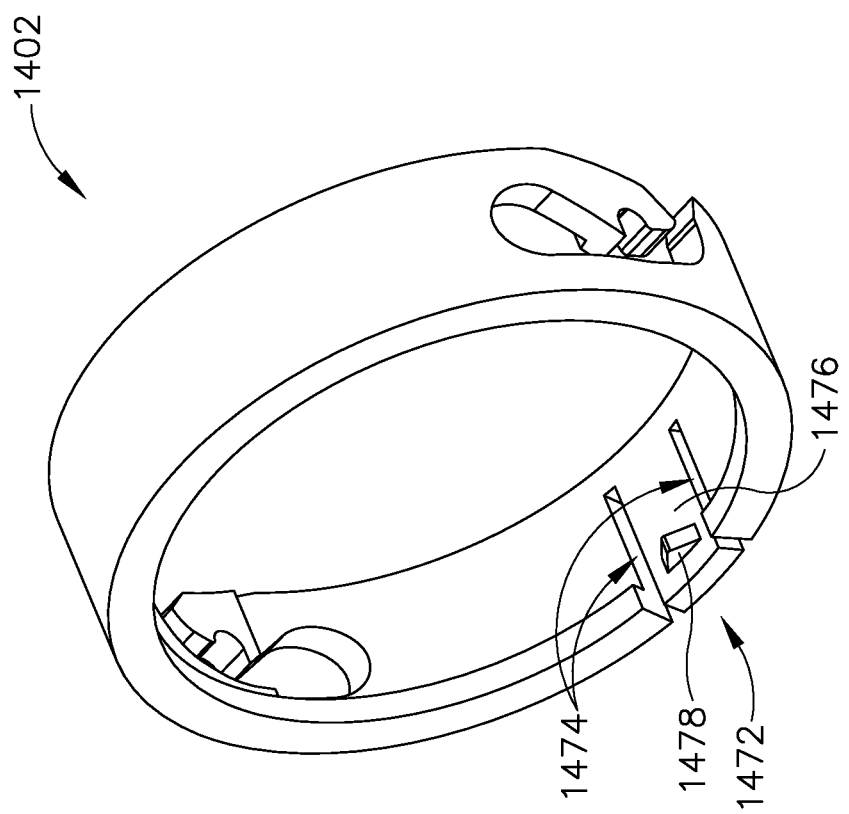
FIG. 49 depicts a perspective view of a transparent cover of the tissue sample holder of FIG. 46.

FIG. 49 shows transparent cover (1402) in greater detail. As can be seen, transparent cover (1402) includes resilient tab (1472), which is of integral construction with transparent cover (1402). In the present example, resilient tab (1472) is defined by two slots (1474) extending through transparent cover (1402). Resilient tab (1472) comprises a resilient arm (1476) and a manifold engagement portion (1478). Resilient arm (1476) is configured to flex or elastically deform as resilient tab (1472) engages and disengages with indexing features (1480). Manifold engagement portion (1478) comprises a single discrete triangular protrusion extending into the inner diameter of transparent cover (1402). It should be understood that the particular shape of manifold engagement portion (1478) generally corresponds to the particular shape of each indexing features (1480). Thus, in examples where the shapes of indexing features (1480) are varied, the particular shape of manifold engagement portion (1478) may likewise be varied. As will be understood, the combination of resilient arm (1476) and manifold engagement portion (1478) permits resilient tab (1472) to engage and disengage from indexing features (1480) as manifold (1410) is rotated to sequentially bias a particular passage (1412, 1413) of manifold (1410) into alignment cutter lumen (115). Although the present example is shown as having a single resilient tab (1472), it should be understood that in other examples any suitable number of resilient tabs (1472) may be used. Additionally, although resilient tab (1472) is shown in the present example as being integral with transparent cover (1402), in other examples resilient tab (1472) may be a separate component fixedly secured to transparent cover (1402).

Unlike transparent cover (302) described above, transparent cover (1402) only partially covers manifold (1410) when transparent cover (1402) is inserted onto manifold (1410). As can best be seen in FIG. 46, a portion of manifold (1410) is exposed, while a portion of manifold (1410) is disposed within transparent cover (1402). In the present example, the proximal end of manifold (1410) extends out of transparent cover (1402) such that grip flange (1415) is accessible while transparent cover (1402) is disposed on manifold (1410). As will be understood, such a configuration may be desirable to permit an operator to grip manifold (1410) via grip flange (1415) for manual rotation of manifold (1410). In other examples, transparent cover (1402) may be configured to expose any suitable amount of manifold (1410). In should be understood that such a feature of transparent cover (1402) is merely optional and in other examples transparent cover (1402) may be configured to completely cover manifold (1410) with only grip flange (1415) protruding from transparent cover (1402).

Figure 50:
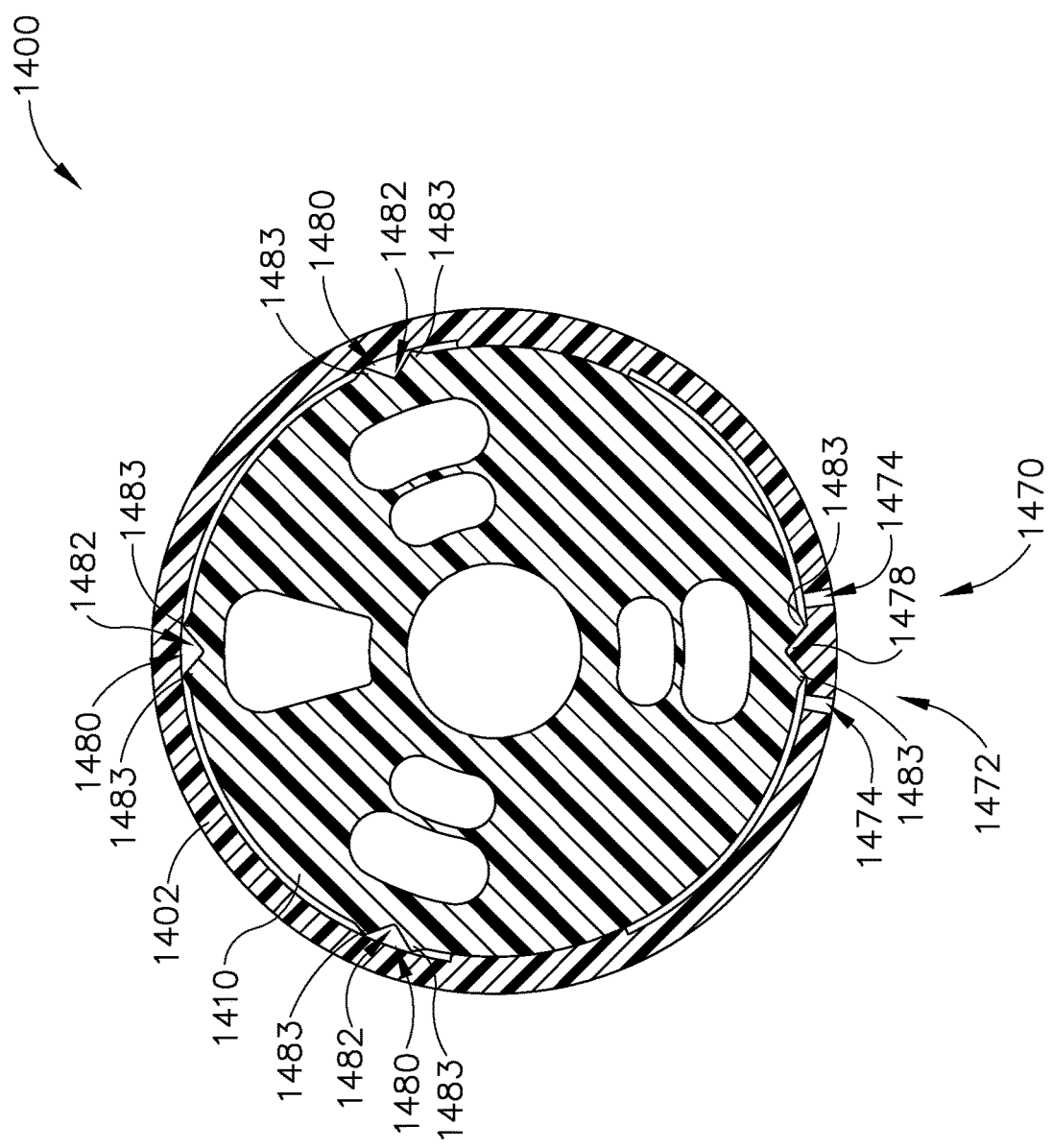
FIG. 50 depicts a cross-sectional view of the tissue sample holder of FIG. 46, with the cross-section taken along line 50-50 of FIG. 46 and the manifold in an indexed position.
Figure 51:
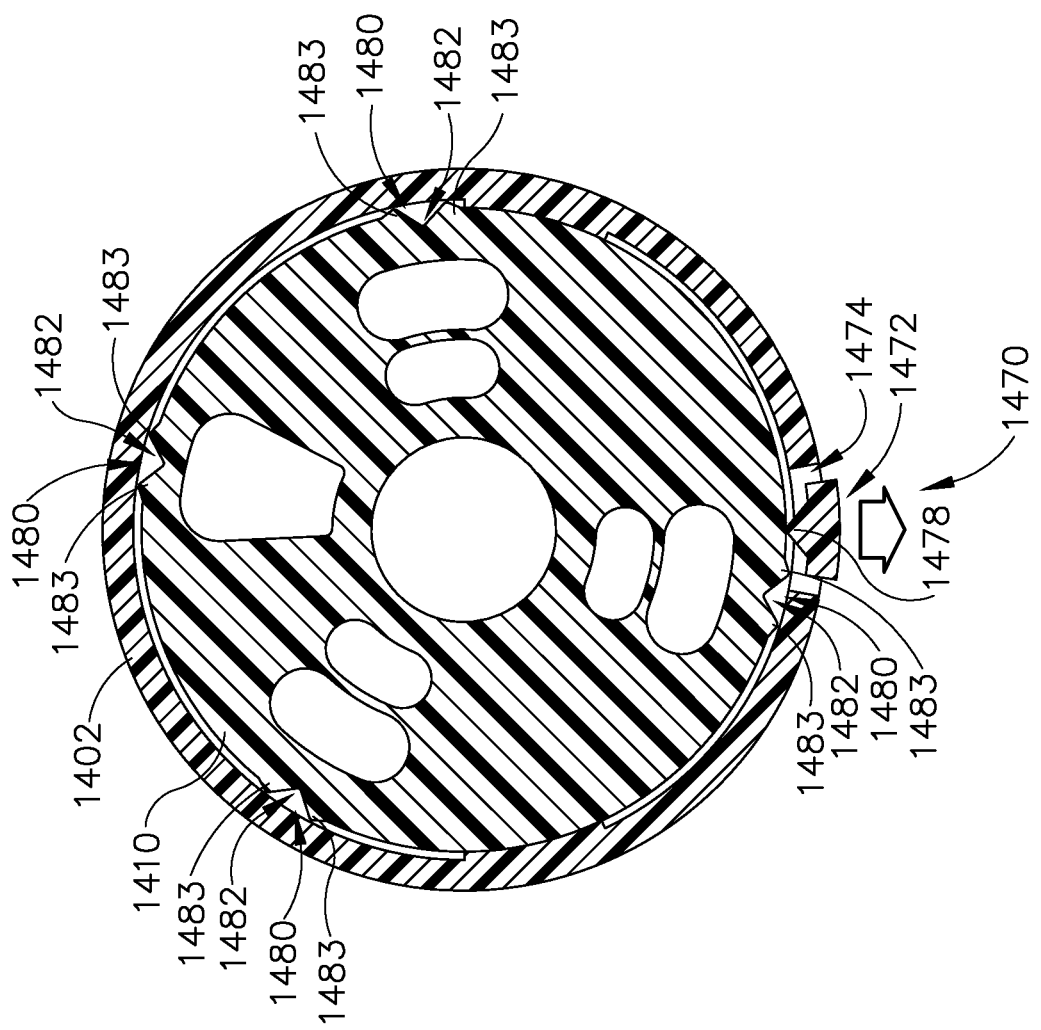
FIG. 51 depicts another cross-sectional view of the tissue sample holder of FIG. 46, with the manifold in an un-indexed position.

FIGS. 50-51 show indexing system (1470) in an exemplary mode of operation. Generally, FIG. 50 shows indexing system (1470) in an indexed state, where an individual passage (1412, 1413) of manifold (1410) is aligned with cutter lumen (151). Likewise, FIG. 51 shows indexing system (1470) in an unindexed state where manifold (1410) is in the process of rotating from one passage (1412, 1413) to another passage (1412, 1413). Once manifold (1410) rotates to the position shown in FIG. 51, it may continue to rotate and indexing system (1470) will return to the state shown in FIG. 50 with another passage (1412, 1413) aligned with cutter lumen (151). Accordingly, indexing system (1470) provides an additional mechanism (beyond that provided by grasping feature (184)) to ensure that a particular passage (1412, 1413) is aligned with cutter lumen (151).

As can be seen in FIG. 50, indexing system (1470) is in an indexed state. In the indexed state, manifold engagement portion (1478) of resilient tab (1472) is disposed such that a corresponding indexing feature (1480) is disposed about manifold engagement portion (1478). Additionally, resilient arm (1476) is in a relaxed state, holding manifold engagement portion (1478) in engagement with indexing feature (1480) and thereby biasing manifold (1410) in the position shown in FIG. 50.

Indexing system (1470) shifts from the indexed state (FIG. 50) to the unindexed state (FIG. 51) by manifold (1410) rotating relative to transparent cover (1402) via a central shaft (not shown) as similarly described above with respect to manifold (310). As manifold (1410) rotates, the rotational force drives manifold engagement portion (1478) upwardly out of engagement with a particular indexing feature (1480). Motion of manifold engagement portion (1478) upwardly is against the resilient bias of resilient arm (1476) such that resilient arm (1476) elastically deforms thereby storing at least some energy within resilient arm (1476).

For manifold (1410) to index another passage (1412, 1413) with cutter lumen (151), manifold (1410) may continue to rotate relative to transparent cover (1402) via the central shaft. In examples where manifold (1410) is manually rotated via grip flange (1415), an operator will encounter tactile feedback as manifold engagement portion (1478) travels over protrusions (1483) of indexing feature (1480) and into triangular indentation (1482) of indexing feature (1480). Once manifold (1410) is indexed with another passage (1412, 1413), indexing system (1470) will return to the indexed state depicted in FIG. 50 (but with manifold (1410) indexed to a different passage (1412, 1413)). In particular, as manifold (1410) rotates, the energy stored in resilient arm (1476) will drive manifold engagement portion (1478) downwardly into engagement with another indexing feature (1480). Accordingly, such a force causes indexing system (1470) to bias manifold (1410) toward a position where manifold engagement portion (1478) and a particular indexing feature (1480) is aligned. It should be understood that the relative positioning of manifold engagement portion (1478) and each indexing feature (1480) is configured to index a particular passage (1412, 1413) with cutter lumen (115). Thus, when manifold engagement portion (1478) engages with a particular indexing feature (1480), a corresponding passage (1412, 1413) is correspondingly indexed with cutter lumen (115).

It should be understood that the coupling between the central shaft and grasping feature (184) may have some amount of backlash such that the central shaft may move without corresponding movement of grasping feature (184). Thus, while a passage (1412, 1413) of manifold (1410) may be indexed solely by the central shaft and grasping feature (184), indexing system (1470) may be operable to overcome any misindexing caused by backlash between the central shaft and grasping feature (184). Of course, in other versions backlash may be minimal and indexing system (1470) may merely provide a secondary mechanism for indexing passages (1412, 1413) of manifold (1410) with cutter lumen (151). Additionally, in some examples the mechanical motion provided by grasping feature (184) may be eliminated and tissue sample holder (1400) may be configured for manual rotation exclusively by grip flange (1415). In such examples, indexing system (1470) may provide the sole mechanism for indexing passages (1412, 1413) of manifold (1410) with cutter lumen (151). Where manual rotation is utilized (in addition to or in lieu of motion provided by grasping feature (184), it should be understood that an operator may gasp and rotate manifold (1510) via grip flange (1415).

X. EXEMPLARY ALTERNATIVE INDEXING SYSTEM WITH LATERALLY EXTENDING CYLINDRICAL INDEXING FEATURES

Figure 52:
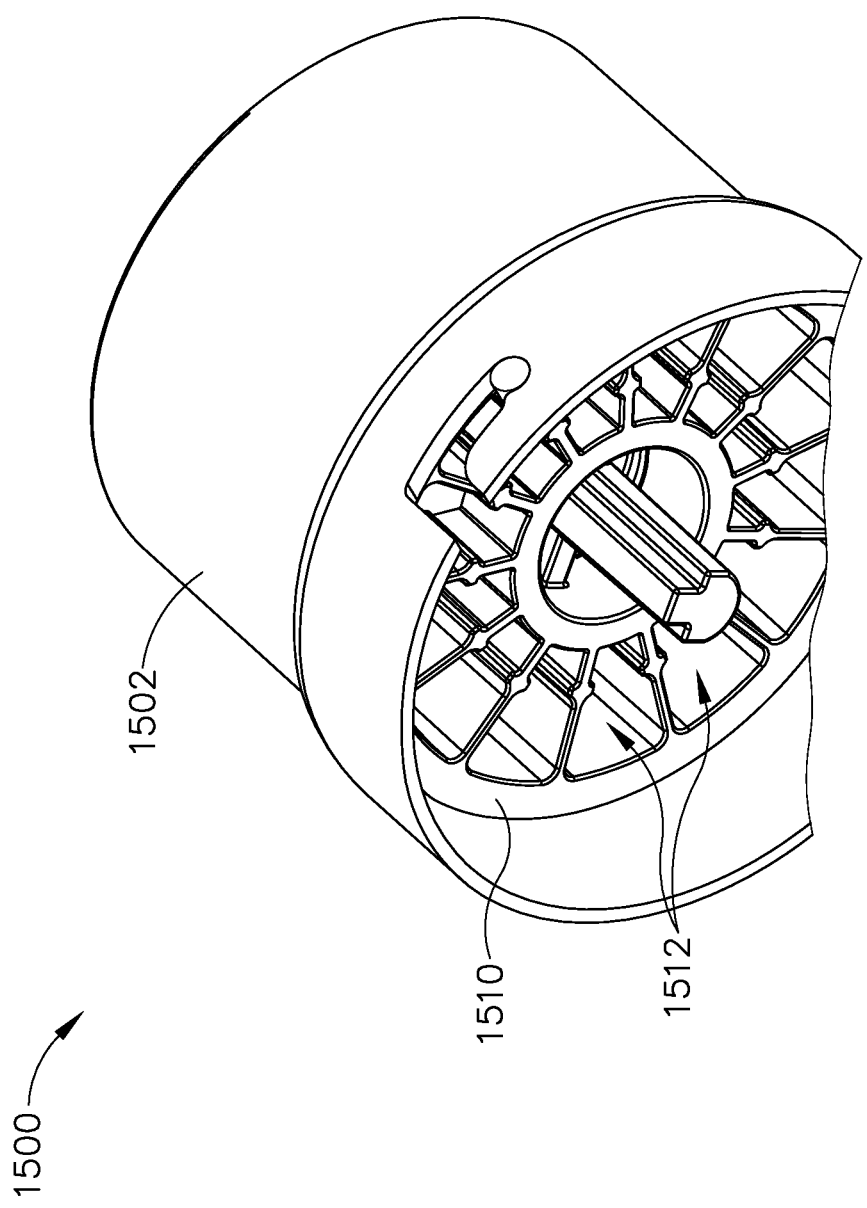
FIG. 52 depicts a perspective view of a yet another tissue sample holder for incorporation into the probe of FIG. 4.

FIG. 52 shows yet another exemplary alternative tissue sample holder (1500). Tissue sample holder (1500) is substantially the same as tissue sample holder (300) described above, unless otherwise noted herein. For instance, like with tissue sample holder (300), tissue sample holder (1500) is configured to be readily incorporated into biopsy device (10) as described above. Alternatively, tissue sample holder (1500) may be configured for incorporation into any other suitable biopsy device (10). Merely exemplary alternative biopsy devices into which tissue sample holder may be readily incorporated are described in U.S. Pub. No. 2015/0065913, entitled "Tissue Collection Assembly for Biopsy Device," published on Mar. 5, 2015, the disclosure of which is incorporated by reference herein.

Figure 54:
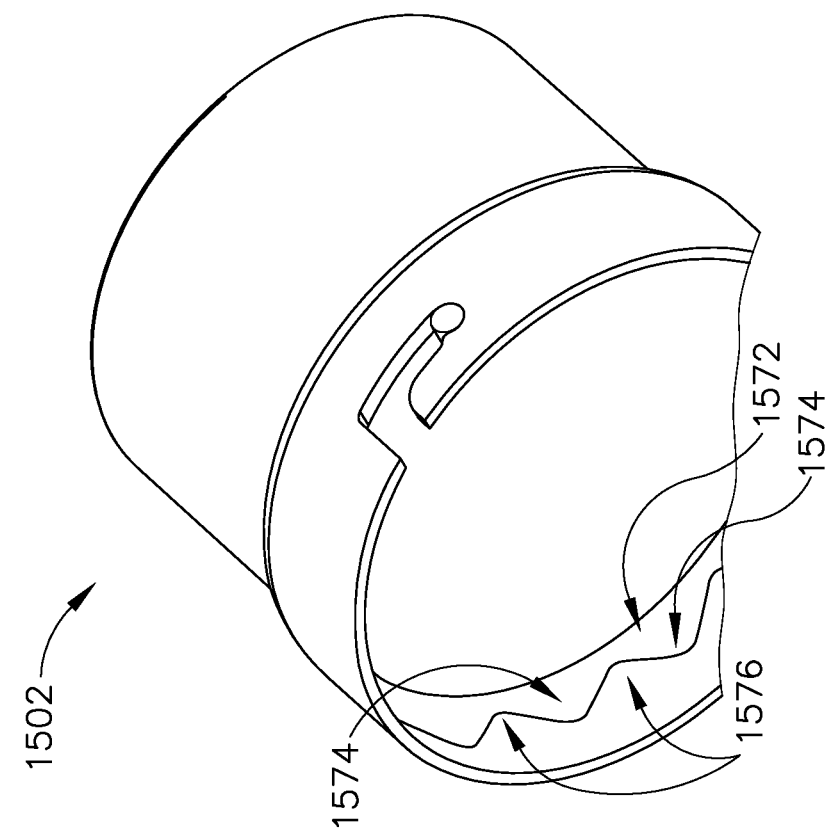
FIG. 54 depicts a partial perspective view of a transparent cover of the tissue sample holder of FIG. 52.
Figure 53:
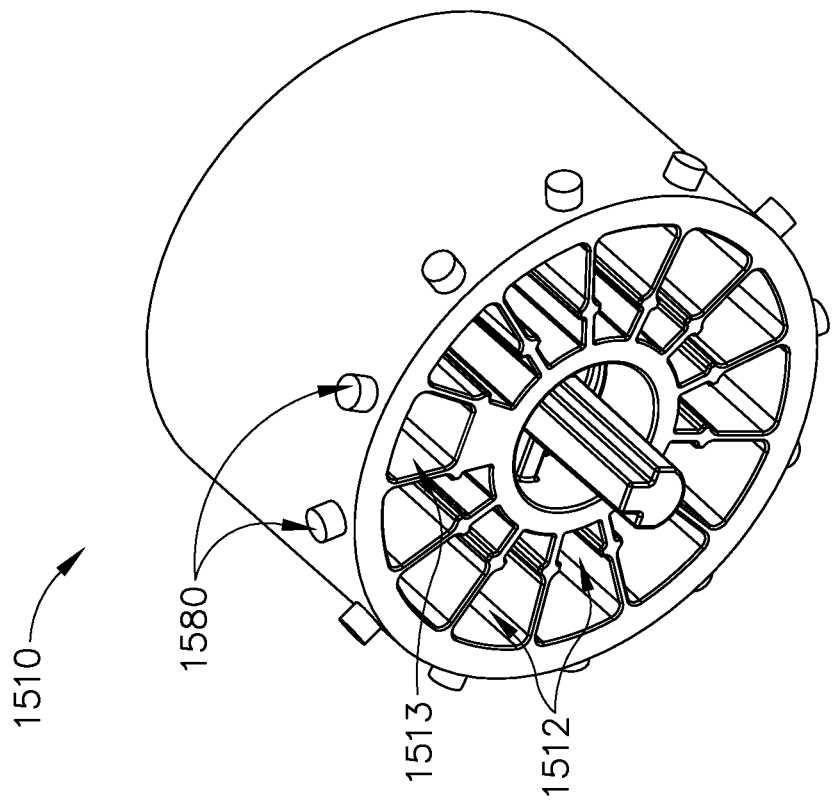
FIG. 53 depicts a partial perspective view of a manifold of the tissue sample holder of FIG. 52.

As can best be seen in FIGS. 53 and 54, tissue sample holder (1500) comprises a manifold (1510) and transparent cover (1502). As similarly described above with respect to manifold (310), manifold (1510) is configured to rotate relative to transparent cover (1502) thereby indexing a plurality of passages (1512) containing trays (not shown) with cutter lumen (151) of biopsy device (10). In addition to passages (1512), manifold (1510) comprises a single passage (1513) for receipt of a plug (not shown) that is substantially the same as plug (360) described above. It should be understood that manifold (1510) and cover (1502) are substantially the same as manifold (310) and cover (302) described above, unless otherwise noted herein.

Like with tissue sample holder (300) described above, tissue sample holder (1500) includes tissue sample holder indexing system (1570). Indexing system (1570) comprises transparent cover (1502) having a resiliently biased tab (1572) which engage a plurality of discrete indexing features (1580) oriented around the circumference of manifold (1510) to bias manifold (1510) toward a plurality of discrete rotational positions, as will be described in further detail below.

As can be seen in FIG. 53, manifold (1510) comprises a plurality of discrete indexing features (1580). Each indexing feature (1580) is generally formed of a cylindrical protrusion extending outwardly from the outer diameter of manifold (1510). Manifold (1510) of the present example has a single indexing feature (1580) corresponding to each passage (1512, 1513). As will be described in further detail below, indexing features (1580) are operable to engage with transparent cover (1502) to urge manifold (1510) relative to transparent cover (1502) to a particular indexing position. It will be appreciated that each indexing feature (1580) may comprise a variety of shapes and/or sizes beyond semi-cylindrical indentations. Additionally, although a plurality of discrete indexing features (1580) is shown, it should be understood that in other examples indexing features (1580) may be connected to each other. In other words, indexing features (1580) may alternatively comprise a single feature of variable thickness extending circumferentially around manifold (1510). Of course, other shapes, sizes, and/or configurations of indexing features (1580) will be apparent to those of ordinary skill in the art in view of the teachings herein.

FIG. 54 shows transparent cover (1502) in greater detail. As can be seen, transparent cover (1502) includes an internal cam surface (1572), which is of integral construction with transparent cover (1502). In the present example, cam surface (1572) comprises an indentation in the inner diameter of transparent cover (1502) that defines a plurality of alternating triangular indentations (1574) and protrusions (1576). As will be understood, cam surface (1572) is generally configured to engage with indexing features (1580) of manifold (1510) to move manifold (1510) into and out of an indexed position.

FIGS. 55 and 56 show indexing system (1570) in an exemplary mode of operation. Generally, FIG. 55 shows indexing system (1570) in an indexed state, where an individual passage (1512, 1513) of manifold (1510) is aligned with cutter lumen (151). Likewise, FIG. 56 shows indexing system (1570) in an unindexed state where manifold (1510) is in the process of rotating from one passage (1512, 1513) to another passage (1512, 1513). Once manifold (1510) rotates to the position shown in FIG. 56, it may continue to rotate and indexing system (1570) will return to the state shown in FIG. 55 with another passage (1512, 1513) aligned with cutter lumen (151). Accordingly, indexing system (1570) provides an additional mechanism (beyond that provided by grasping feature (184)) to ensure that a particular passage (1512, 1513) is aligned with cutter lumen (151).

As can be seen in FIG. 55, indexing system (1570) is in an indexed state. In the indexed state, cam surface (1572) of transparent cover (1502) is disposed such that a corresponding indexing feature (1580) is disposed within triangular indentation (1574) of cam surface (1572). In this state, no resilient feature maintains indexing feature (1580) in position. Instead, manifold (1510) is only fully indexed by indexing system (1570) when a vacuum is applied to tissue sample holder (1500) during operation of biopsy device (10) as described above. In particular, when vacuum is applied to tissue sample holder (1500) manifold (1010) is forced toward biopsy device (10) by the negative pressure of the vacuum. Such a force additionally drives each indexing feature (1580) further into triangular indentation (1574), thereby indexing manifold (1010).

Although tissue sample holder (1500) of the present example is shown as not including a resilient feature to maintain manifold (1010) in an indexed position, it should be understood that in other examples tissue sample holder (1500) may include such a feature. For instance, in some examples tissue sample holder may include a spring or resilient arm configured to urge manifold distally. Where such a resilient feature is used, it should be understood manifold (1010) may be retained in an indexed position regardless of the presence of vacuum in tissue sample holder (1500).

Indexing system (1570) shifts from the indexed state (FIG. 55) to the unindexed state (FIG. 56) by manifold (1510) rotating relative to transparent cover (1402) via a central shaft (not shown) as similarly described above with respect to manifold (310). Alternatively, manifold (1510) may be manually rotated by an operator as similarly described above. As manifold (1510) rotates, the rotational force drives manifold (1510) proximally as indexing feature (1580) travels along cam surface (1572) of transparent cover (1502). In the present example, manifold (1510) is relatively free to rotate when no vacuum is applied to tissue sample holder (1500). When vacuum is applied, it should be understood that manifold (1510) may still be rotated, but such rotation may require additional force to overcome camming action between indexing feature (1580) and cam surface (1572).

For manifold (1510) to index another passage (1512, 1513) with cutter lumen (151), manifold (1510) may continue to rotate relative to transparent cover (1502) via the central shaft. In examples where manifold (1510) is manually rotated, an operator may encounter tactile feedback as indexing feature (1580) travels over triangular protrusion (1576) of cam surface (1572). Once manifold (1510) is indexed with another passage (1512, 1513), indexing system (1570) will return to the indexed state depicted in FIG. 55 (but with manifold (1510) indexed to a different passage (1512, 1513)). In particular, as manifold (1510) rotates, vacuum may be applied to tissue sample holder (1500) to drive indexing feature (1580) along cam surface (1572) and into triangular indentation (1574). Accordingly, such a vacuum causes indexing system (1570) to bias manifold (1510) toward a position where each indexing feature (1580) is disposed within a corresponding triangular indentation (1574) of cam surface (1572). It should be understood that the relative positioning of each triangular indentation (1578) and each indexing feature (1580) is configured to index a particular passage (1512, 1513) with cutter lumen (115). Thus, when manifold (1510) is rotated, manifold (1510) is driven sequentially toward a indexing a passage (1512, 1513) with cutter lumen (115).

It should be understood that the coupling between the central shaft and grasping feature (184) may have some amount of backlash such that the central shaft may move without corresponding movement of grasping feature (184). Thus, while a passage (1512, 1513) of manifold (1510) may be indexed solely by the central shaft and grasping feature (184), indexing system (1570) may be operable to overcome any misindexing caused by backlash between the central shaft and grasping feature (184). Of course, in other versions backlash may be minimal and indexing system (1570) may merely provide a secondary mechanism for indexing passages (1512, 1513) of manifold (1510) with cutter lumen (151). Additionally, in some examples the mechanical motion provided by grasping feature (184) may be eliminated and tissue sample holder (1500) may be configured for manual rotation exclusively. In such examples, indexing system (1570) may provide the sole mechanism for indexing passages (1512, 1513) of manifold (1510) with cutter lumen (151). Where manual rotation is utilized (in addition to or in lieu of motion provided by grasping feature (184)), it should be understood that an operator may gasp and rotate manifold (1510) via any suitable means.

XI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device comprising: (a) a body; (b) a needle extending distally from the body, wherein the needle comprises a lateral aperture; (c) a hollow cutter, wherein the cutter is movable relative to the needle to sever a tissue sample, wherein the hollow cutter defines a cutter lumen; and (d) a tissue sample holder, wherein the tissue sample holder comprises: (i) a manifold, wherein the manifold comprises a plurality of passages and an indexing portion, wherein each passage of the plurality of passages is configured to selectively index relative to a proximal end of the hollow cutter, and (ii) a outer cover, wherein the outer cover comprises a resilient member, wherein the resilient member is configured to engage with the indexing portion of the manifold to selectively index a passage of the plurality of passages with the distal end of the hollow cutter.

Example 2

The biopsy device of Example 1, further comprising at least one tray, wherein the at least one tray is selectively insertable into one or more of the plurality of passages of the manifold.

Example 3

The biopsy device of Example 2, wherein the at least one tray comprises a plurality of sleeves, wherein each sleeve defines a tissue sample chamber, wherein each sleeve is separately insertable into a corresponding passage of the plurality of passages of the manifold.

Example 4

The biopsy device of claim 3, wherein each sleeve of the at least one tray is configured for reception of a single tissue sample.

Example 5

The biopsy device of Example 3, wherein each sleeve of the at least one tray is configured for reception of a single tissue sample.

Example 6

The biopsy device of Example 5, wherein the sleeve is configured to receive a plurality of tissue samples.

Example 7

The biopsy device of any of Examples 1 through 6, wherein the indexing portion of the manifold comprises a recess disposed in the manifold, wherein the recess comprises a distal portion and a proximal portion, wherein the distal portion defines an annular flange, wherein the proximal portion defines a plurality of triangular indentations.

Example 8

The biopsy device of Example 7, wherein the outer cover further comprises stationary member, wherein the stationary member is configured to engage with the proximal portion of the recess of the manifold, wherein the resilient member is configured to engage with the distal portion of the recess of the manifold.

Example 9

The biopsy device of any of Examples 1 through 6, wherein the indexing portion of the manifold comprises a plurality of discrete indexing features disposed about the outer diameter of the manifold.

Example 10

The biopsy device of Example 9, wherein the resilient member of the outer cover is configured to engage with the indexing features of the manifold.

Example 11

The biopsy device of Example 10, wherein each indexing feature comprises a hemispherical indentation.

Example 12

The biopsy device of Example 10, wherein each indexing feature comprises a triangular indentation.

Example 13

The biopsy device of Example 10, wherein each indexing feature comprises a semi-cylindrical indentation.

Example 14

The biopsy device of Example 10, wherein each indexing feature comprises a semi-cylindrical protrusion.

Example 15

The biopsy device of any of Examples 1 through 14, wherein each passage of the plurality of passages is configured to selectively index into coaxial alignment with the hollow cutter.

Example 16

A tissue sample holder for use with a biopsy device, the tissue sample holder comprising: (a) a cup; (b) a body, wherein the body is insertable into the cup, wherein the body defines a plurality of discrete chambers; (c) a tissue sample tray, wherein the tissue sample tray is configured for insertion into the body; and (d) an indexing assembly, wherein the indexing assembly comprises: (i) an alignment member, wherein the alignment member is associated with the body, and (ii) a biasing member, wherein the biasing member is associated with the cup, wherein the biasing member is configured to engage with the alignment member to selectively align the body relative to the cup.

Example 17

The tissue sample holder of Example 16, wherein the biasing member comprises an indentation defining a plurality of interconnected triangular indentations, wherein the alignment member comprises a plurality of discrete cylindrical members extending outwardly from the body, wherein each cylindrical member is configured to engage with a corresponding triangular indentation to selectively align the body relative to the cup.

Example 18

The tissue sample holder of any of Examples 16 and 17, wherein the indexing assembly is configured to drive alignment between the body and the cup when a vacuum is applied to the tissue sample holder.

Example 19

The tissue sample holder of any of Examples 16 through 18, wherein the body further comprises a rotation feature, wherein the rotation feature is configured to enhance grip.

Example 20

A tissue sample holder for use with a biopsy device, the tissue sample holder comprising: (a) a body, wherein the body defines a plurality of discrete chambers, wherein an exterior of the body defines a plurality of alignment features; (b) a cup, wherein the cup is configured to receive the body, wherein the cup includes a biasing member, wherein the biasing member is configured to resiliently engage with the plurality of alignment features of the body to selectively align the body relative to the cup; and (c) a tissue sample tray, wherein the tissue sample tray is configured for insertion into the body.

XII. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A biopsy device comprising:
 (a) a body;
 (b) a needle extending distally from the body, wherein the needle includes an aperture for receiving a tissue sample;
 (c) a hollow cutter, wherein the cutter is movable relative to the needle to sever a tissue sample, wherein the hollow cutter defines a cutter lumen; and
 (d) a tissue sample holder, wherein the tissue sample holder includes:
  (i) a manifold, wherein the manifold includes a plurality of passages positioned within an outer perimeter defined by the manifold and a plurality of indexing portions positioned around the outer perimeter of the manifold, wherein each passage of the plurality of passages is configured to selectively index relative to a proximal end of the hollow cutter, and
  (ii) an outer cover, wherein the outer cover includes a resilient member with a protrusion extending therefrom, wherein the resilient member is configured to be resiliently movable relative to the outer cover and is configured to respond to rotation of the manifold in either a clockwise or counter-clockwise direction such that the resilient member is configured to engage with each indexing portion of the manifold via the protrusion to selectively bias the manifold, thereby indexing a passage of the plurality of passages with the proximal end of the hollow cutter, wherein each indexing portion defines a symmetrical shape configured to permit the rotation of the manifold in either the clockwise or counter-clockwise direction.

2. The biopsy device of claim 1 further including at least one tray, wherein the at least one tray is selectively insertable into one or more of the plurality of passages of the manifold.

3. The biopsy device of claim 2, wherein the at least one tray includes a plurality of sleeves, wherein each sleeve defines a tissue sample chamber, wherein each sleeve is separately insertable into a corresponding passage of the plurality of passages of the manifold.

4. The biopsy device of claim 3, wherein each sleeve of the at least one tray is configured for reception of a single tissue sample.

5. The biopsy device of claim 2, wherein the at least one tray defines a single sleeve defining a tissue sample chamber, wherein the sleeve is insertable into a single passage of the plurality of passages of the manifold.

6. The biopsy device of claim 1, wherein the plurality of indexing portions of the manifold includes a recess disposed in the manifold, wherein the recess includes a distal portion and a proximal portion, wherein the distal portion defines an annular flange, wherein the proximal portion defines a plurality of triangular indentations.

7. The biopsy device of claim 6, wherein the outer cover further includes stationary member, wherein the stationary member is configured to engage with the proximal portion of the recess of the manifold, wherein the protrusion of the outer cover is configured to engage with the distal portion of the recess of the manifold.

8. The biopsy device of claim 1, wherein the plurality of indexing portions of the manifold includes a plurality of discrete indexing features disposed about the outer diameter of the manifold.

9. The biopsy device of claim 8, wherein the protrusion of the outer cover is configured to engage with the plurality of indexing features of the manifold.

10. The biopsy device of claim 9, wherein each indexing feature of the plurality of indexing features includes a hemispherical indentation.

11. The biopsy device of claim 9, wherein each indexing feature of the plurality of indexing features includes a triangular indentation.

12. The biopsy device of claim 9, wherein each indexing feature of the plurality of indexing features includes a semi-cylindrical indentation.

13. The biopsy device of claim 9, wherein each indexing feature of the plurality of indexing features includes a semi-cylindrical protrusion.

14. The biopsy device of claim 1, wherein each passage of the plurality of passages is configured to selectively index into coaxial alignment with the hollow cutter.

15. The biopsy device of claim 1, wherein the resilient member of the outer cover is a living hinge.

16. The biopsy device of claim 15, wherein the outer cover further includes a cover body, wherein the living hinge couples the protrusion to the cover body.

17. The biopsy device of claim 1, wherein the outer cover is configured to cover at least a portion of the manifold.

18. A tissue sample holder for use with a biopsy device, the tissue sample holder comprising:
(a) a cup;
(b) a body, wherein the body is insertable into the cup, wherein the body defines a plurality of discrete chambers disposed within an exterior surface defined by the body;
(c) a tissue sample tray, wherein the tissue sample tray is configured for insertion into the body; and
(d) an indexing assembly, wherein the indexing assembly includes:
(i) an alignment member, and
(ii) a biasing member, wherein the biasing member includes a plurality of alternatingly interconnected recesses and projections arranged along a surface of the biasing member, wherein the biasing member is configured to engage with the alignment member to selectively align the body relative to the cup into a plurality of alignment positions as the body is rotated relative to the cup;
wherein the indexing assembly is positioned about the exterior surface of the body such that the alignment member is operable to engage the biasing member along the exterior surface; and
wherein the interconnected recesses and projections of the biasing member together form a repeating symmetrical pattern such that the indexing assembly is configured to bias the body while permitting independent rotation of the body in multiple directions.

19. The tissue sample holder of claim 18, wherein the biasing member is associated with the cup.

20. A tissue sample holder for use with a biopsy device, the tissue sample holder comprising:
(a) a body, wherein the body defines a plurality of discrete chambers, wherein the body defines a plurality of alignment features disposed on an exterior surface of the body and extending around the plurality of discrete chambers, wherein the exterior surface of the body further defines a retention feature;
(b) a cup, wherein the cup is configured to receive the body such that the cup is configured to cover at least a portion of the exterior surface of the body, wherein the body is rotatable relative to the cup, wherein the cup includes a biasing member and a static member, wherein the biasing member is configured to resiliently bias the retention feature of the body along an axis of rotation of the body such that the static member successively engages each of the plurality of alignment features of the body to selectively align the body relative to the cup, wherein each alignment feature defines a symmetrical shape such that the plurality of alignment features are configured to permit independent bi-directional rotation of the body; and
(c) a tissue sample tray, wherein the tissue sample tray is configured for insertion into the body.

* * * * *